United States Patent
D'Hondt et al.

(10) Patent No.: US 12,258,389 B2
(45) Date of Patent: *Mar. 25, 2025

(54) METHODS AND COMPOSITIONS FOR INHIBITION OF EGF/EGFR PATHWAY IN COMBINATION WITH TYROSINE KINASE INHIBITORS

(71) Applicant: In3Bio Ltd., Hamilton (BM)

(72) Inventors: Erik D'Hondt, Bazel (BE); Miguel Ángel Molina Vila, Badalona (ES)

(73) Assignee: In3Bio Ltd., Hamilton (BM)

(*) Notice: Subject to any disclaimer, the term of this patent is extended or adjusted under 35 U.S.C. 154(b) by 361 days.

This patent is subject to a terminal disclaimer.

(21) Appl. No.: 17/358,788

(22) Filed: Jun. 25, 2021

(65) Prior Publication Data

US 2022/0041704 A1 Feb. 10, 2022

Related U.S. Application Data

(63) Continuation of application No. 15/073,021, filed on Mar. 17, 2016.

(60) Provisional application No. 62/160,183, filed on May 12, 2015.

(51) Int. Cl.
| | |
|---|---|
| C07K 16/22 | (2006.01) |
| A61K 31/506 | (2006.01) |
| A61K 31/517 | (2006.01) |
| A61K 31/5377 | (2006.01) |
| A61K 31/7084 | (2006.01) |
| A61K 39/00 | (2006.01) |
| A61K 39/395 | (2006.01) |
| A61K 45/06 | (2006.01) |

(52) U.S. Cl.
CPC ............ *C07K 16/22* (2013.01); *A61K 31/506* (2013.01); *A61K 31/517* (2013.01); *A61K 31/5377* (2013.01); *A61K 31/7084* (2013.01); *A61K 39/00* (2013.01); *A61K 39/001104* (2018.08); *A61K 39/001131* (2018.08); *A61K 39/3955* (2013.01); *A61K 45/06* (2013.01); *A61K 2039/545* (2013.01); *C07K 2317/76* (2013.01)

(58) Field of Classification Search
None
See application file for complete search history.

(56) References Cited

U.S. PATENT DOCUMENTS

| | | |
|---|---|---|
| 8,828,391 B2 | 9/2014 | Denis |
| 2006/0251654 A1 | 9/2006 | Casimiro et al. |
| 2012/0294867 A1 | 11/2012 | Denis et al. |

FOREIGN PATENT DOCUMENTS

| | | |
|---|---|---|
| CN | 103533961 A | 1/2014 |
| CN | 104066447 A | 9/2014 |
| JP | 2014513706 B2 | 6/2014 |
| JP | 2014534258 B2 | 12/2014 |
| KR | 10-2014-0031903 A | 3/2014 |
| KR | 10-2014-0108235 A | 9/2014 |
| WO | 2013076580 A2 | 5/2013 |

OTHER PUBLICATIONS

Jiang et al., Correlation of activated STAT3 expression with clinicopathologic features in lung adenocarcinoma and squamous cell carcinoma. Molecular Diagnosis & Therapy 15 (6):347-352, 2011.*
Looyenga et al., STAT3 is activated by JAK2 independent of key oncogenic driver mutations in non-small cell lung carcinoma. Plos One 7 (2): e30820, 2012.*
Chiu Huan-Chih et al. Suppression of Stat3 Activity Sensitizes Gefitinib-resistant Non Small Cell Lung Cancer Cells. Biochemical Pharmacology vol. 81, No. 11. Jun. 2011.
Wang et al. Combined Erlotinib Cetuximab Overcome the Acquired Resistance to Epidermal Growth Factor Receptors Tyrosine Kinase Inhibitor in Non-Small-Cell Lung Cancer. Journal of Cancer Research and Clinical Oncology. vol. 138, No. 12. Jul. 2012.
Patel et al. Anti-Epidermal Growth Factor Receptor Monoclonal Antibody Cetuximab Inhibits EGFR/HER-2 Heterodimerization and Activation. International Journal of Oncology. vol. 34, No. 1. Jan. 2009.
Zhong et al. Immunotherapy: How to Apply to Lung Cancer? Progress in Internal Medicine of Oncology in China—Collection of Essays on Education of Chinese Oncologists. Jul. 2014.
Second Office Action in corresponding Chinese Application No. 201680038424.4 dated May 8, 2021.

(Continued)

*Primary Examiner* — Ruixiang Li
(74) *Attorney, Agent, or Firm* — Withers Bergman LLP; John C. Serio

(57) ABSTRACT

A method of treating patients suffering from cancers driven by deregulated Human Epidermal Growth Factor Receptor (HER1/Human EGFR) comprising administering to a patient in need of such treatment a flexible and active regimen for combining a tyrosine kinase inhibitor (TKI) and anti-EGF antibodies for inhibition of the pathway activated by EGF-EGFR binding (mAb). The anti-EGF antibodies can be produced by active immunization or provided passively by the administration of antibodies that are anti-EGF. The method comprises TKI administered according to a continuous regimen based on an average daily dose in the range of 10 to 150 mg and the mAb is co-administered either actively or passively according to a dosing regimen achieving a therapeutic effective amount repeated thrice, twice or once a week, once in two weeks, once in three weeks or at least once monthly.

7 Claims, 48 Drawing Sheets

Specification includes a Sequence Listing.

(56) References Cited

OTHER PUBLICATIONS

Office Action in corresponding European Application No. 16741385.5 dated Apr. 12, 2021.
Garcia et al. Effective Inhibition of the Epidermal Growth Factor/ Epidermal Growth Factor Receptor Binding By Anti, Epidermal Growth Factor Antibodies is Related to Better Survival in Advanced Non-Cell Lung Cancer Patients Treated With the Epidermal Growth Factor Cancer Vaccine. 2008.
Decision of Refusal in corresponding JP Application No. 2017-559450 dated Jun. 8, 2021.
Vinageras et al. Phase II Randomized Controlled Trial of an Epidermal Growth Factor Vaccine in Advanced Non-Small Cell Lung Cancer. J Clin. Oncol. 26: 1452-1458, 2008.
Wolf et al. Attenuated Endocytosis and Toxicity of a Mutant Cholera Toxin with Decreased Ability to Cluster Ganglioside GM1 Molecules. Infect. Immun. 76(4):1476-1484, 2008.
Sugiura, M. et al. Lung Cancer Vaccine Therapy, Lung Cancer Society vol. 49, 2009.
Kim, H. et al. Combined Lapatinib and Cetuximab Enhance Cytotoxicity Against Gefitinib—Resistant Lung Cancer Cells, Molecular Cancer Therapeutics, 2008.
Office Action in corresponding Russian Application No. 2017143182 dated Mar. 26, 2020.
Office Action in corresponding Japanese Application No. 2017-559450 dated Jun. 9, 2020.
Niu et al. In vitro human cell line models to predict clinical response to anticancer drugs. Pharmacogenomics 2015; 16 (3) 273-285.
Jian Y. Cheng et al. 11 CIMAvax EGF Vaccine for stage I I I b/IV non-small cell lung carcinoma 11, Human Vaccines & Immuntherapeutics, vol. 8, No. 12, Dec. 1, 2012, pp. 1799-1801.
Database Embase [Online] Elsevier Science Publishers, Amsterdam NL; Aug. 2009 (Aug. 2009)9 Liu D et al.: "Inhibitory effect of gefitinib combined with DNA vaccine targeting EGFR against mouse lung cancer Lewis cells;" Database accession No. EMB-2009506152 abstract & Chinese Journal of Cancer Biotherapy 2009 China International Book Trading Corp. (Guoj I Shudian) CHN 9 vol. 169 No. 49 Aug. 2009.
D V Parums: "Status of immune therapy in Non-Small Cell Lung Cancer (NSCLC)", Drugs of the Future 9 Jul. 1, 2014.
Office Action in corresponding Israeli Application No. 255582 dated Nov. 19, 2020.
Regales et al. Dual targeting of EGFR can overcome a major drug resistance mutation in mouse models of EGFR mutant lung cancer. 2009.
Goldberg et al. Randomized trial of Afatinib plus cetuximab versus Aftainib alone for first-Line treatment of EGFR-mutant non-small-cell lung cancer: final results from SWOG S1403. 2020.
Beatriz Garcia et al., 'Effective Inhibition of the Epidermal Growth Factor/Epidermal Growth Factor Receptor Binding by Anti-Epidermal Growth Factor Antibodies Is Related to Better Survival in Advanced Non-Small-Cell Lung Cancer Patients Treated with the Epidermal Growth Factor Cancer Vaccine', Clin Cancer Res 2008;14(3) Feb. 1, 2008.
Office Action in corresponding Korean application No. 10-2017-7035561 dated Jul. 14, 2023.
Bowie et al. Deciphering the Message in Protein Sequences: Tolerance to Amino Acid Substitutions. Science, 1990, 247:1306-1310.
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111 :2129-2138, 1990.
Lazar et al. Transforming Growth Factor alpha: Mutation of Aspartic Acid 47 and Leucine 48 Results in Different Biological Activities. Mol. Cell. Biol., 8:1247-1252, 1988.
Whisstock et al. Prediction of proteinfunction fromprotein sequence and structure. Quarterly Reviews in Biophysics. 36 (3):307-340, 2007.
Oransky et al. Navigating the "No Man's Land" of TKI-Failed EGFR-Mutated Non-Small Cell Lung Cancer (NSCLC): A Review. Neoplasia (2018) 20, 92-98.
Lee et al. Treatments for EGFR-mutant non-small cell lung cancer (NSCLC): The road to a success, paved with failures. Pharmacology & Therapeutics 174 (2017) 1-21).
Wu et al. Gefitinib resistance resulted from STAT3-mediated Akt activation in lung cancer cells. Dec. 2013.

\* cited by examiner

Murine EGF (full length)
*Human EGF (full length)*
Linker-1 (4 amino acids)
*Linker-2 (14 amino acids)*
CTB
6xHis purification tag

<u>MNSYPGCPSSYDGYCLNGGVCMHIESLDSYTCNCVIGYSGDRCQTRDLRWWELR</u> GSSG
*NSDSECPLSHDGYCLHDGVCMYIEALDKYACNCVVGYIGERCQYRDLKWWELR* *GGSGGTSGGGGSG*
TPQNITDLCAEYHNTQIHTLNDKIFSYTESLAGKREMAIITFKNGATFQVEVPGSQHIDSQKKAIERMKDTLRIAYLTEAKV
EKLCVWNNKTPHAIAAISMAN HHHHHH

FIG. 20A

Human EGF (full length)

Linker-1 (4 amino acids)

Linker-2 (14 amino acids)

*CTB (with G33D mutation)*

NSDSECPLSHDGYCLHDGVCMYIEALDKYACNCVVGYIGERCQYRDLKWWELR GSSG
NSDSECPLSHDGYCLHDGVCMYIEALDKYACNCVVGYIGERCQYRDLKWWELR GGSGGTSGGGGGSG

*TPQNITDLCAEYHNTQIHTLNDKIFSYTESLADKREMAIITFKNGATFQVEVPGSQHIDSQKKAIERMKDTLRIAYLTEAKV
EKLCVWNNKTPPAIAAISMAN*

FIG. 20B

METHODS AND COMPOSITIONS FOR INHIBITION OF EGF/EGFR PATHWAY IN COMBINATION WITH TYROSINE KINASE INHIBITORS

RELATED APPLICATIONS

This application is a continuation of U.S. application Ser. No. 15/073,021, filed on Mar. 17, 2016, entitled METHODS AND COMPOSITIONS FOR INHIBITION OF EGF/EGFR PATHWAY IN COMBINATION WITH TYROSINE KINASE INHIBITORS, which claims priority to U.S. Provisional Application No. 62/160,183, filed on May 12, 2015, entitled METHODS AND COMPOSITIONS FOR INHIBITION OF EGF/EGFR PATHWAY IN COMBINATION WITH TYROSINE KINASE INHIBITORS, which is incorporated by reference herein in its entirety for all purposes.

FIELD OF THE INVENTION

Embodiments of the present invention are directed to methods for treating and preventing disease conditions, such as cancer, particularly in those individuals who have developed a resistance or who are not responsive to tyrosine kinase inhibitor (TKI) therapy.

BACKGROUND OF INVENTION

Non-small-cell lung cancer (NSCLC) is the leading cause of cancer related deaths in the world and despite recent advances in treatment and diagnosis, the 5-year survival remains at ~16%. This poor outcome is largely due to the advanced disease stage, the robust nature of the disease and degree of metastasis at diagnosis. Although significant advances have been made in elucidating the genomic abnormalities that cause malignant cancer cells, currently available chemotherapy remains unsatisfactory, and the prognosis for the majority of patients diagnosed with cancer remains troubling.

Most chemotherapeutic agents act on a specific molecular target thought to be involved in the development of the malignant phenotype. However, a complex network of signaling pathways regulate cell proliferation and the majority of malignant cancers are facilitated by multiple genetic abnormalities in these pathways. Although treatment of lung cancers with standard cytotoxic chemotherapies has been optimized for efficacy, more recent approaches to NSCLC therapeutics are based on classification of NSCLC into molecular subsets based on their distinct oncogene driver. These molecular drivers of NSCLC can be attacked therapeutically with targeted agents directed against the specific oncogenes.

Most previous chemotherapy drugs for cancer were non-selective in their activity. Although their exact mechanisms of action were varied and complex, they generally worked by damaging cells undergoing mitosis, which is usually more common in malignant tumors than in most normal tissues. Targeted agents are designed to be selective in their effects by modulating the activity of proteins necessary and essential for oncogenesis and maintenance of cancer, particularly enzymes driving the uncontrolled growth, angiogenesis, invasiveness, and metastasis characteristic of malignant tumors. The increased differential activity usually results in fewer troubling side effects for cancer patients, particularly less nausea, vomiting, and death of cells in the bone marrow and gastrointestinal tract, and increased effectiveness against tumor cells.

A promising set of targets for therapeutic intervention in the treatment of cancer includes the members of the HER-kinase axis. They are frequently up-regulated in solid epithelial tumors of, by way of example, the prostate, lung and breast, and are also up-regulated in glioblastoma tumors. Epidermal growth factor receptor (EGFR) is a member of the HER-kinase axis, and has been the target of choice for the development of several different cancer therapies. EGFR tyrosine kinase inhibitors (EGFR-TKIs) are among these therapies, since the reversible phosphorylation of tyrosine residues is required for activation of the EGFR pathway. In other words, EGFR-TKIs block a cell surface receptor responsible for triggering and/or maintaining the cell signaling pathway that induces tumor cell growth and division. Specifically, it is believed that these inhibitors interfere with the EGFR kinase domain, referred to as HER-1. Among the more promising EGFR-TKIs are three series of compounds: quinazolines, pyridopyrimidines and pyrrolopyrimidines.

It has been found that the epidermal growth factor receptor (EGFR) is highly expressed or amplified in many NSCLC patients, although clinical investigation with EGFR-specific tyrosine kinase inhibitors (TKIs) identified patients whose tumors bear gain-of-function EGFR mutations as the subset with the best response. Although, these patients initially respond to EGFR-targeted therapies, all will unfortunately eventually relapse, a problematic limitation of the long term effectiveness of targeted therapies. Overall, the median time to progression on EGFR-targeted therapies is about 8-14 months. Multiple mechanisms of acquired resistance to EGFR-targeted inhibitors have been discovered and validated in patients.

Two of the more popular FDA-approved TKIs in clinical use for NSCLC include gefitnib (AstraZeneca UK Ltd.; tradename IRESSA®); hereinafter "IRESSA" or "gefitnib" and erlotinib (Genentech, Inc. tradename TARCEVA®; hereinafter "TARCEVA" or erlotinib); both have in some patients generated encouraging clinical results and are currently the standard of care for first line treatment of EGFR-mut advanced NSCLC patients.

A significant limitation in using these compounds is that recipients thereof may develop a resistance to their therapeutic effects after they initially respond to therapy, or they may not respond to EGFR-TKIs to any measurable degree. Thus, although the compounds may, at first, exhibit strong anti-tumor properties, they may soon become less potent or entirely ineffective in the treatment of cancer. Moreover, since medical research has heretofore not completely elucidated the biomolecular or pathological mechanism responsible for this resistance, some patients who have exhibited such resistance to date have been left with few therapeutic alternatives to treat their disease The secondary gate-keeper T790M mutation, which increases EGFR-ATP binding affinity, occur in 50% of patients whose tumors progress on EGFR-specific TKIs. In addition, MET amplification following treatment with EGFR inhibitors has been reported in about 5-15% of NSCLC patients. EGFR-T790M and MET-amplified tumor cells can be detected in tumors before EGFR-targeted therapies, suggesting these cells are selectively enriched upon treatment. Furthermore, detection of either T790M or amplified MET with HGF expression before EGFR TKI treatment is associated with decreased duration of response to EGFR-targeted treatments Without being bound to any particular theory, it is thought that alternative receptor tyrosine kinases that are neither mutated nor amplified may also contribute to acquired resistance to EGFR-targeted therapies. Alternative receptor tyrosine kinases, also referred to as 'bypass pathways', have been identified as mechanisms of both intrinsic and acquired resistance to targeted therapeutics including EGFR TKIs. Compared with resistance via acquisition of gate-keeper mutations, acquired resistance mechanisms involving induction of distinct signaling pathways lacking genetic alterations are less documented in the literature.

Treatment with receptor-tyrosine kinase inhibitors (TKIs) has improved progression-free and overall survival in patients with advanced non-small cell lung cancer (NSCLC). However, despite initial responses and significant remissions, the development of secondary resistance inevitably leads to treatment failure. It appears that a single mode of action of tyrosine kinase inhibitors, such as gefitinib or erlotinib can provide only temporary success. It appears that what is needed to address this resistance problem is their combination with additional therapeutics, such as small molecules or antibodies, with TKIs to overcome secondary EGFR-TKI resistance for the near future.

SUMMARY OF INVENTION

An object of the present invention is a method of treating patients suffering from cancers driven by deregulated Human Epidermal Growth Factor Receptor (HER/Human EGFR) comprising administering to a patient in need of such treatment a flexible and active regimen for combining a tyrosine kinase inhibitor (TKI) with active EGF Pathway Immunization (EGF PTI) for inhibition of the pathway activated by EGF-EGFR, wherein in this method the TKI is administered according to a continuous regimen based on an average daily dose in the range of 10 to 50 mg and the EGF PTI is co-administered according to a dosing regimen achieving a therapeutic effective amount repeated thrice, twice or once a week, once in two weeks, once in three weeks or at least once monthly.

A further object of the present invention is a method of treating a patient suffering from a non-small cell lung cancer (NSCLC) driven by deregulated Human Epidermal Growth Factor Receptor (HER1/Human EGFR), wherein: the patient has a tumor expressing mutated forms of the EGFR, comprising administering to a patient in need of such treatment a flexible and active regimen for combining a tyrosine kinase inhibitor (TKI) and active immunization targeting EGF wherein in this method the TKI is administered according to a continuous regimen based on an average daily dose in the range of about 10 to 150 mg and the active immunization, EGF PTI is co-administered according to a therapeutic effective amount repeated thrice, twice or once a week, once in two weeks, once in three weeks or at least once monthly, wherein the method results in preventing acquiring resistance to TKI treatment.

Another object of the invention is a pharmaceutical kit; comprising a first compartment which comprises an effective amount of an anti EGF targeted antibodies and a second compartment which comprises an effective amount of a TKI.

A further object of the invention is a pharmaceutical kit; comprising a first compartment which comprises an effective amount of a vaccine producing an immune response to EGF and a second compartment which comprises an effective amount of a TKI.

Another object of the invention is a pharmaceutical kit; comprising a first compartment which comprises an effective amount of a vaccine producing an immune response to EGFR and a second compartment which comprises an effective amount of a TKI.

A further object of the invention is a TKI for use in a method of treatment of a patient suffering from a cancer driven by deregulated Human Epidermal Growth Factor Receptor (HER/Human EGFR) by co-administration with a vaccine producing an immune response to EGF, wherein the TKI is administered according to a continuous regimen based on an average daily dose in the range of about 10 to 150 mg and the vaccine producing an immune response to EGF is co-administered according to a therapeutic effective amount repeated thrice, twice or once a week, once in two weeks, once in three weeks or at least once monthly to a patient in need of such treatment.

A further object of the invention is the use of a TKI for preparation of a pharmaceutical kit for treatment of patients suffering from cancers driven by deregulated Human Epidermal Growth Factor Receptor (HER/Human EGFR), comprising a first compartment which comprises an effective amount of a vaccine producing an immune response to EGF and a second compartment which comprises an effective amount of a TKI, wherein the TKI is to be administered according to a continuous regimen based on an average daily dose in the range of about 10 to 150 mg and the vaccine is administered prior to initiating TKI therapy according to a dosing regimen ranging from an average weekly dose a therapeutic effective amount repeated thrice, twice or once a week, once in two weeks, once in three weeks or at least once monthly to a patient in need of such treatment.

BRIEF DESCRIPTION OF THE DRAWINGS

The present disclosure is further described in the detailed description which follows, in reference to the noted plurality of drawings by way of non-limiting examples of embodiments of the present disclosure, in which like reference numerals represent similar parts throughout the several views of the drawings, and wherein:

FIGS. 20A and 20B show sequences of fusion proteins according to the invention that produces anti-EGF antibodies;

DETAILS OF THE INVENTION

Figure 1:
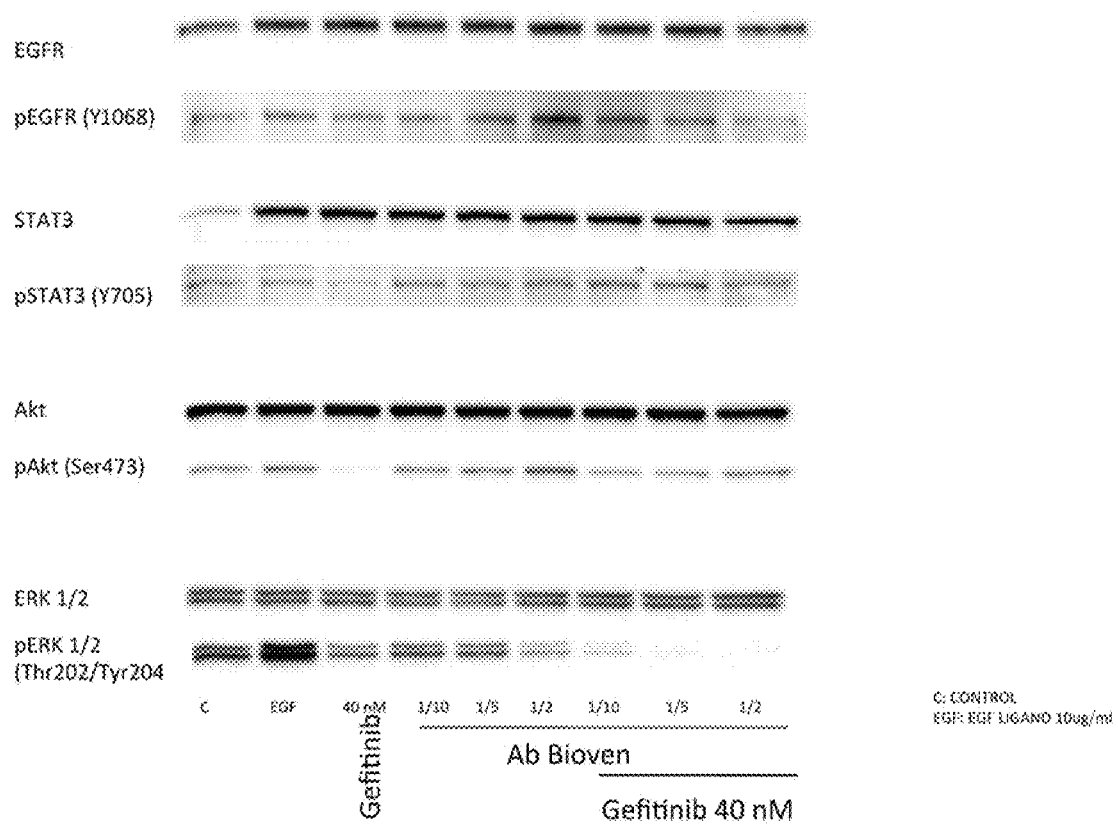
FIG. 1 shows a SDS-PAGE-WB (Western blot) displaying anti EGF on inhibition of EGF/EGFR pathway.

Embodiments of the technology described herein are based on the discovery that anti EGF antibodies at physiological concentrations, have inhibitory effects on phosphorylation of EGFR, Akt and ERK1/2 are at least as significant as the effect of TKIs on these signaling molecules. It was further discovered that that combination treatment of the anti EGF antibodies and TKIs shows additional effect for pEGFR, pAkt, pERK1/2 and pSTAT-3 inhibition. In some embodiments, such antibodies or antigen-binding fragments thereof can be used in the methods of treating NSLC. It is contemplated within the scope of the disclosure that the anti EGF antibodies can be actively produced in vivo by the administration of a vaccine producing an immune response to EGF. It is further contemplated within the scope of the disclosure that passive monoclonal anti EFG antibodies can be administered.

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The terms "decrease," "reduce," "reduced", "reduction", "decrease," and "inhibit" are all used herein generally to mean a decrease by a statistically significant amount relative to a reference. However, for avoidance of doubt, "reduce," "reduction" or "decrease" or "inhibit" typically means a decrease by at least 10% as compared to a reference level and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to the reference level, or any decrease between 10-99% as compared to the absence of a given treatment.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated." The terms "purified" or "substantially purified" refer to an isolated nucleic acid or polypeptide that is at least 95% by weight the subject nucleic acid or polypeptide, including, for example, at least 96%, at least 97%, at least 98%, at least 99% or more.

As used herein, the terms "proteins" and "polypeptides" are used interchangeably herein to designate a series of amino acid residues connected to the other by peptide bonds between the alpha-amino and carboxy groups of adjacent residues. The terms "protein", and "polypeptide", which are used interchangeably herein, refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to an encoded gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein the term, "Antibody" includes any immunoglobulin molecule that recognizes and specifically binds to a target, such as a protein, polypeptide, peptide, carbohydrate, polynucleotide, lipid, etc., through at least one antigen recognition site within the variable region of the immunoglobulin molecule. As used herein, the term is used in the broadest sense and encompasses intact polyclonal antibodies, intact monoclonal antibodies, antibody fragments (such as Fab, Fab', F(ab').sub.2, and Fv fragments), single chain Fv (scFv) mutants, multi-specific antibodies such as bispecific antibodies generated from at least two intact antibodies, fusion proteins comprising an antibody portion, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively.

The different classes of immunoglobulins have different and well known subunit structures and three-dimensional configurations. Antibodies can be naked or conjugated to other molecules such as cytotoxics, toxins, radioisotopes, etc. Antibodies can be administered by actively producing them in vivo or passive administering monoclonal antibodies.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG-1, IgG-2, IgA-1, IgA-2, and etc. The heavy chain constant domains that correspond to the different classes of immunoglobulins are called $\alpha$, $\delta$, $\epsilon$, $\gamma$, and $\mu$, and respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably, to refer to an antibody in its substantially intact form, not antibody fragments as defined below. The terms particularly refer to an antibody with heavy chains that contain the Fc region.

"Antibody fragments" comprise only a portion of an intact antibody, wherein the portion preferably retains at least one, preferably most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise on antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population comprise essentially identical amino acid sequence except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

"Tumor", as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing or decreasing inflammation and/or tissue/organ damage, decreasing the rate of disease progression, amelioration or palliation of the disease state, and remission or improved prognosis. In some embodiments, antibodies of the invention are used to delay development of a disease or disorder.

A "pharmaceutical excipient" shall mean those commonly utilized within the pharmaceutical art and in particular those found "Handbook of excipients", (Raymond C. Rowe, Paul J. Sheskey, Paul J. Weller-4$^{th}$ Edition, 2003), the contents of which are incorporated in their entirety.

A "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount would be less than the therapeutically effective amount.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, *Chem Intl. Ed. Engl.*, 33: 183-186 (1994)); dynemicin, including dynemicin A; an espmeramicin; as well as neocarzinostatin chromophore and related chromoprotein enediyne antibiotic chromophores), ad acinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromefthylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

"Patient response" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e. reduction, slowing down or complete stopping) of disease spread; (6) decrease of cell proliferation, invasion or metastasis, which may, but does not have to, result in the regression or ablation of a disease lesion; (7) relief, to some extent, of one or more symptoms associated with the disorder; (8) increase in the length of disease-free presentation following treatment; and/or (9) decreased mortality at a given point of time following treatment.

By "tissue or cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

EGFR-TKI Agents

Methods of the invention involve administering an EGFR-TKI agent to a subject. The family of epidermal growth factor receptors (EGFR) comprises four structurally related cell-surface receptor tyrosine kinases that bind and elicit functions in response to members of the epidermal growth factor (EGF) family. In humans, this includes EGFR, also known as Her-1 and ErbB1, Her-2, also referred to as Neu and ErbB2, Her-3 (ErbB3), and Her-4 (ErbB4). Hyperactivation of ErbB signaling is associated with the development of a wide variety of solid tumors. Accordingly, in various additional embodiments, the present invention includes combinations of anti-EGF antibodies with erlotinib as well as other EGFR inhibitors, such as gefitinib, afatinib, panitumumab and cetuximab, as well as HER2 inhibitors such as lapatinib, pertuzumab and trastuzumab. In certain embodiments, the EGFR-TKI is erlotinib, the active ingredient of the drug currently marketed under the trade name TARCEVA®.

Erlotinib is a tyrosine kinase inhibitor, a quinazolinamine with the chemical name N-(3-ethynylphenyl)-6,7-bis(2-methoxyethoxy)-4-quinazolinamine. In specific embodiments, the erlotinib is erlotinib hydrochloride. TARCEVA® tablets for oral administration are available in three dosage strengths containing erlotinib hydrochloride (27.3 mg, 109.3 mg and 163.9 mg) equivalent to 25 mg, 100 mg and 150 mg erlotinib and the following inactive ingredients: lactose monohydrate, hypromellose, hydroxypropyl cellulose, magnesium stearate, microcrystalline cellulose, sodium starch glycolate, sodium lauryl sulfate and titanium dioxide. The tablets also contain trace amounts of color additives, including FD&C Yellow #6 (25 mg only) for product identification. Further information is available from the approved drug label. The approved recommended dose of TARCEVA® for NSCLC is 150 mg/day; the approved dose for pancreatic cancer is 100 mg/day. Doses may be reduced in 50 mg decrements when necessary.

In other embodiments, the EGFR-TKI agent is gefitinib, the active ingredient of the drug marketed under the trade name IRESSA®. Gefitinib is a tyrosine kinase inhibitor with the chemical name 4-quinazolinamine, N-(3-chloro-4-fluorophenyl)-7-methoxy-6-[3-4-morpholin) propoxy] The clinical formulation is supplied as 250 mg tablets, containing the active ingredient, lactose monohydrate, microcrystalline cellulose, croscarmellose sodium, povidone, sodium lauryl sulfate and magnesium stearate. The recommended dose as a single therapy is one 250 mg tablet per day. Further information can be found on the approved drug label.

Other EGFR inhibitors, such as afatinib, panitumumab and cetuximab, as well as HER2 inhibitors such as lapatinib, pertuzumab and trastuzumab are known in the art and, thus, a person of ordinary skill would readily know their structure, formulation, dosing, and administration, etc. (e.g., based on published medical information such as an approved drug label) as would be required in use with the present invention.

Small-molecule inhibitors of EGFR lead to clinical response in some patients with NSCLC, and this response correlates with activating mutations in the kinase domain of EGFR. These mutant proteins are sufficient to transform human epithelial cells and are required for the survival of NSCLC cell lines. Understanding the biological changes induced by mutant EGFR and its contribution to oncogenesis requires a thorough understanding of the downstream signal transduction pathways it activates. Signal transducer and activator of transcription 3 (STAT3) is an oncogenic transcription factor that is active in many human cancers and regulates the transcription of several genes that are involved in cell cycle progression, antiapoptosis, cell survival, and angiogenesis.

STAT3 can be activated by EGFR, JAK2, and other tyrosine kinases whose activation can be mediated by EGF, leukemia inhibitory factor (LIF), and other cytokines. Therefore, STAT3 is a convergent point of many signaling pathways and has a major role in oncogenesis and tumor metastasis. It is thought that STAT3 is activated by various forms of mutant EGFR and may contribute to the oncogenic effects of these mutants in fibroblasts and human lung cancer cells.

Following activation by either ligand binding or mutation, EGFR initiates a cascade of signal transduction pathways that alter the biology of the cell through transcriptional and post-translational mechanisms. The signaling pathways that mediate these changes include the Ras-Raf-mitogen-activated protein (MAP) kinase (MAPK), phosphoinositide 3-kinase-AKT, and signal transducers and activators of transcription (STAT) 3 and STAT5 signal transduction pathways. The STAT families of transcription factors are activated by phosphorylation on a conserved tyrosine residue, leading to dimerization, nuclear translocation, and DNA binding. STAT1, STAT3, and STAT5 are also phosphorylated on a serine residue in their COOH terminus; this phosphorylation it is thought is dispensable for dimerization, nuclear translocation, and DNA binding, but is required for maximal transcriptional activity of some genes.

Several non-small-cell lung cancer cell lines contain constitutively active STAT3. It has been recently shown that STAT3 is activated by several of these EGFR mutants in a genetically defined system. It is not known which of the signal transduction pathways downstream of mutant EGFR are required to mediate its oncogenic properties, however, given the role of STAT3 in a wide range of human malignancies, and the fact that it is activated by EGF in various cell types, it is believed that STAT3 is necessary for the oncogenic effects of somatic mutant EGFRs. It has been reported that STAT3 is activated in fibroblasts expressing mutant EGFRs, as well as in two NSCLC lines with naturally occurring EGFR mutations, and that this activation is required for the transformation and survival of these cells.

The activation of STAT3 often involves a ligand-receptor interaction. STAT3 can be activated by many various cytokines, including interferons, EGF, G-CSF, and interleukin (IL-6) family cytokines. Binding of cytokines to their cognate receptors leads to JAKs phosphorylation, STAT3 dimerization, nuclear translocation, DNA binding, and gene activation (12, 13). In addition, STAT3 phosphorylation can also be induced by cytoplasmic tyrosine kinase, such as Src family kinase (14). It has been reported that elevated EGFR activity and STAT3 activation is positive correlated in many primary tumor specimens and tumor-derived cell lines, including NSCLC, breast cancer, and head and neck carcinomas.

Increased STAT3 activity is observed in lung adenocarcinomas and cell lines expressing mutant EGFRs. Without being bound to any particular theory, STAT3, it is believed, is required by mutant EGFRs and is necessary for its downstream phenotypic effects. Inhibiting STAT3 function in fibroblasts abrogates transformation by mutant EGFR. Unfortunately, targeted therapies, such as TKIs cannot completely abrogate STAT3 activity in NSCLC cell lines.

Previous studies suggest mutant EGFR induces activation of gp130/JAK/STAT3 pathway by means of IL-6 up-regulation. Tumor expression of IL-6 and IL-6 receptor components gp80 and gp130 had been found in NSCLC specimens (20). It has also been observed that increased levels of pro-inflammation cytokines such as IL-6 and IL-8 are also associated with NSCLC tumorigenesis and prognosis. These indicate that IL-6 and its downstream pathway are potential to be the target for patient with NSCLC harboring EGFR mutation. However, the mechanism about IL-6 induction by oncogenic EGFR mutations in NSCLC remains unclear; however, it is thought that NF-kB and STAT3 signaling are responsible for regulating IL-6 autocrine in lung cancer.

According to one aspect of the invention anti EGF antibodies are used for treating patients suffering from cancers driven by deregulated Human Epidermal Growth Factor Receptor 1 (HER1/Human EGFR) by administering to a patient in need of such treatment a flexible and active regimen for combining a tyrosine kinase inhibitor (TKI) and anti-EGF antibodies according to the invention for inhibition of the pathway activated by EGF-EGFR binding (mAb), wherein the TKI is administered according to a continuous regimen based on an average daily dose in the range of about 10 to 250 mg and the EGF TPI according to the invention is co-administered according to a dosing regimen achieving a therapeutic effective amount repeated thrice, twice or once a week, once in two weeks, once in three weeks or at least once monthly.

According to a further aspect of the invention anti EGF antibodies generated by vaccination of patients suffering from cancers driven by deregulated Human Epidermal Growth Factor Receptor (HER1/Human EGFR) by administering to a patient in need of such treatment a flexible and active regimen for combining a tyrosine kinase inhibitor (TKI) and a vaccine producing an immune response to EGF, wherein the TKI is administered according to a continuous regimen based on an average daily dose in the range of about 10 to 250 mg and the vaccine according to the invention is co-administered according to a dosing regimen achieving a therapeutic effective amount repeated thrice, twice or once a week, once in two weeks, once in three weeks or at least once monthly.

According to a further aspect of the invention it was observed that the effect of anti EGF antibodies at physiological concentrations on phosphorylation of EGFR, Akt and ERK1/2 are at least as significant as the effect of TKIs, such as gefitinib, on these signaling molecules. It is within the scope of the invention that combination treatment of the anti EGF antibodies and TKIs, such as gefitinib, shows unexpected and significant synergistic effect for pEGFR, pAkt, pERK1/2 inhibition. Without being bound to any particular theory, it is thought that administration of gefitinib to EGFR mutated cells leads to activation of STAT3, considered as first step in acquisition of resistance to therapy and that the combination of anti EGF antibodies according to the invention inhibits such activation.

Conventional TKI therapies, such as gefitinib and erlotinib as discussed above, are indicated for administration to patients in a daily regimen for the treatment of cancer at dosages intended to block activation of EGFR. However, also as discussed above, patients frequently develop a resistance to this treatment. The present disclosure is based on the Applicants' surprising discovery that a dosing regimen of a TKI in combination with the active or passive use of anti-EGF antibodies may be administered to resistant patients to overcome their resistance, or to patients who are not responsive to TKI therapy to overcome their non-responsiveness (both indications are hereinafter included in the term "resistant" when used to describe individuals with cancer). This combination dosing schedule is surprisingly well-tolerated. Further embodiments of the present invention are based on the inventor's identification of STAT3 metabolic pathway as being responsible for this resistance or non-responsiveness.

The methods of the present invention are not limited to the treatment of NSLC. Instead, it will be readily understood that the bio-molecular pathways addressed and the TKI resistance obviated by the methods of the present invention may find application in the treatment of other disease conditions; any disease condition in which treatment with a TKI would result in a beneficial result for a patient under treatment. "Beneficial results" may include, but are in no way limited to, lessening the severity of the disease condition, preventing the disease condition from worsening, curing the disease condition and prolonging a patient's life or life expectancy. These disease conditions may relate to or be modulated by EGFR or any other kinase that may be clinically affected with the methods of the present invention.

More specifically, the inventor's experimental studies as set forth in the following examples have demonstrated clinical activity of TKIs at the daily dosing regimens in molecular studies on these tumors demonstrated effective inhibition of the EGFR signaling cascade. The examples confirmed that the molecular studies properly reflected the behavior of these TKIs as observed in other model systems. The disclosure also surprisingly demonstrates that TKIs in combination with anti-EGF antibodies, which are passively administered or actively produced by the administration of a vaccine producing such antibodies, can inhibit tumor growth effectively in molecular models—even in tumors that demonstrated a resistance to conventional TKI therapy.

In one illustrative embodiment the anti-EGF antibodies used in the pre-clinical studies are actively produced by immunizations with a rEGF-rP64k conjugate, CIMAvax-EGF vaccine as described in Manufacturing Process Development for an Epidermal Growth Factor-Based Cancer Vaccine, Rodriguez et al., (Supplement to Biopharm International October 2008, the contents of which are incorporated in their entirety by reference) formulated with Montanide adjuvant. It is contemplated within the scope of the disclosure that other vaccine formulations that produce an immune response to EGF or EGFR may be used. It is also within the Scope of the disclosure that vaccines producing an immune response to other growth factors or their receptors may also be used. In particular, immunogenic proteins as set forth in WO2013/076580 and WO2014/140894, the content of each incorporated in their entirety by reference, may be used to produce anti-EGF antibodies according to the disclosure.

While not wishing to be bound by any theory, it is believed that these suppression of the STAT3 metabolic pathway, which is required for stimulation of the cell signaling pathways responsible for cell proliferation, it is also believed that the additional inhibition of the STAT3 by the combination dosing regimen of the present invention is effective in inhibiting or down-regulating this cell signaling. Moreover, even those patients who are resistant to conventional TKI therapy may obtain a beneficial, anti-tumor effect by the combination dosing regimen of the present invention, because STAT3 is inhibited as well. The combination therapy of the present disclosure may be associated with hindrance of the disease condition where conventional TKI therapies failed. The methods of the present invention, therefore, can overcome resistance or non-responsiveness to TKI therapy by operating differently than conventional methods at the cellular and molecular level.

In particular embodiments, combination dosage of a TKI with anti-EGF antibodies may be effective in treating cancer, and especially lung, breast and prostate cancer, in an individual who is resistant to conventional TKI therapy. Other forms of cancer that may be treated with the methods of the present invention include, but are in no way limited to gastric, colorectal, and ovarian cancer, as well as glioblastoma tumors. Each of these forms of cancer demonstrates significant EGFR expression, making them suitable targets for treatment in accordance with the methods of the present invention.

TKIs suitable for use in accordance with the methods of the present invention may include, but are in no way limited to, TKIs that are generally known for use in the treatment of cancer, and, specifically, breast, lung and prostate cancer. By way of example, such TKIs may include, but are not limited to IRESSA® and TARCEVA®, as described above, but may further include CI1033 (available from Pfizer Inc.), PKI166 (available from Novartis AG), GW2016 (available from GlaxoSmithKline), EKB569 (available from Wyeth), IMC-C225 (available from ImClone Systems Inc. and Bristol-Myers Squibb Co.), and pharmaceutically acceptable salts or equivalents of the same; each of the latter group currently at the Phase I or Phase II clinical trial stage, all of which are included within the term "kinase inhibitors" or "TKIs."

In particular, several TKIs have been found to have effective antitumor activity and have been approved or are in clinical trials. Examples of such include, but are not limited to Zactima (ZD6474), Iressa® (gefitinib) and Tarceva® (erlotinib), imatinib mesylate (STI571; Gleevec), erlotinib (OSI-1774; Tarceva®), canertinib (CI 1033), semaxinib (SU5416), vatalanib (PTK787/ZK222584), sorafenib (BAY 43-9006), sutent (SU11248) and leflunomide (SU101).

The efficacy of a given treatment for cancer can be determined by the skilled clinician. However, a treatment is considered "effective treatment," as the term is used herein, if any one or all of the signs or symptoms of e.g., a tumor are altered in a beneficial manner or other clinically accepted symptoms are improved, or even ameliorated, e.g., by at least 10% following treatment with an agent as described herein. Efficacy can also be measured by a failure of an individual to worsen as assessed by hospitalization or need for medical interventions (i.e., progression of the disease is halted). Methods of measuring these indicators are known to those of skill in the art and/or described herein.

An effective amount for the treatment of a disease means that amount which, when administered to a mammal in need thereof, is sufficient to result in effective treatment as that term is defined herein, for that disease. Efficacy of an agent can be determined by assessing physical indicators of, for example cancer, e.g., tumor size, tumor mass, tumor density, angiogenesis, tumor growth rate, etc. In addition, efficacy of an agent can be measured by a decrease in circulating MIC peptides or fragments thereof in a subject being treated with an agent comprising an antibody or antigen-binding portion thereof as described herein or a nucleic acid encoding an antibody or antigen-binding portion thereof as described herein.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

This invention is further illustrated by the following examples, which should not be construed as limiting.

Example I: Assessment of Anti EGF on Inhibition of EGF/EGFR Pathway with WB as Endpoint Objectives: To compare, in PC9 cell line from NSCLC patients, effect of anti-EGF antibodies to Gefitinib on inhibition of the pathway activated by EGF-EGFR binding. To assess whether, in same cell line, combination of anti EGF and Gefitinib would have a synergistic effect.

Materials and Methods for Testing Activation by Western Blotting (WB) Methodology:

The PC9 cell line carries a deletion in exon 19 making this cell line sensitive to TKI's. It represents a model for the EGFR Mutated segment of the NSCLC patient cohort receiving first-line TKI treatment.

All tissue culture materials for these experiments were obtained from Biological Industries (Kibbutz Beit Haemek, Israel) or Invitrogen (Paisley, Scotland, UK). The PC9 cell line was kindly provided by F. Hoffman-La Roche Ltd (Basel, Switzerland). Cells were maintained in RPMI medium supplemented with 10% fetal bovine serum (FBS), 50 µg/mL penicillin-streptomycin and 2 mM L-Glutamine. Cells are grown in a humidified atmosphere with 5% CO2 at 37° C.

Anti-EGF antibodies used in this project were derived from an immunization study in monkeys that received 4 immunizations of the rEGF-rP64k conjugate CIMAvax-EGF vaccine formulated with Montanide adjuvant (Ab1), as described above. Serum was treated on Mellon gel to remove contaminants such as complement. This purification was conducted at Scotia, Aberdeen, UK. The Elisa titer is: approximately 1/60000

Experiment 1: In a typical standard experiment, five T-75 flasks of the cell line under study were cultured to approximately 70% confluence, washed twice with PBS and grown o/n in serum-free medium. The serum-starved cells were then washed again and treated as follows:

For first experiments anti EGF dilutions ware tested at 1 to 20, 1 to 10 and one to 5 when alone or when combined with gefitinib. Gefitinib was used at concentration of about 40 nano-Molar Medium, EGF and antibody or gefitinib or both anti-EGF and gefitinib were mixed and pre-incubated at about 37° C. for about 10 min prior to addition to the cells. Treatment was for about 15 minutes.

Experiment 2: In a second experiment anti-EGF was tested only at 1 to 2 dilution. Gefitinib was at a concentration of 0.5 micro molar. Treatment was prolonged to about 2 hours in this experiment.

After treatment, in experiments 1 and 2 the cultures were washed with PBS and lysed in protease and phosphatase inhibitors-containing lysis buffer. Equal amounts of protein were loaded onto an SDS-PAGE gel, transferred to a membrane and blotted with antibodies against EGFR, p-EGFR, ERK1/2, p-ERK1/2, Akt, p-Akt, STAT 3 and pSTAT-3. The intensity of the bands was determined using the ImageJ program and then submitted to two-step normalization. First, the intensity of the phosphorylated band was divided by the intensity of the band corresponding to the total protein in the same sample. This value was then divided by the value obtained in the EGF-treated cells for the same protein. Both EGF and anti-EGF antibodies, which used in this project were derived from an immunization study in monkeys that received 4 immunizations of the rEGF-rP64k conjugate CIMAvax-EGF vaccine formulated with Montanide adjuvant. The vaccine and resulting anti-EGF antibodies were provided by Bioven (Europe) Ltd, Cruikshank Building North, Aberdeen Biotechnology, Craibstone Aberdeen, U.K. Scotland. Antibodies for Western blotting were purchased from Santa Cruz Biotechnologies (Palo Alto, CA). The raw data from the experimental project are reflected in FIG. 1.

Figure 2:
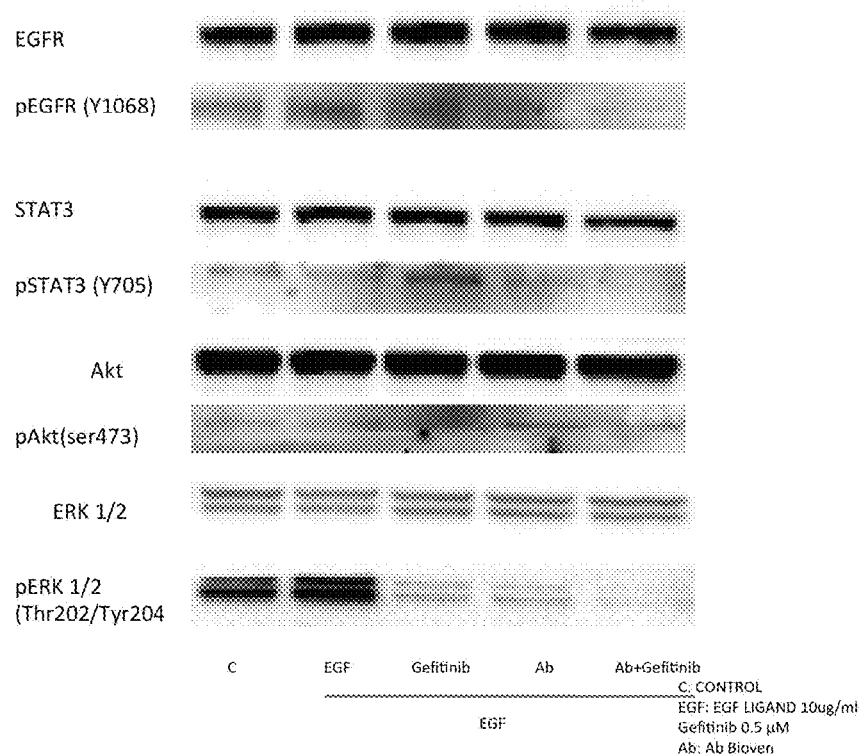
FIG. 2 shows a SDS-PAGE WB displaying that a combination treatment according to the disclosure reversed activation of STAT 3 by Gefitinib suggesting that combination treatment could be beneficial in EGFR mutated NSCLC patients.

Results of Experiment 1 and 2 (2 hours incubation): The results of the second experiment are shown in FIG. 2 presented hereunder with following observations: The results in experiment 1, depicted in FIG. 1, confirm the effects seen that prolonged incubation has significant effect on phosphorylation of STAT3. It was also observed that the effect of anti EGF on phosphorylation of EGFR, Akt and ERK1/2 are at least as significant as the effect of gefitinib on these signaling molecules. It was also concluded that combination treatment of the anti EGF and Gefitinib shows additional effect for pEGFR, pAkt, pERK1/2 inhibition. Without being bound by any particular theory, it is thought that administration of gefitinib to EGFR mutated cells leads to activation of STAT3, considered as first step in acquisition of resistance to therapy. Based upon the experimental exposure of PC9 cells to anti-EGF, it appears that anti-EGF does not activate STAT3, on the contrary, but rather has some limited inhibitory effect. It was further concluded that unexpectantly, the combination treatment did completely reverse activation of STAT3 by gefitinib suggesting that combination treatment could be beneficial in EGFR mutated NSCLC patients as evidenced in FIG. 2.

Figure 3:
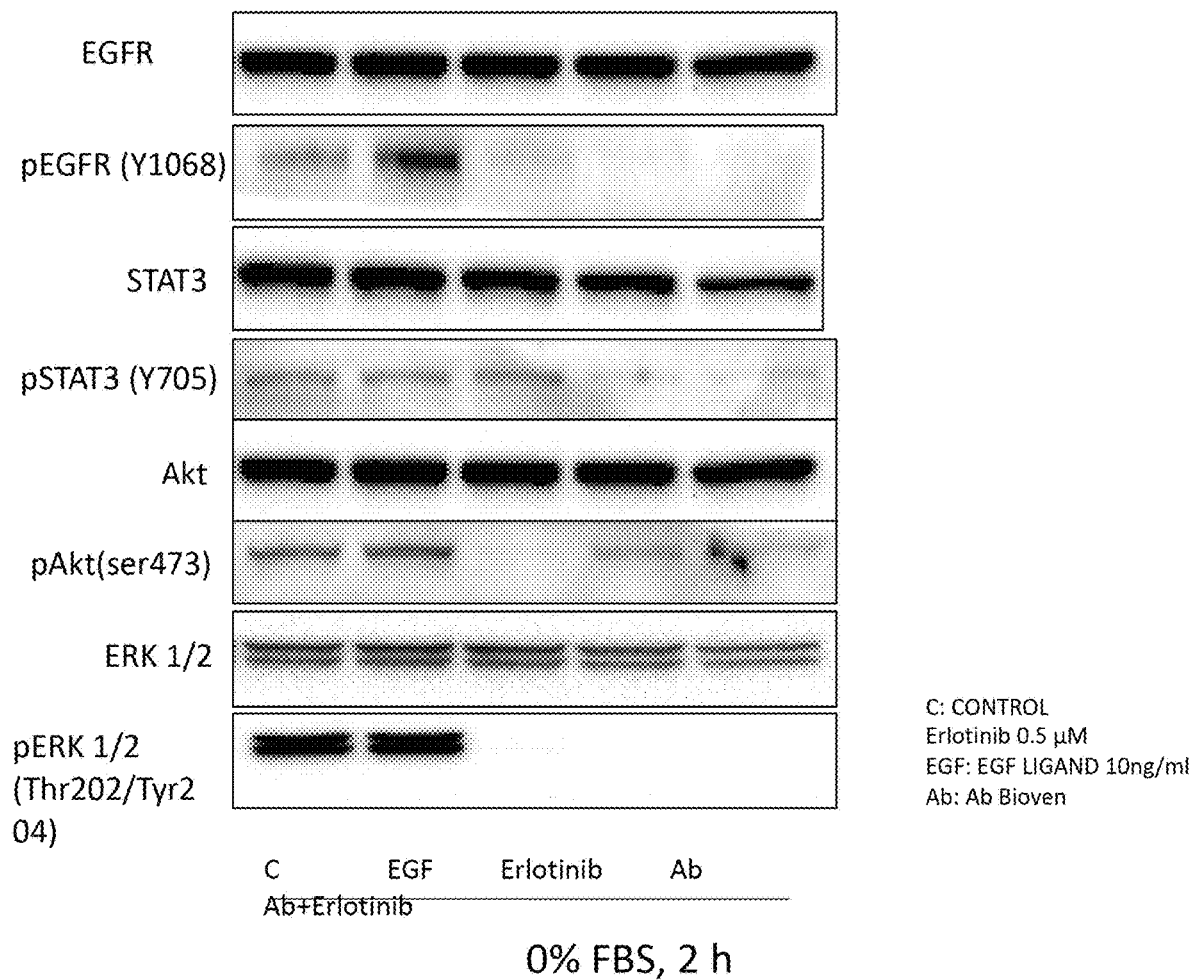
FIG. 3 shows a SDS-PAGE WB displaying the results of anti-EGF antibodies that were tested only at 1 to 2 dilution. Erlotinib was at a concentration of 0.5 micro molar.
Figure 4:
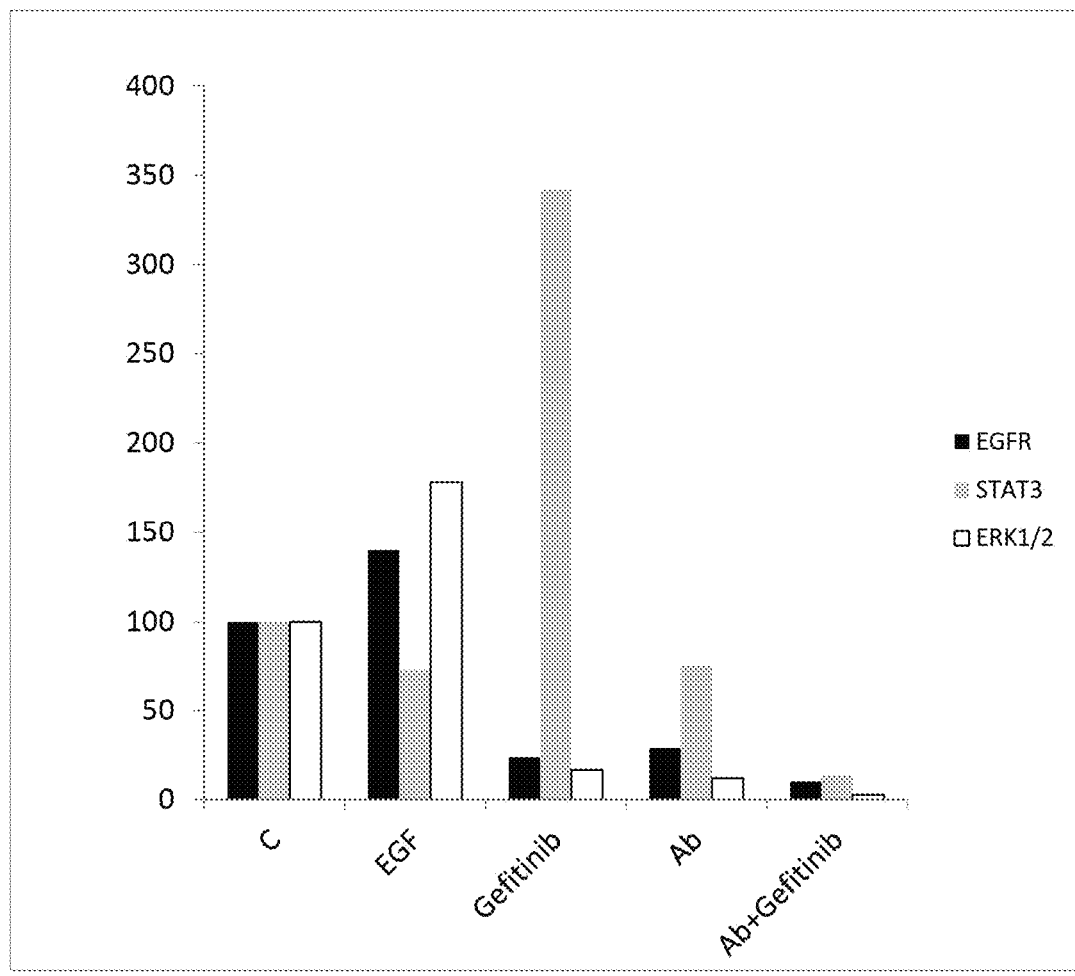
FIG. 4 depicts a comparison of levels of EGFR, STAT3 and ERK1/2 after treatment with Gefitinib, anti EGF antibodies and a combination of both Gefitinib, anti EGF antibodies.
Figure 5A:
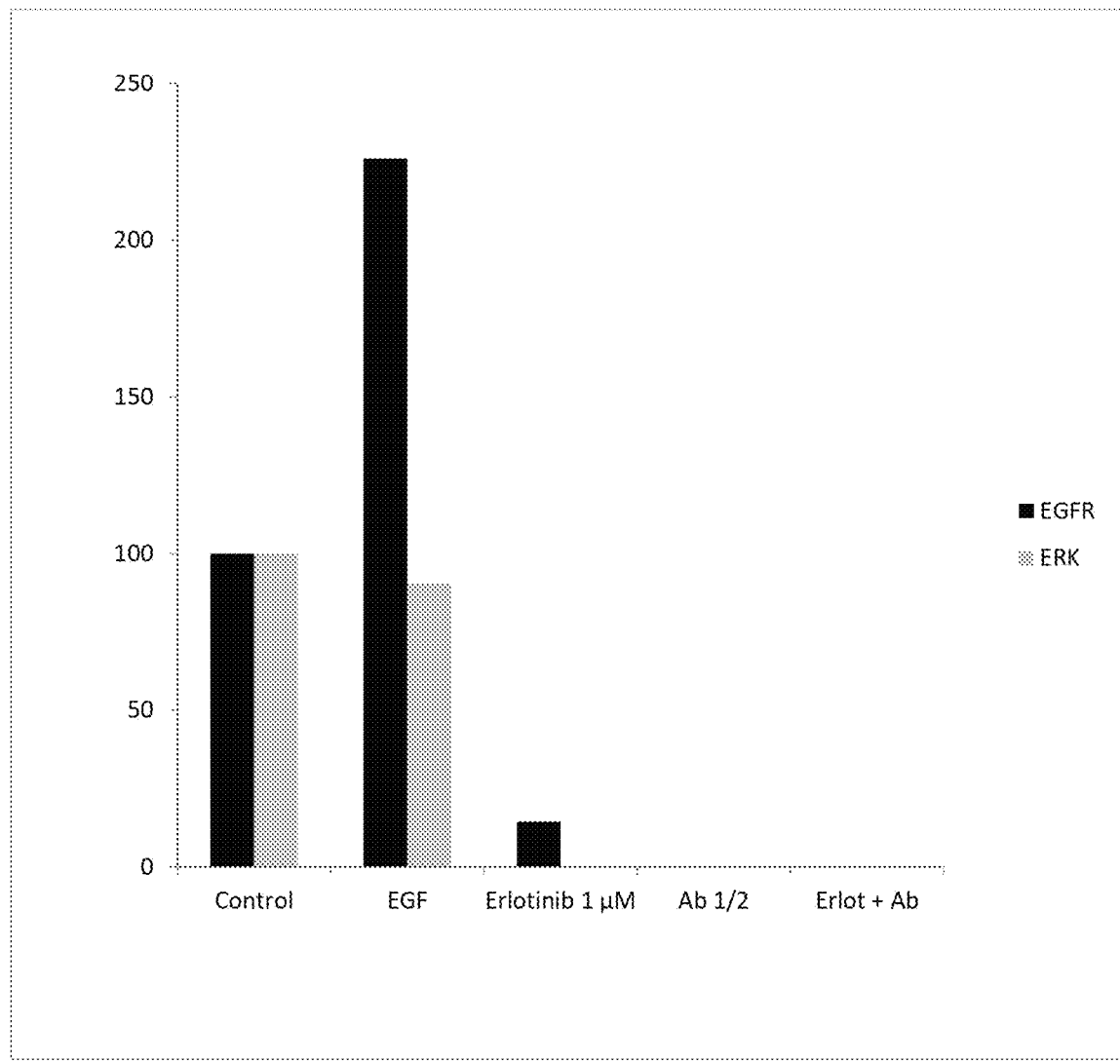
FIGS. 5A and 5B depict a comparison of levels of EGFR, STAT3 and ERK1/2 after treatment with Erlotinib, anti EGF antibodies and a combination of both Erlotinib, anti EGF antibodies, which are summarized in table 1.
Figure 5B:
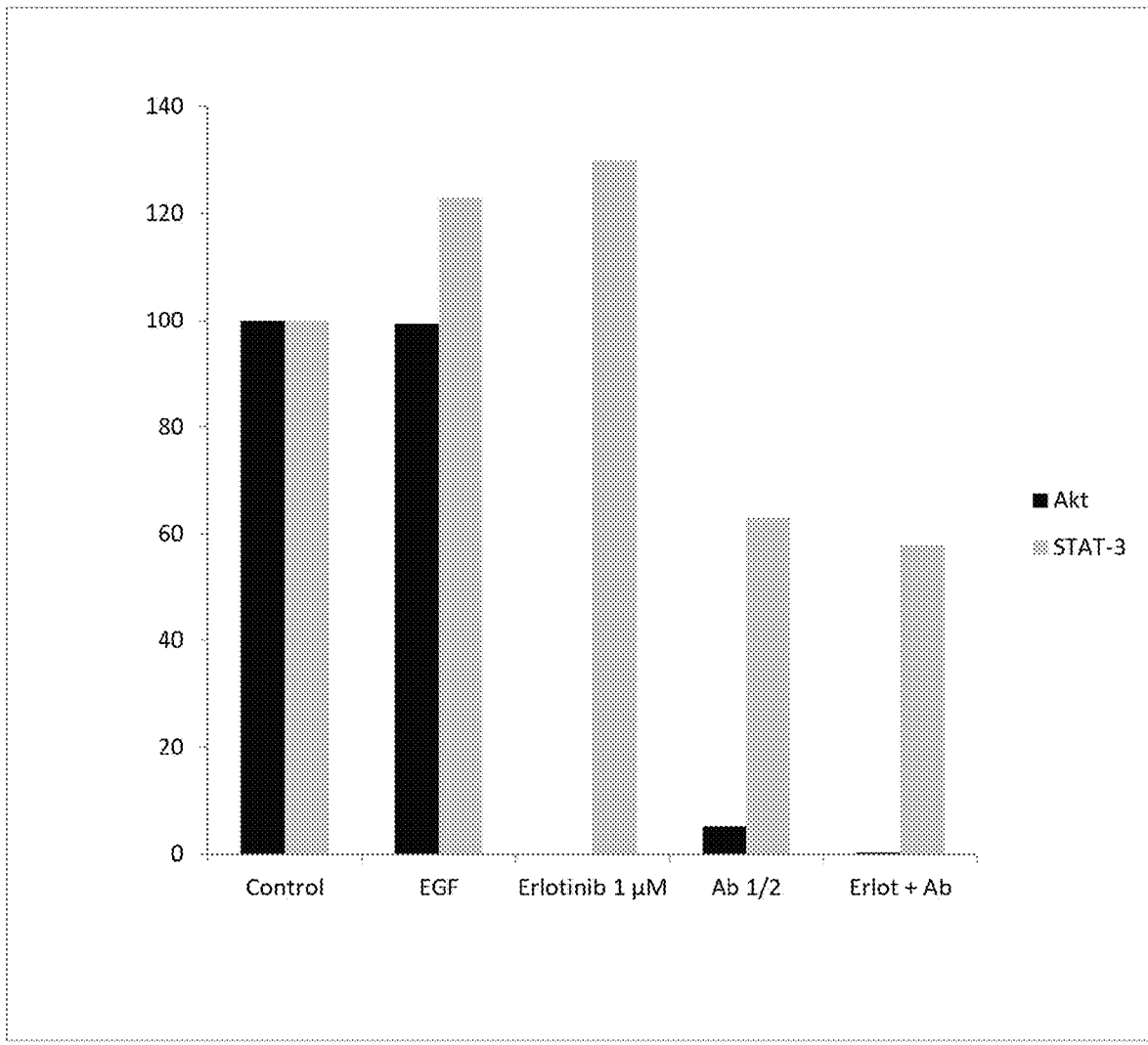

Experiment 3: In a third experiment anti-EGF was tested only at 1 to 2 dilution. Erlotinib was at a concentration of 0.5 micro molar. Treatment was prolonged to about 2 hours in this experiment. After treatment, the cultures were washed with PBS and lysed in protease and phosphatase inhibitors-containing lysis buffer. Equal amounts of protein were loaded onto an SDS-PAGE gel, transferred to a membrane and blotted with antibodies against EGFR, p-EGFR, ERK1/2, p-ERK1/2, Akt, p-Akt, STAT 3 and pSTAT-3. The intensity of the bands was determined using the ImageJ program and then submitted to two-step normalization. First, the intensity of the phosphorylated band was divided by the intensity of the band corresponding to the total protein in the same sample. This value was then divided by the value obtained in the EGF-treated cells for the same protein. Both EGF and anti-EGF were provided by Bioven. Antibodies for Western blotting were purchased from Santa Cruz Biotechnologies (Palo Alto, CA). The raw data from the experimental project are reflected in FIG. 3 and are summarized in Table 1 below:

TABLE 1

|  | EGFR | ERK | Akt | STAT-3 |  |
|---|---|---|---|---|---|
| Control | 100 | 100 | 100 | 100 | 0% FBS |
| EGF | 226 | 90.8 | 99.4 | 123 |  |
| Erlotinib 1 µM | 14.3 | 0 | 0 | 130 |  |
| Ab ½ | 0 | 0.3 | 5.2 | 63 |  |
| Erlot + Ab | 0 | 0 | 0.3 | 58 |  |

Example 2: Assessment of Anti EGF (Single-Agent and Combined with Gefitinib) on Inhibition of EGF/EGFR Pathways with WB as Endpoint A further experiment was undertaken to compare, in the PC9 NSCLC cell line, the effects of anti-EGF antibodies and gefitinib and erlotinib on the inhibition of the pathways activated by EGF-EGFR binding to assess whether, in the same cell line, the combination of anti EGF and gefitinib or erlotinib is superior to single-agent treatment. The experiment was designed to compare, in a PC9 cell line resistant to gefitinib carrying the T790M mutation (PC9-GR4), the effects of anti-EGF antibodies and TAGRISSO™ AstraZeneca (AZD9291), which is approved by the US FDA for patients with EGFR T790M mutation-positive metastatic non-small cell lung cancer, on the inhibition of the pathways activated by EGF-EGFR binding and to assess whether, in the same cell line, the combination of anti EGF and AZD9291 is superior to single-agent treatments Materials and Methods for Testing Activation by Western Blotting (WB) Methodology Cell Lines In the conduct of this study PC9-derived cell lines that are resistant to TKIs were utilized. The parental PC9 are NSCLC-derived cells that harbor a 15 bp deletion in exon 19 and are extremely sensitive to gefitinib and foretinib (IC50 in the nM range). They represent a model for the EGFR Mutated segment of the NSCLC patient population receiving first-line TKI treatment. We treated PC9 cells with increasing concentrations of erlotinib and gefitinib over a period of 2 months and obtained 6 different lines (PC9-ER and GR1 to GR5) that were resistant to both gefitinib and erlotinib (IC50 around 5-10 Similarly to patients, none of the 6 lines lost the sensitizing mutation (15 bp deletion) but the resistant mutation T790M were present in two of them. These two cell lines (PC9-GR1 and GR4) are sensitive to the new generation EGFR TKI developed by Astra Zeneca (AZD9291) that can also bind to the T790M EGFR mutated protein.

Materials

All tissue culture materials were obtained from Biological Industries (Kibbutz Beit Haemek, Israel) or Invitrogen (Paisley, Scotland, UK). The PC9 cell line was kindly provided by F. Hoffman-La Roche Ltd (Basel, Switzerland), under the authorization of Dr. Mayumi Ono, the investigator who established the cell line. Cells were cultured in RPMI medium supplemented with 10% fetal bovine serum (FBS), 50 µg/mL penicillin-streptomycin and 2 mM L-Glutamine and maintained in a humidified atmosphere with 5% CO2 at 37° C. Bioven provided the anti-EGF antibodies. Anti-EGF antibodies used in this project were derived from an immunization study in monkeys that received 4 immunizations of the rEGF-rP64k conjugate formulated with Montanide adjuvant. Serum was treated on Mellon gel to remove contaminants such as complement. This purification step was conducted at Scotia, Aberdeen, UK. The Elisa titer was: 1/60000. Gefitinib was purchased from Selleck Chemicals (Houston, TX). EGF and antibodies for Western blotting were purchased from Santa Cruz Biotechnologies (Palo Alto, CA).

Treatments

In experiments #1 and #2, nine T-75 flasks of the PC9 cell line were cultured to 70% confluence, washed twice with PBS and grown o/n in serum-free medium. The serum-starved cells were then washed again (×2) and treated with the anti-EGF (single agent and combined with gefitinib) pre-incubated at 37° C. for 10 min with serum-free medium containing 10 ng EGF/mL. The incubation time of the cells with the drugs was about 10 min; gefitinib concentration was 40 nM in all cases, while the antibody dilutions ranged from 1/20 to 1/2. Subsequently, three kind of experiments were performed:

A. Serum Starvation: In experiments "with 24 h serum starvation", five T-75 flasks of the PC9 cell line were submitted to serum deprivation (o/n), washed (×2) and treated with the anti-EGF (single agent and combined with gefitinib) pre-incubated at 37° C. for 10 min with serum-free medium containing 10 ng EGF/mL. The incubation time of the cells with the drugs was 15 min or 2 h; gefitinib was tested at different concentrations, AZD9291 concentration was always 0.5 erlotinib 1 µM and anti-EGF was added at 1/2 dilution;

B. Serum Starvation/Drug Treatment: In experiments "with 24 h serum starvation and drug treatment", five T-75 flasks of the PC9 cell line were simultaneously submitted to serum deprivation and treated with gefitinib, the antibody or both for 24 h. The following day cells were treated with the anti-EGF (single agent and combined with gefitinib) pre-incubated at 37° C. for 10 min with serum-free medium containing 10 ng EGF/mL. The additional incubation time of the cells with the drugs was 2 h; gefitinib was tested at 0.5 µM; and C. Non-Standard Conditions: In experiments "under non-standard conditions", PC9 (4 flasks) cells were not submitted to serum starvation and activation with fetal bovine serum instead of human EGF was employed. They were washed with PBS (×2), drugs were added in medium containing 10% FBS and incubated for 2 hours. Again, gefitinib and AZD9291 concentration was 0.5 µM, erlotinib 1 µM and anti-EGF was added at 1/2 dilution Western Blotting After treatment, the cultures were washed with PBS and lysed in protease and phosphatase inhibitors-containing lysis buffer. Equal amounts of protein were loaded onto an SDS-PAGE gel, transferred to a membrane and blotted with antibodies against EGFR, p-EGFR, ERK1/2, p-ERK1/2, Akt, p-Akt, STAT 3 and pSTAT-3. The intensity of the bands was determined using the ImageJ program and then submitted to two-step normalization. First, the intensity of the phosphorylated band was divided by the intensity of the band corresponding to the total protein in the same sample. This value was then divided by the value obtained in the EGF-treated cells for the same protein.

Results

Gefitinib and Anti-EGF in PC9 Cells (15 Min, 40 nM Gefitinib)

Figure 6A:
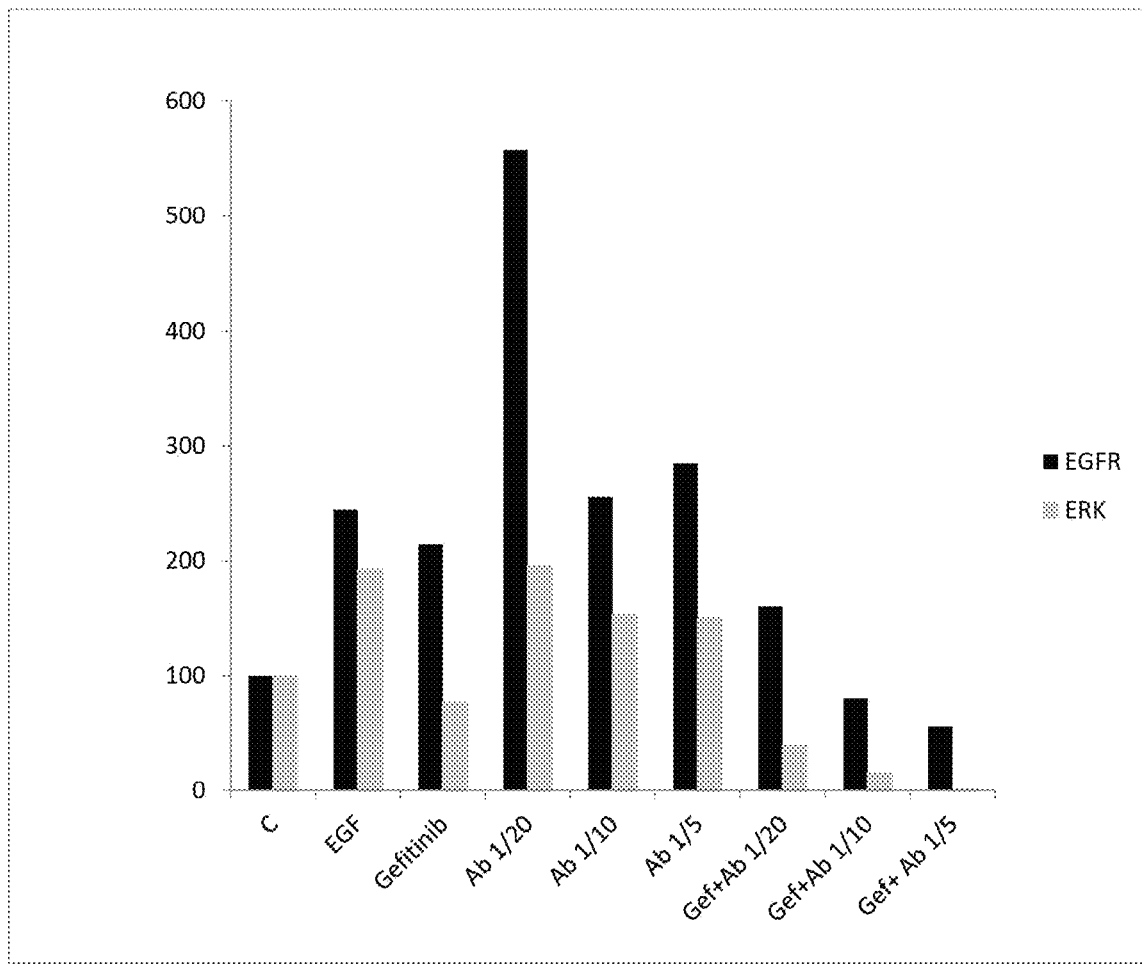
FIGS. 6A, 6B and 6C depict the results of the combination of gefitinib+anti-EGFR, the phosphorylation of the four proteins was inhibited.
Figure 6B:
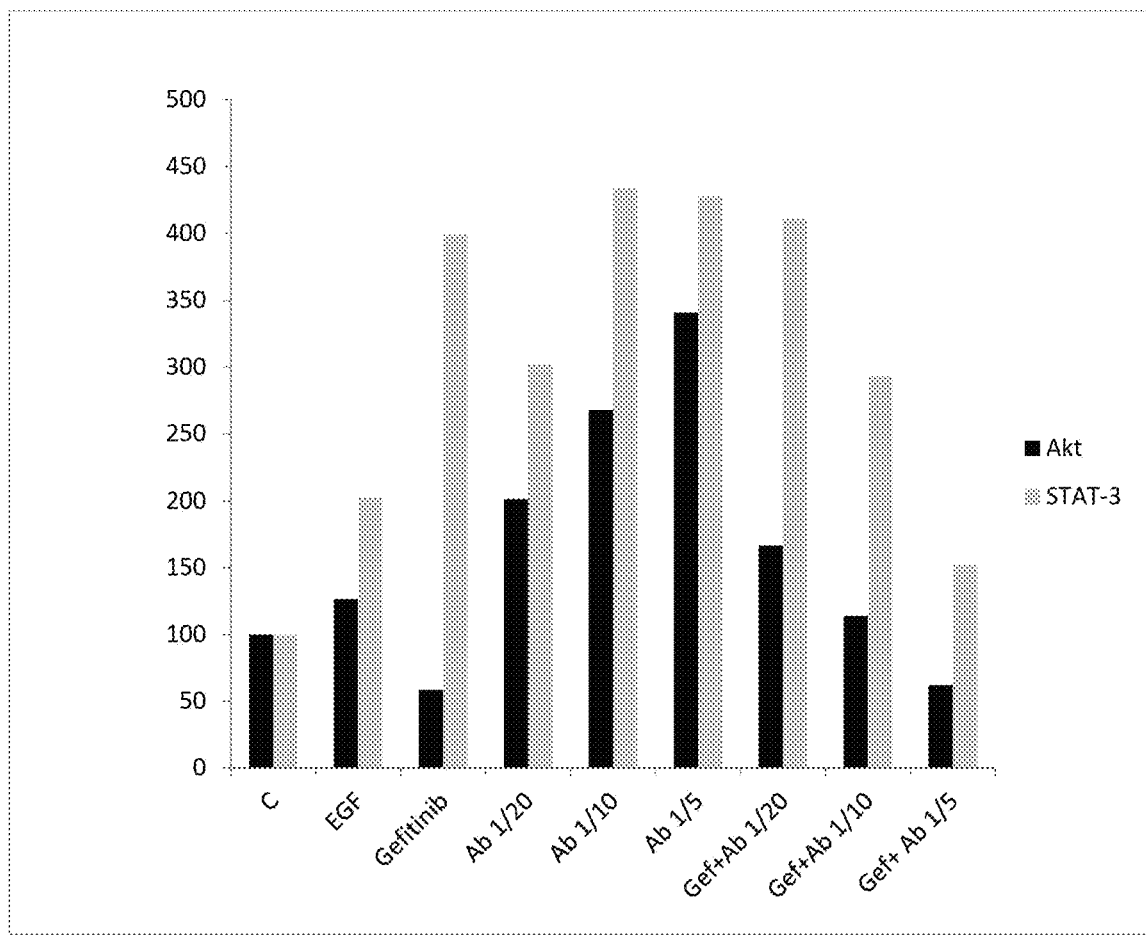
Figure 6C:
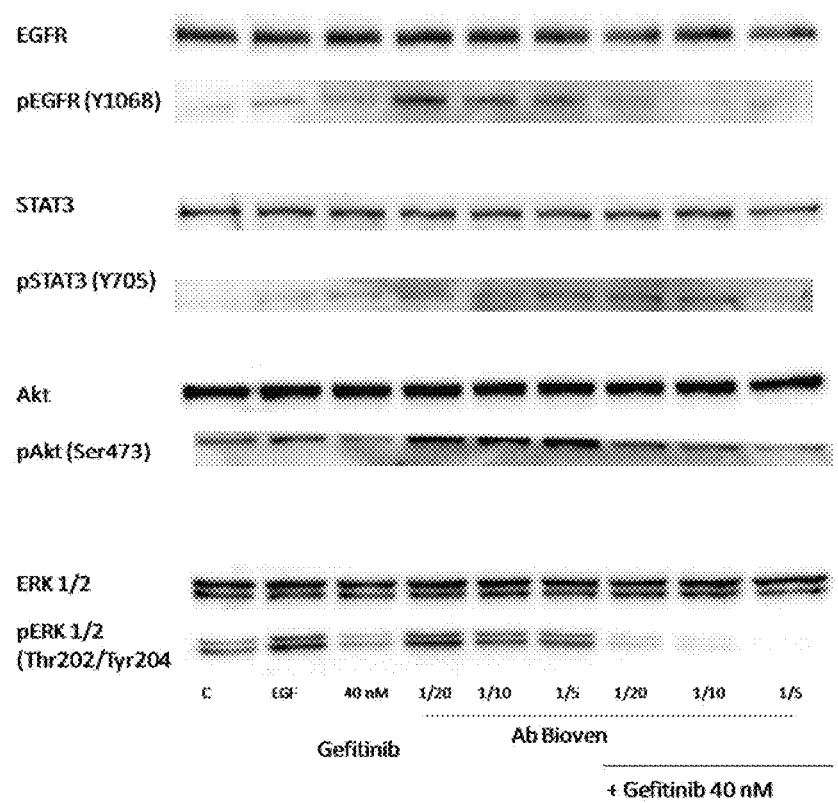

The results of the first experiment (Western blotting and quantification of the phosphorylated proteins) are presented in FIGS. 6A, 6B and 6C. In this first experiment it was apparent that gefitinib inhibited EGFR, Erk and Akt phosphorylation but activated STAT3. The Bioven anti-EGF antibodies appeared to activate EGFR (the activation was only at the under-physiological 1/20 and 1/10 dilutions. At 1/5 there was no activation) and Akt but inhibited Erk and STAT3. In the combination gefitinib+anti-EGFR, the phosphorylation of the four proteins was inhibited. In light of the data shown in FIGS. 6A, 6B and 6C, combination treatment was superior to the single-agent treatments Second Experiment (15 Min, 0.5 µM Gefitinib)

Figure 7A:
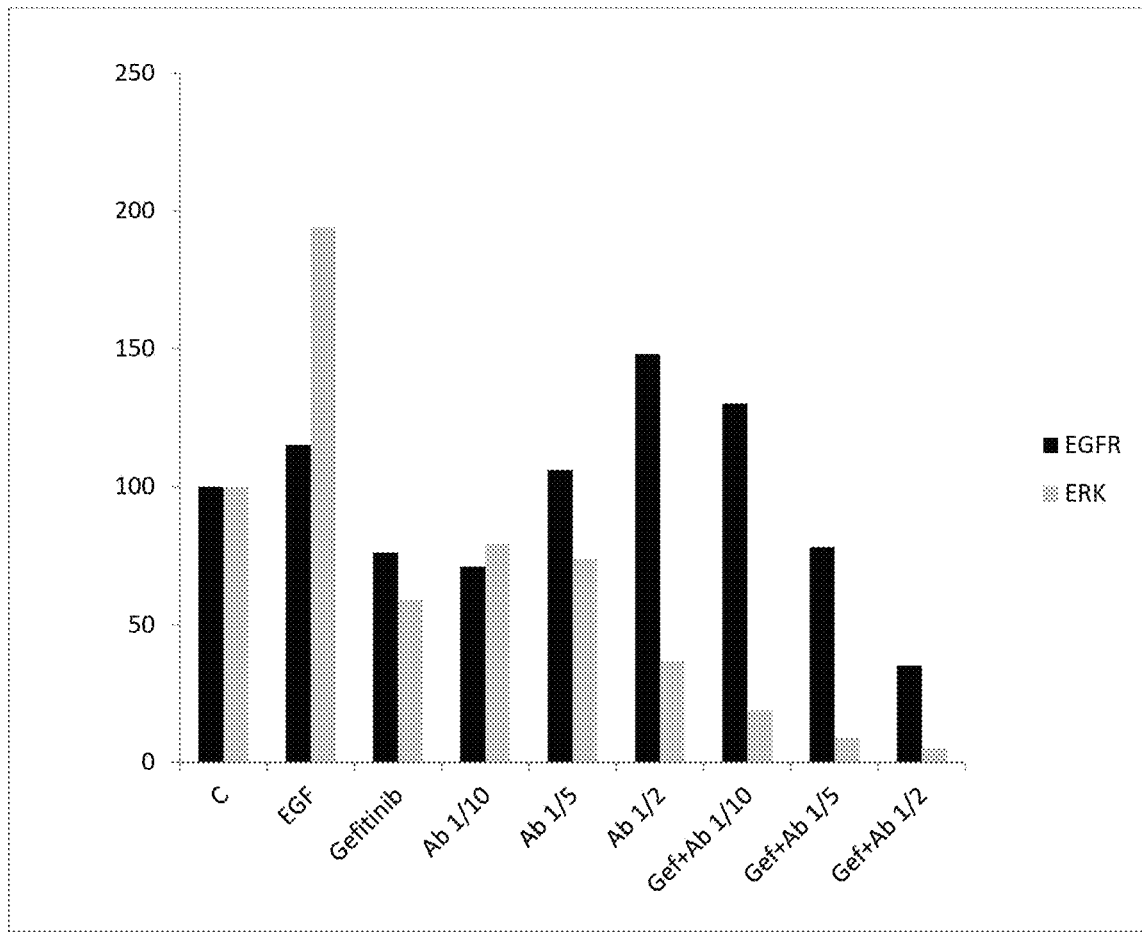
FIGS. 7A and 7B depict the results of the combination of gefitinib and an increased concentration of anti-EGF antibodies.
Figure 7B:
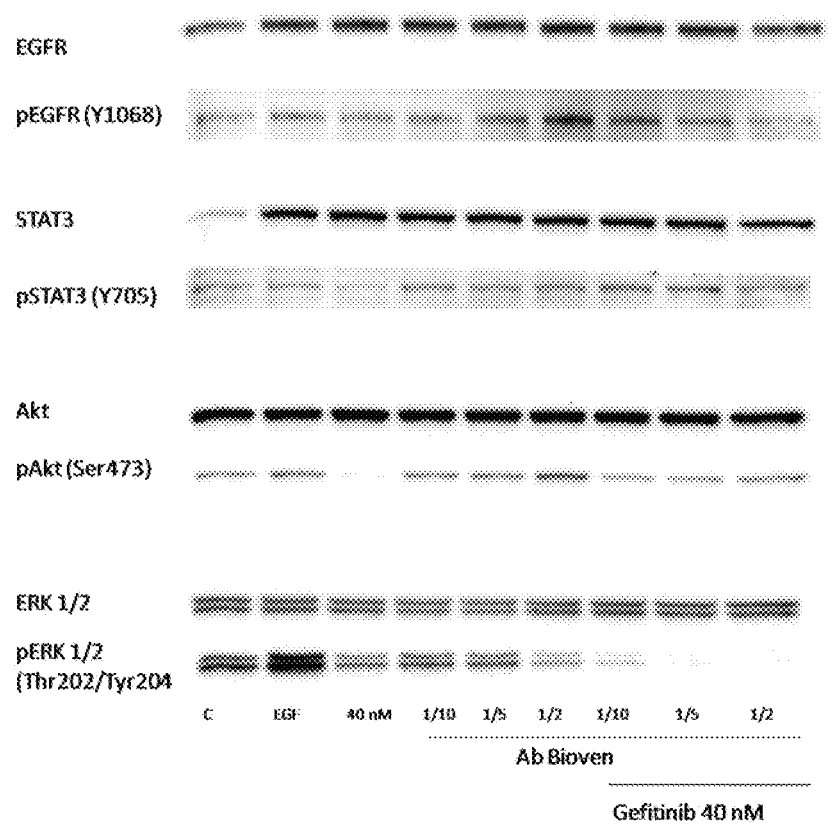

This second experiment was performed as a confirmation of the findings of the first experiment raising the concentration of anti-EGF antibody. In the case of Akt and STAT-3 results were not discernable due to an experimental problem with the gefitinib single agent lane and the quantification is not presented. The second experiment confirmed the results obtained for EGFR and Erk in the first experiment, and the superiority of the combination anti-EGF plus gefitinib, in light of the data shown in FIGS. 7A and 7B.

Third Set of Experiments (2 h)

Figure 8A:
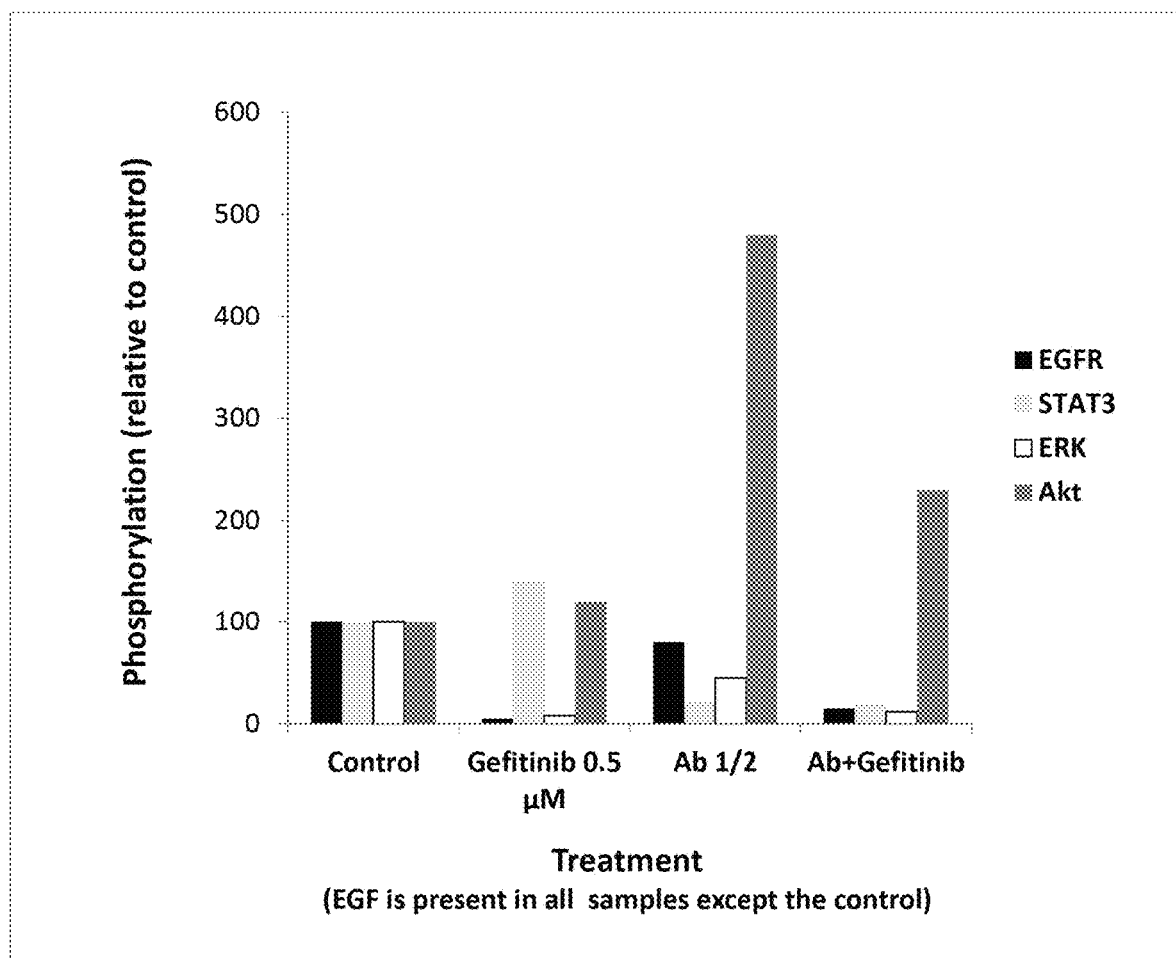
FIGS. 8A and 8B depict the raw data from combining anti-EGF and gefitinib, showing that Erk, STAT3, and EGFR were almost completely inactivated.
Figure 8B:
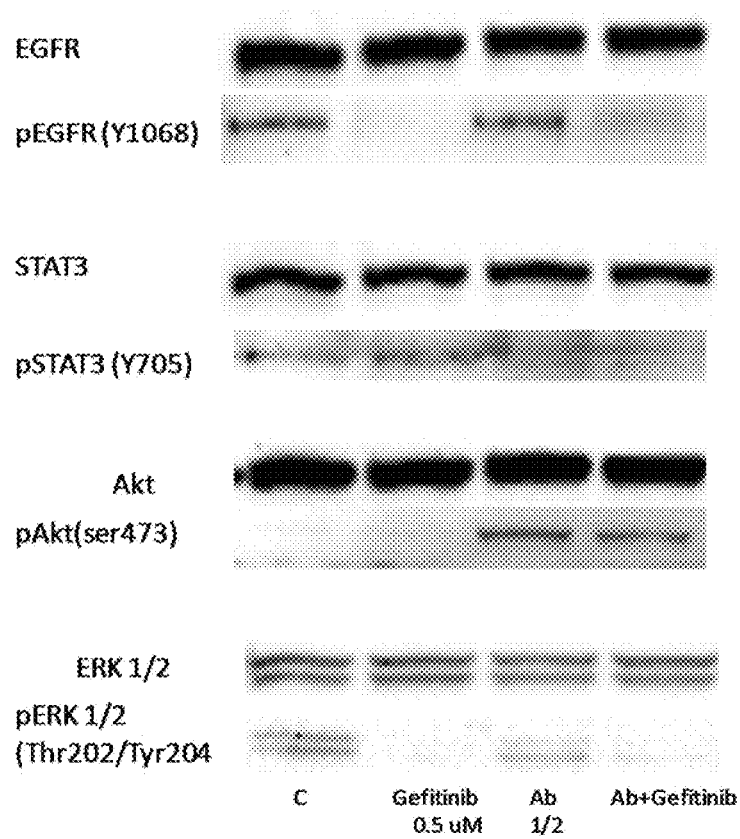

A third set of experiments was performed using 2 h incubation times. A first assay was carried out under "nonstandard conditions", with cells that were not serum-starved and not induced by EGF. Incubation time with the drugs was much longer than in previous experiments (2 h) and gefitinib concentration was raised to 0.5 µM. It was apparent that gefitinib single-agent inactivated EGFR and Erk but activated STAT-3. Under these conditions, the Bioven anti-EGF antibodies inactivated Erk, STAT-3, and EGFR (to a lesser extent) but activated Akt. When combining Bioven anti-EGF antibodies and gefitinib, Erk, STAT3, and EGFR were almost completely inactivated, in light of the data shown FIGS. 8A and 8B.

Third Set of Experiments (Serum Starvation Conditions)

Figure 9A:
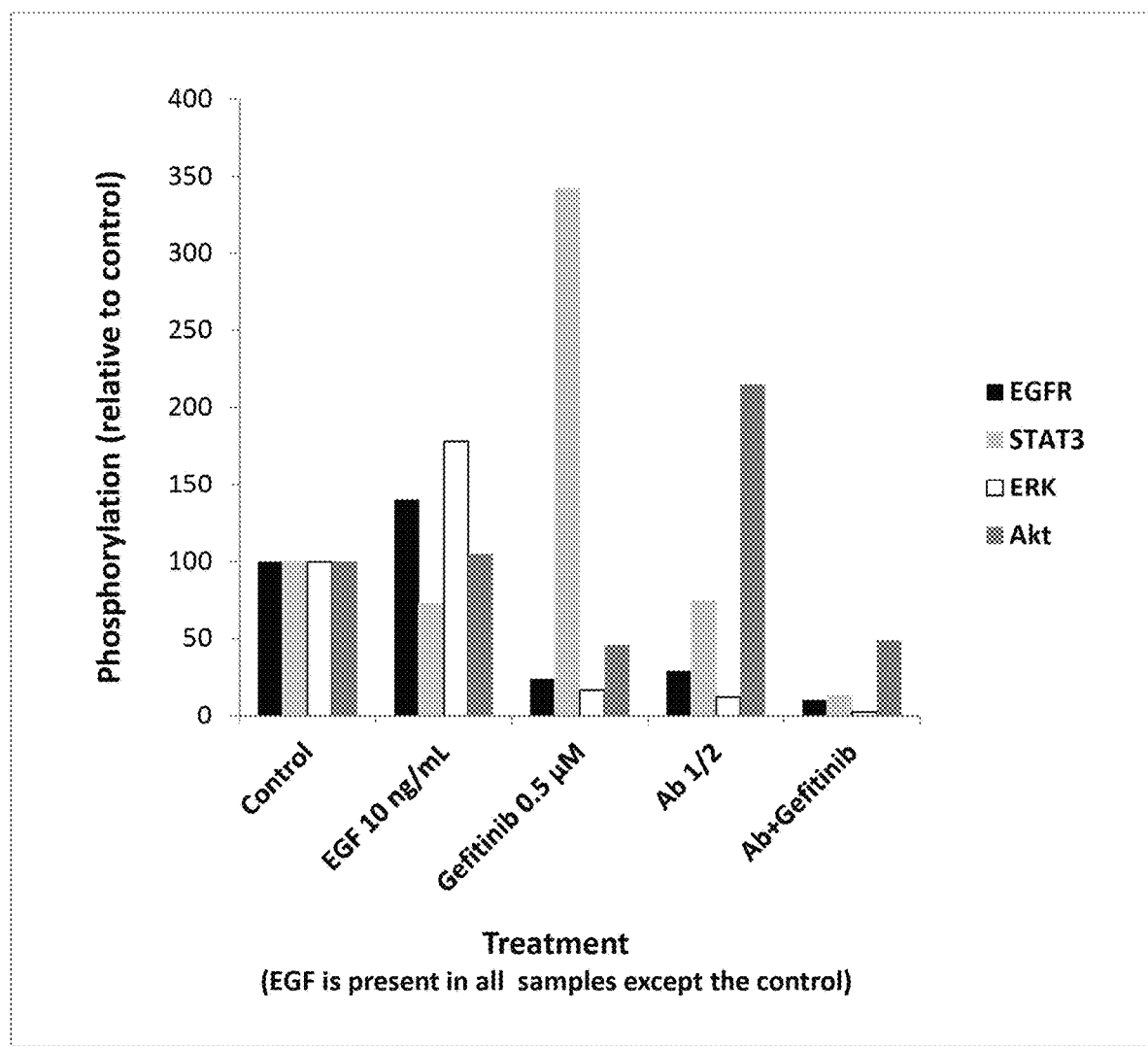
FIGS. 9A and 9B show the raw data for another experiment that was performed under "serum starvation conditions" and induction with EGFR. Incubation time was 2 h and the concentration of gefitinib was 0.5 μM.
Figure 9B:
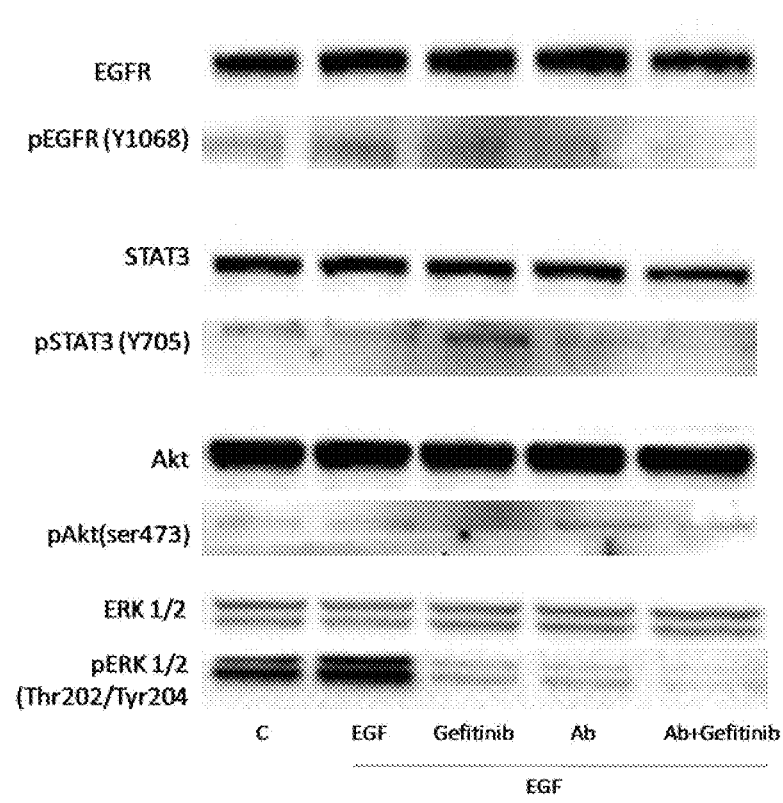
Figure 10A:
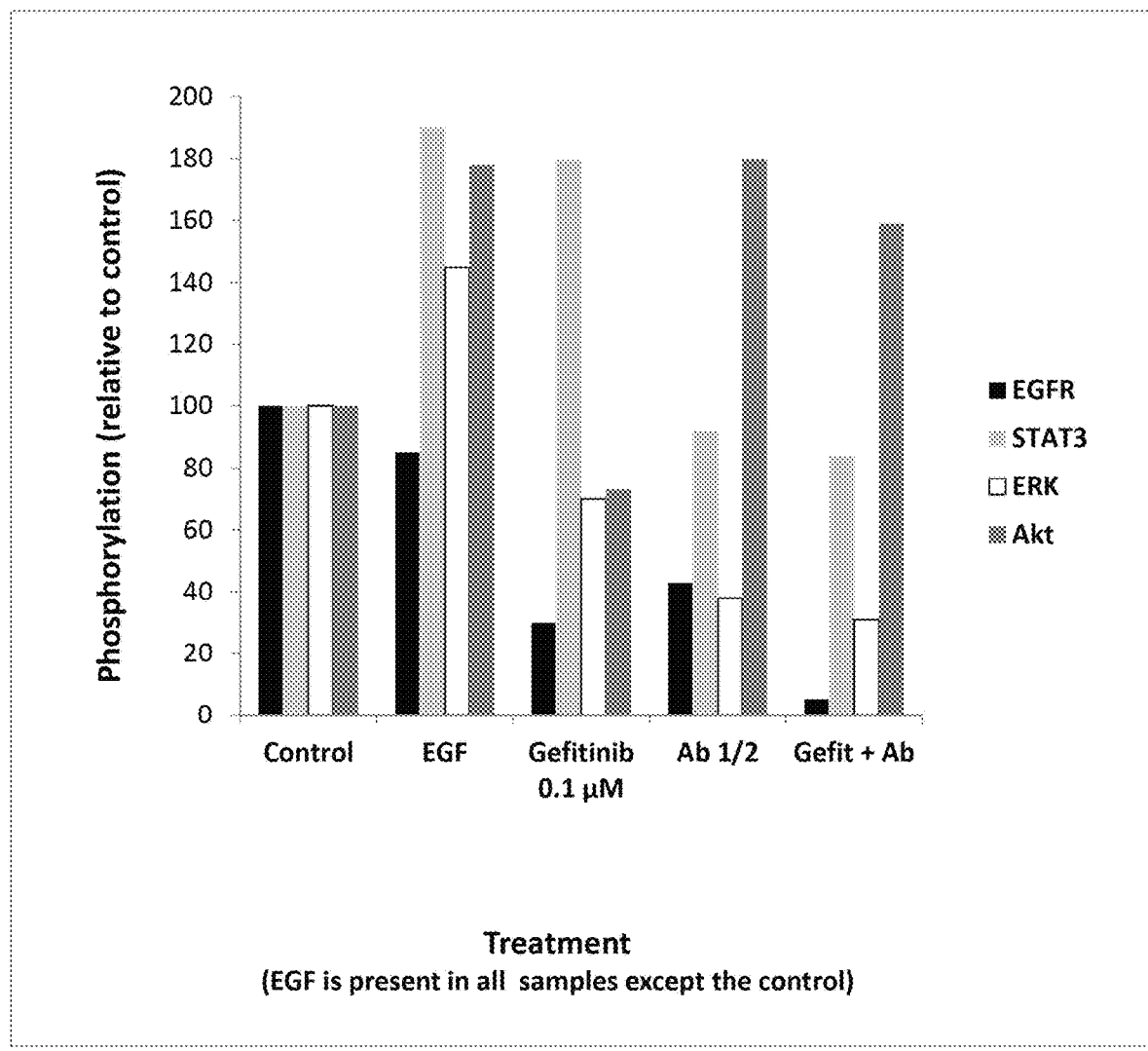
FIGS. 10A, 10B, 10C and 10D show the raw data for another set of additional experiments undertaken using concentrations of gefitinib corresponding better to physiological conditions observed in patents receiving this drug: 0.1 and 0.25 µM.
Figure 10B:
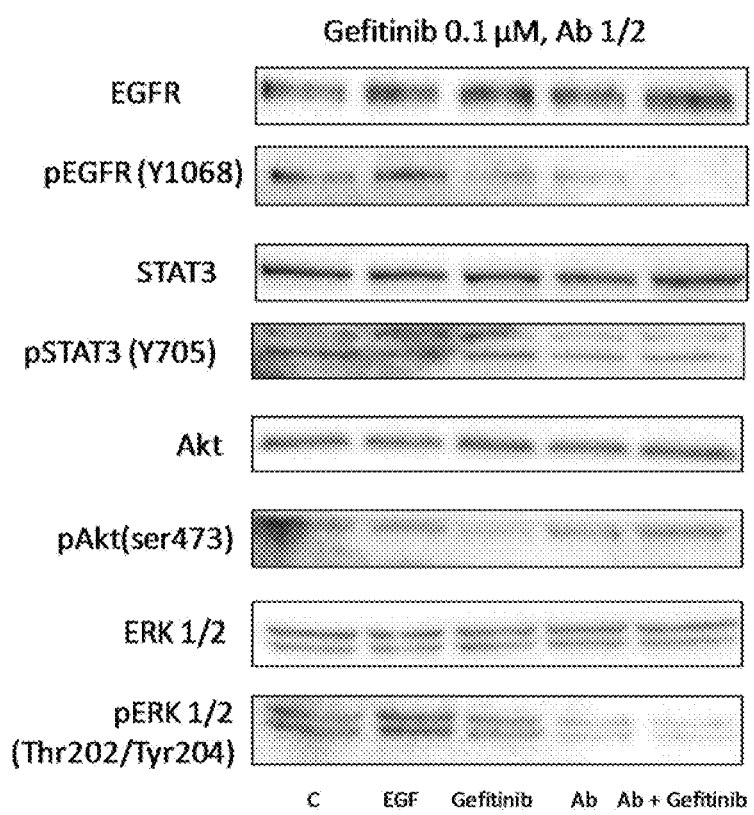
Figure 10C:
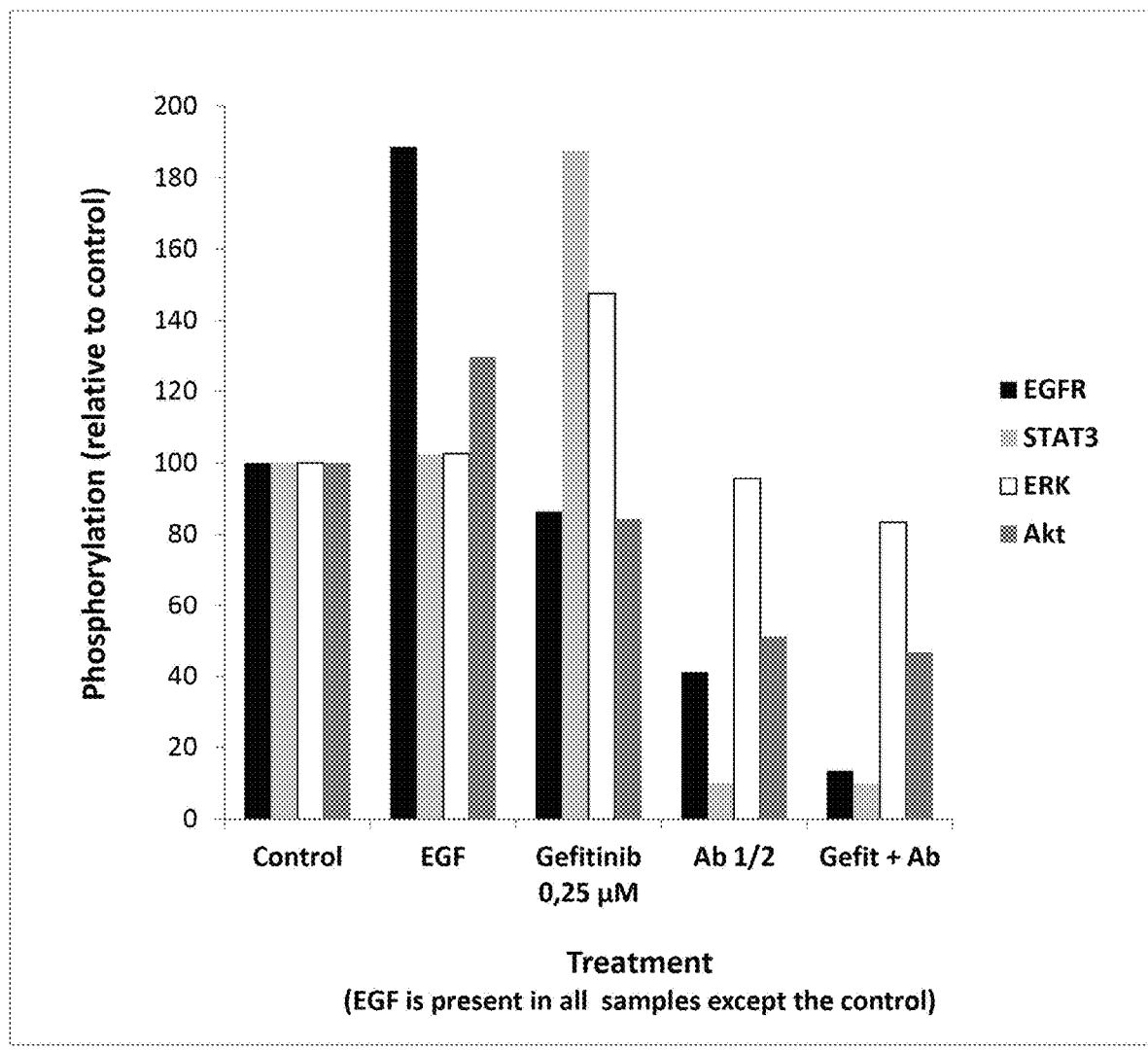
Figure 10D:
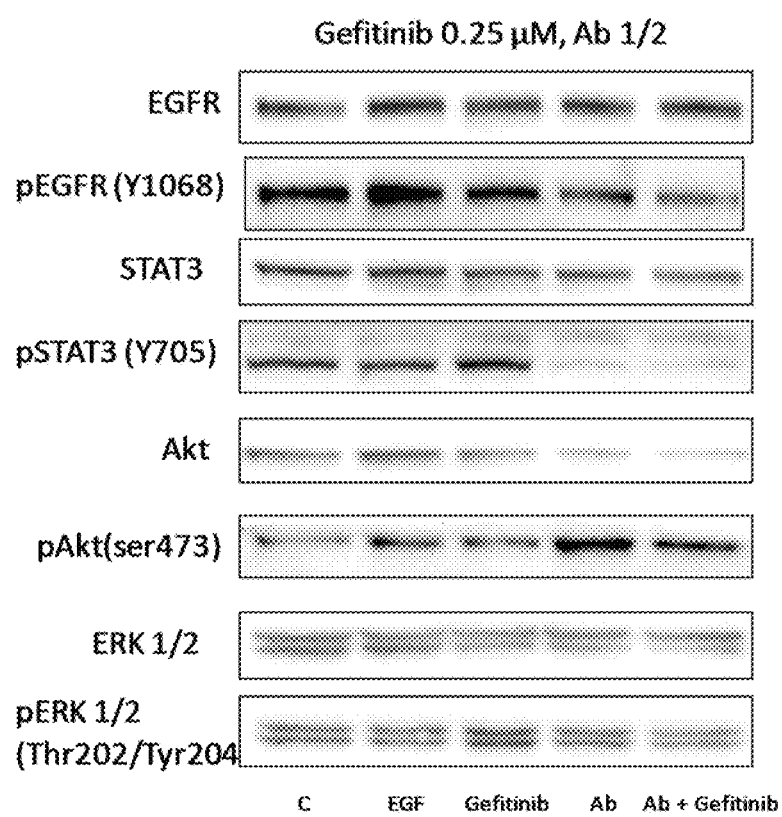

Another experiment was performed under "serum starvation conditions" and induction with EGFR. Incubation time was 2 h and the concentration of gefitinib was 0.5 µM (same as in third experiment). Again, it was apparent that gefitinib single-agent inactivated EGFR and Erk but activated STAT3, even more strongly that under "nonstandard" conditions. The anti-EGF single-agent significantly inactivated Erk, STAT3, and EGFR but activated Akt. When combining anti-EGF and gefitinib, Erk, STAT3, and EGFR were almost completely inactivated and Akt was also significantly inhibited, in light of the data shown depicted in FIGS. 9A and 9B.

Two additional experiments were undertaken using concentrations of gefitinib corresponding better to physiological conditions observed in patients receiving this drug: 0.1 and 0.25 µM. In experiments the anti-EGF prevented STAT3 activation by gefitinib, and a synergistic effect of the combination on pEGFR was observed. Results for Akt (but not for ERK) were consistent with our previous experience in the case of 0.25 and for 0.1 µM it was the reverse (consistency for ERK but not for Akt), as shown in FIGS. 10A, 10B 10C and 10D. These inconsistencies can probably be attributed to experimental errors.

Forth Set of Experiments (24 h)

Figure 11:
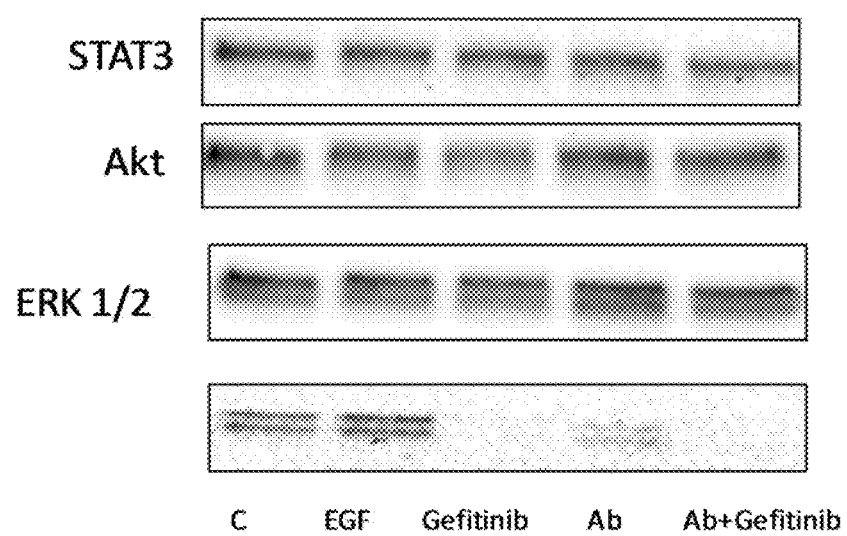
FIG. 11 shows the raw data of an experiment having a combination of gefitinib+anti-EGF with 24 h serum starvation and drug treatment.
Figure 12A:
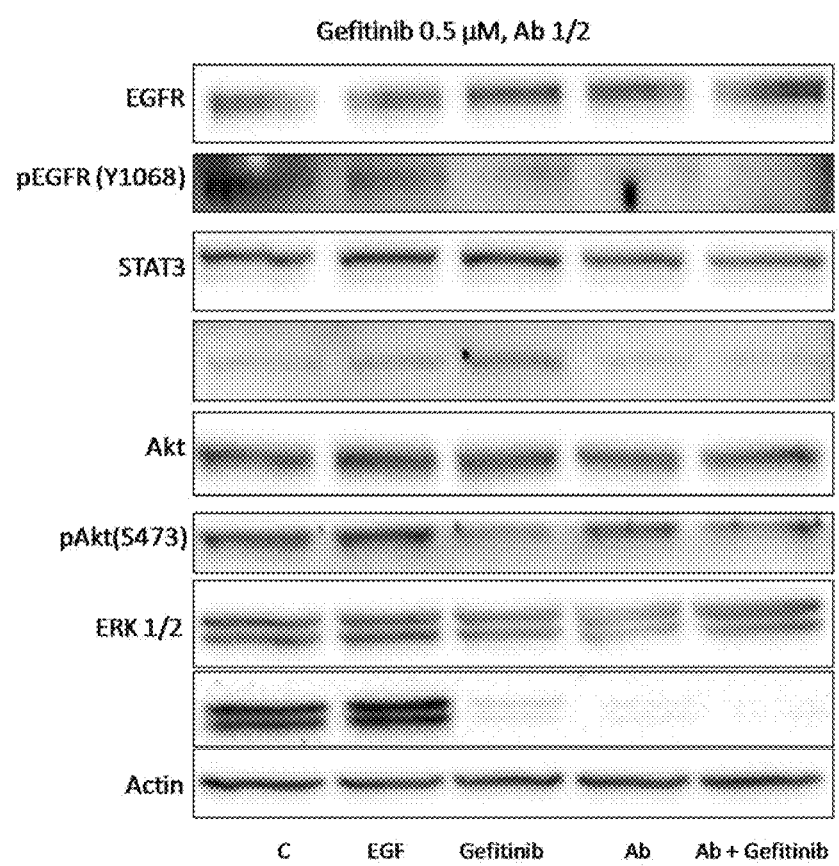
FIGS. 12A, 12B and 12C show the raw data for an additional experiment including a housekeeping protein (actin) to normalize total proteins, the experimental data show phosphorylation of ERK and EGFR was complete with the combination anti-EGF plus gefitinib.
Figure 12B:
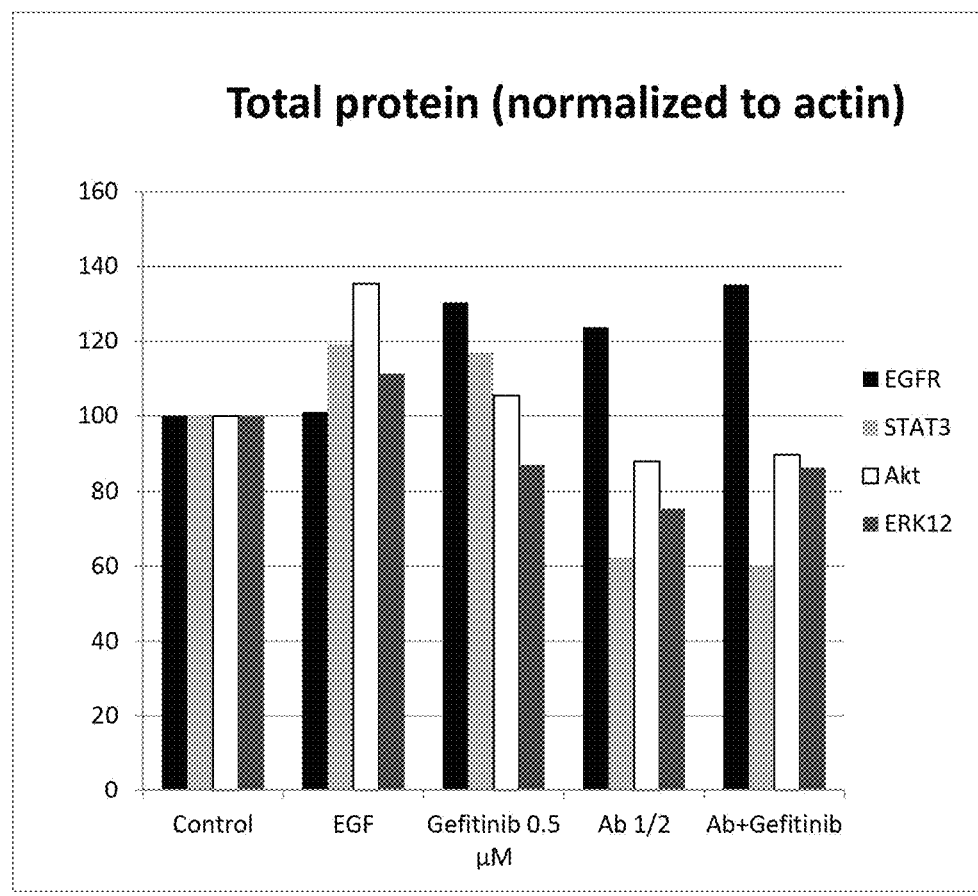
Figure 12C:
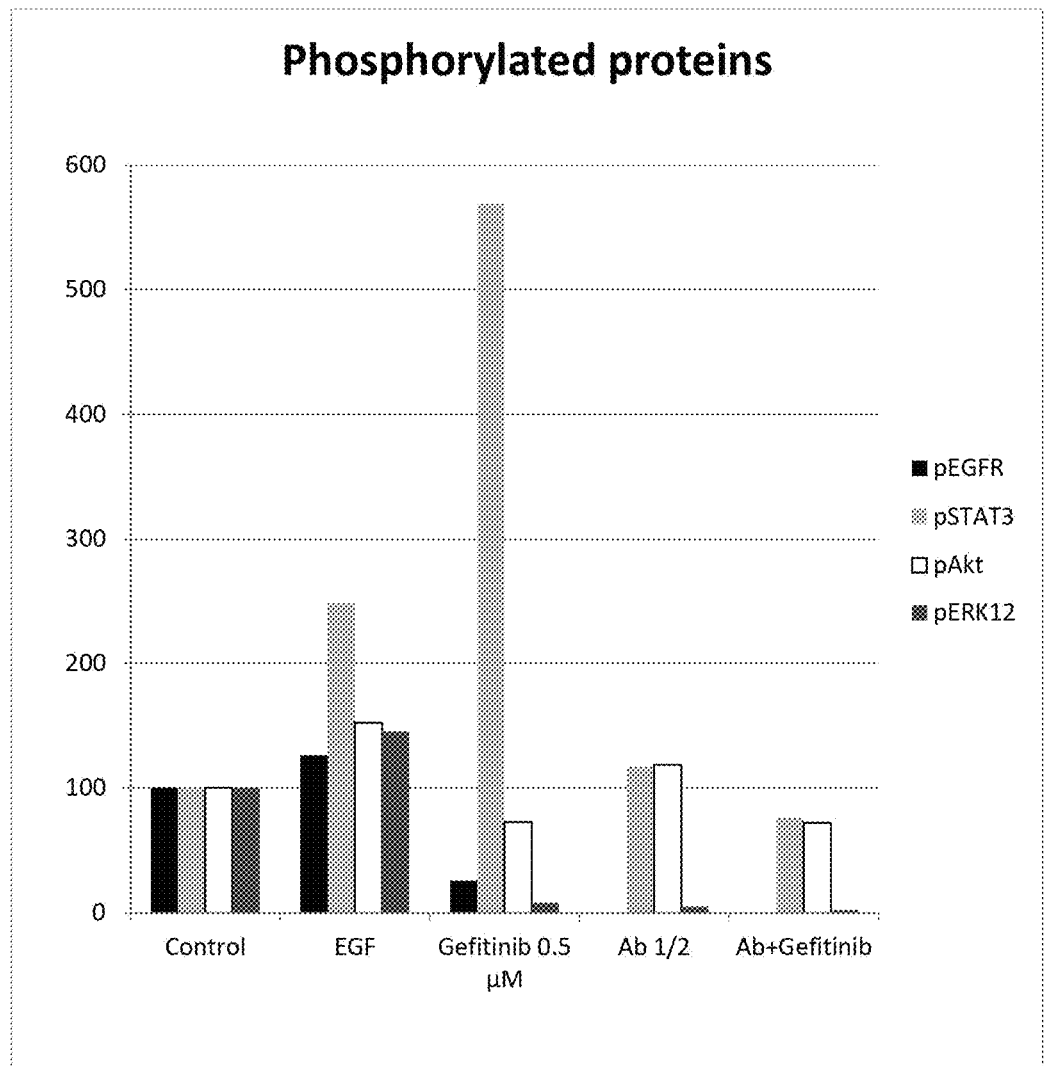

Two final combination experiments of gefitinib+anti-EGF were performed with 24 h serum starvation and drug treatment (see methods). A first experiment (see below) partly failed, and we were not able to determine several proteins. However, a complete (or almost complete) inhibition of ERK with gefitinib, anti-EGF and the combination was observed and a moderate downregulation of total STAT3 with anti-EGF seemed to be present as shown in FIG. 11. In order to confirm this result, a second experiment including a housekeeping protein (actin) to normalize total proteins was performed. In this experiment, phosphorylation of ERK and EGFR was complete with the combination anti-EGF plus gefitinib. Also, in the combination, anti-EGF completely reversed gefitinib-induced activation of STAT3 and gefitinib blocked the anti-EGF induced activation of Akt. Finally, a moderate downregulation in the levels of total STAT3 was observed in presence of the antibody or the combination as shown in FIGS. 12A, 12B and 12 C and summarized in Table 2 below.

TABLE 2

|  | pEGFR | pSTAT3 | pAkt | pERK |
| --- | --- | --- | --- | --- |
| Control | 100 | 100 | 100 | 100 |
| EGF | 125.7 | 248.4 | 151.9 | 144.8 |
| Gefitinib 0.5 µM | 25.5 | 569.2 | 72.6 | 8.1 |
| Ab ½ | 0 | 116.9 | 118.2 | 4.9 |
| Ab + Gefitinib | 0 | 75.8 | 71.9 | 2.3 |

Erlotinib and Anti-EGF in PC9 Cells

Figure 13A:
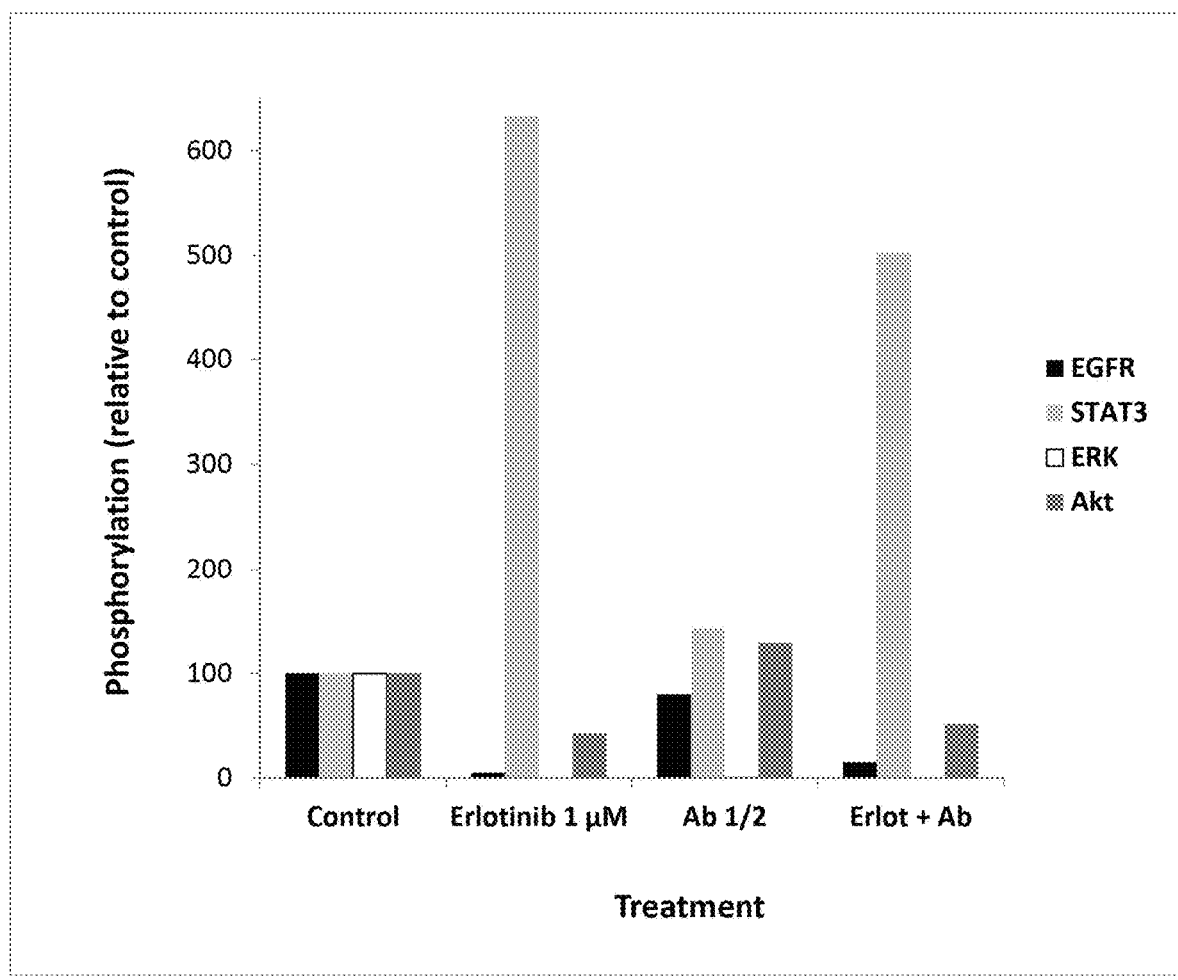
FIGS. 13A and 13B show the raw data for an additional experiment with erlotinib and anti-EGF under "nonstandard conditions" incubation time with the drugs was 2 hours and erlotinib concentration was 1 µM.
Figure 13B:
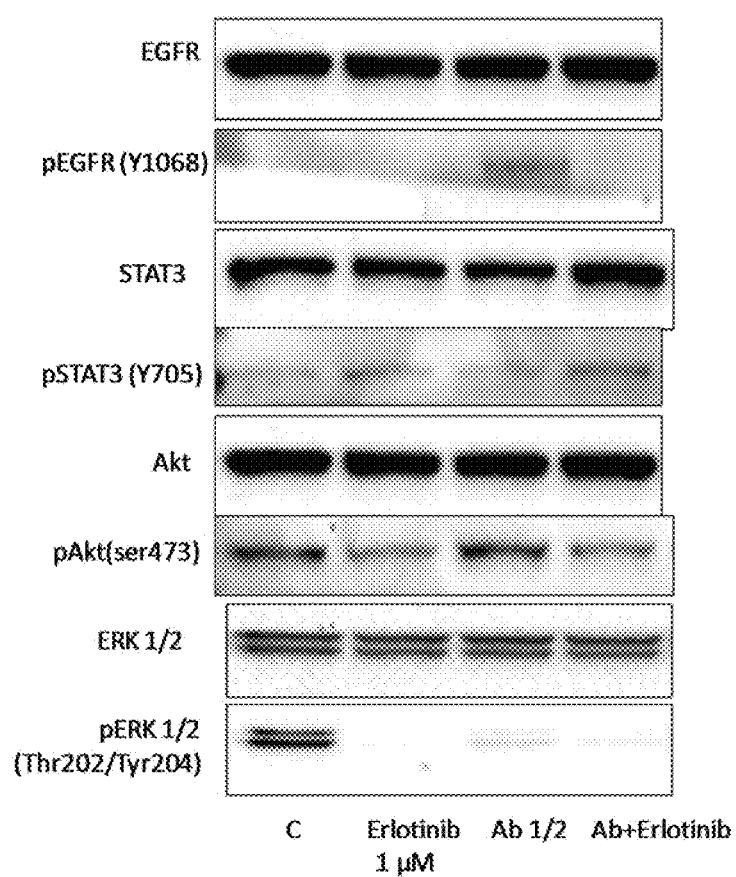

Based on the results obtained with gefitinib, we performed two additional experiments with erlotinib and anti-EGF under "nonstandard conditions" and "serum starvation." Incubation time with the drugs was 2 hours and erlotinib concentration was 1 µM. The results of the both experiments are shown for the nonstandard conditions in FIGS. 13A and 13B and for "serum starvation" in FIGS. 14A and 14B.

Figure 14A:
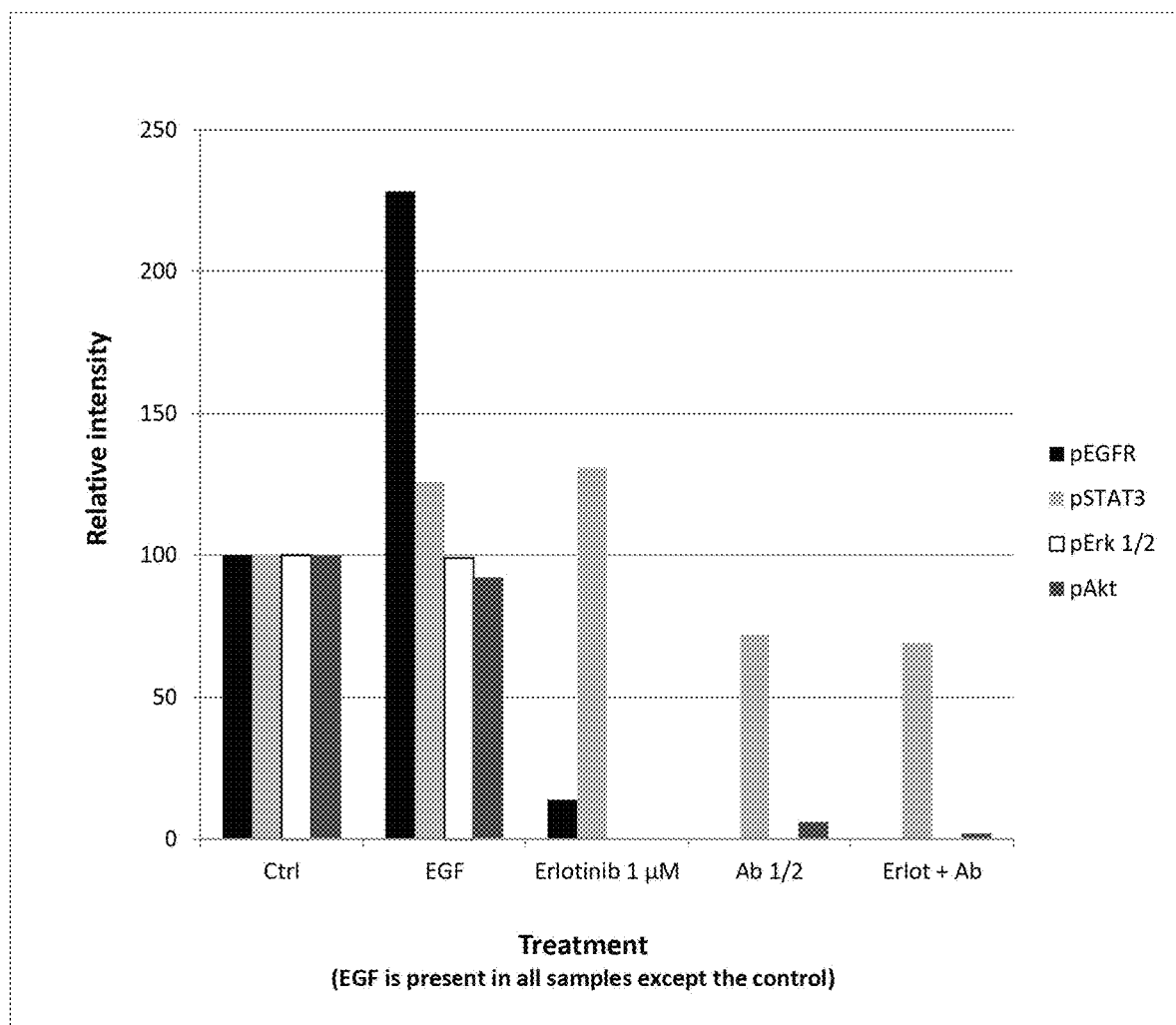
FIGS. 14A and 14B show the raw data for an additional experiment with erlotinib and anti-EGF under "serum starvation." incubation time with the drugs was 2 hours and erlotinib concentration was 1 µM.
Figure 14B:
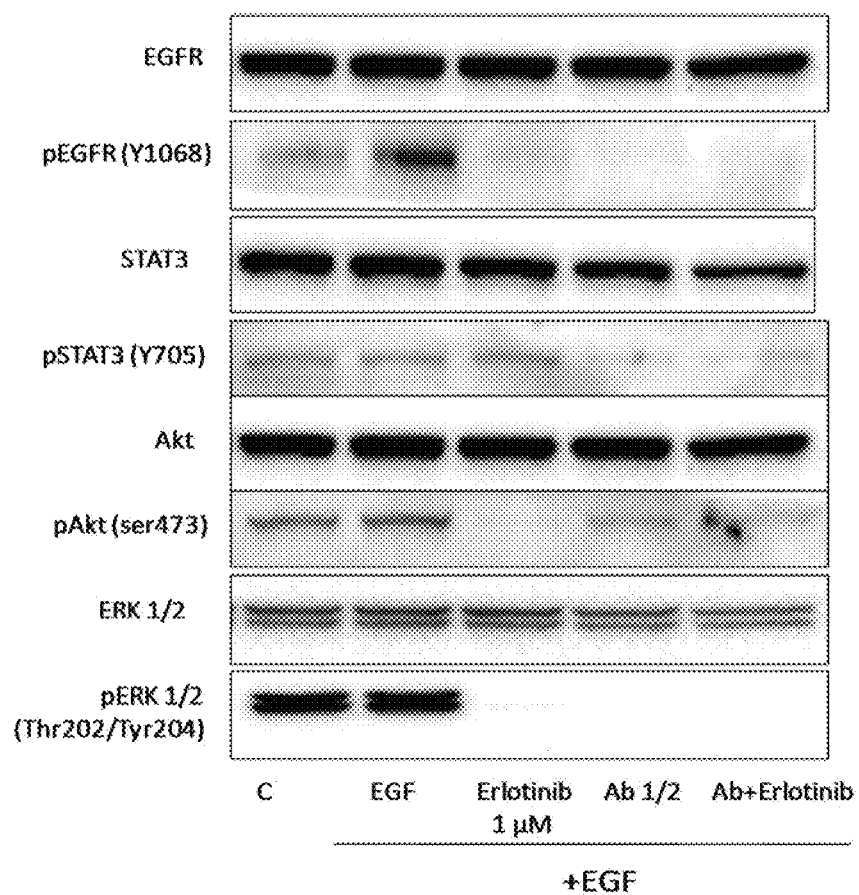

The results are in line with those obtained with gefitinib. Erlotinib single-agent inactivated EGFR and Erk but activated STAT3. The anti-EGF single-agent significantly inactivated Erk, EGFR and STAT3 (particularly under serum starvation as shown in FIGS. 14A and 14B) but activated Akt. When combining anti-EGF and erlotinib, Erk, Akt and EGFR were almost completely inactivated and STAT3 was also significantly inhibited compared with the cells treated with erlotinib. This synergistic effect of the combination erlotinib+antibody was observed both under serum starvation and standard conditions.

AZD9291 and Anti-EGF in PC9 Cells

Figure 15A:
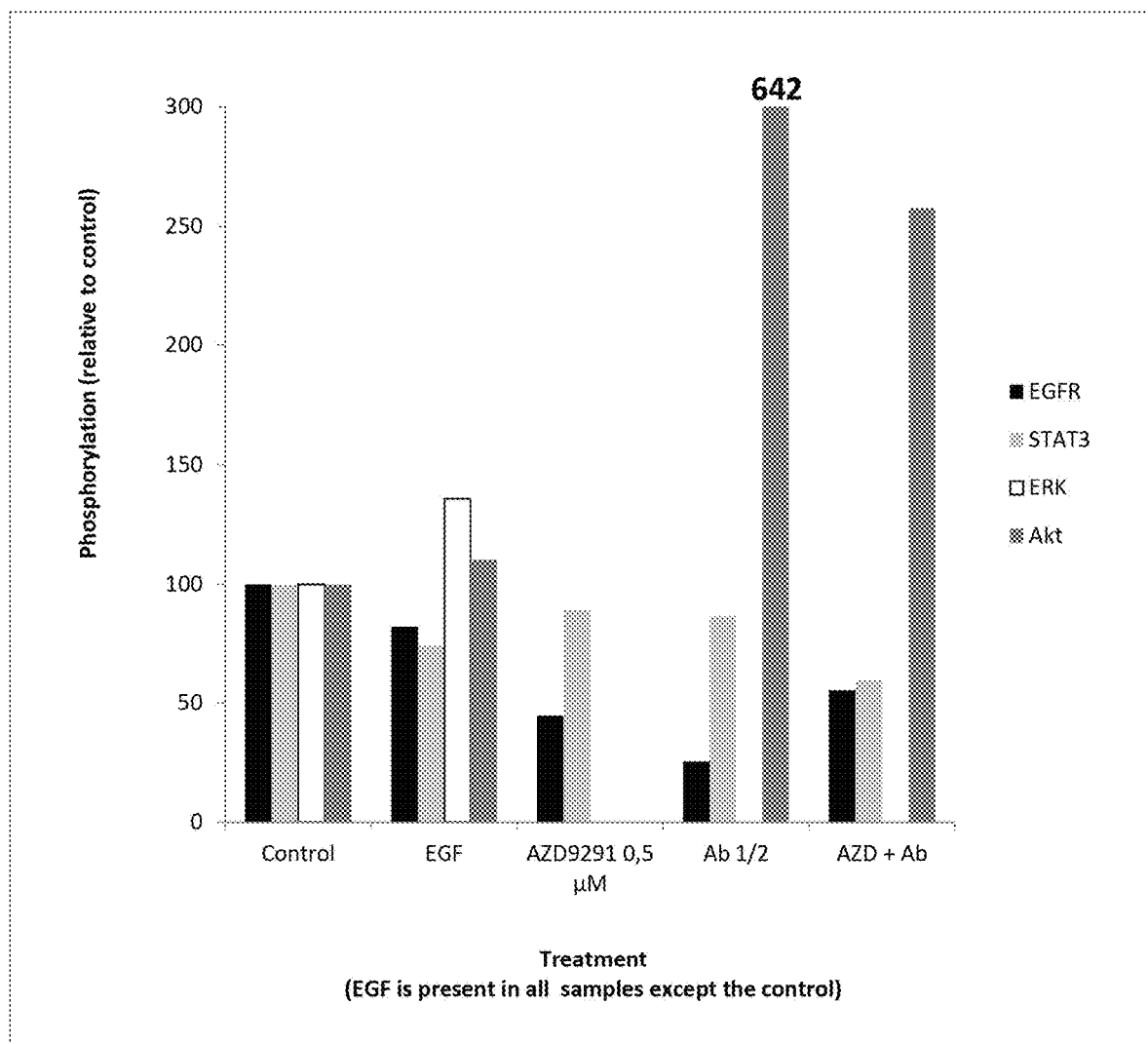
FIGS. 15A and 15B show the raw data for a further experiment using the TKI AZD9291 with the anti-EGF antibody tested under "serum-starvation" conditions.
Figure 15B:
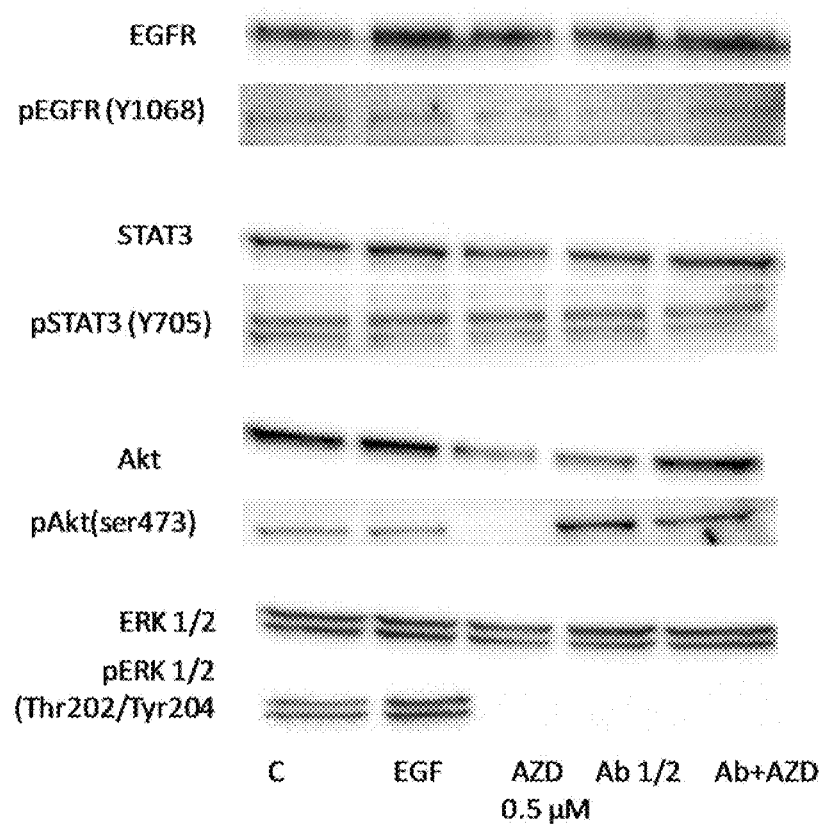

In a further experiment we used AZD9291, which is a new generation TKI able to bind to the EGFR protein with sensitizing and also resistant (T790M) mutations. It received Marketing approval in the US and EU and is commercialized with indication for NSCLC patients who have progressed to erlotinib/gefitinib. The interaction of AZD9291 with the anti-EGF antibody was tested under "serum-starvation" conditions and the results are shown in FIGS. 15A and 15B. The anti-EGF antibody completely blocked ERK and also inhibited EGFR phosphorylation, the effect was as potent as that of the second generation TKIs AZD9291. Again, the anti-EGF antibody induced Akt.

Findings

Administration of gefitinib or erlotinib to the EGFR-mutated, TKI sensitive PC9 cells leads to activation of STAT3, considered as first step in acquisition of resistance to therapy. Incubation periods of 2 and 24-hour incubation dramatically increased this effect under serum starvation.

Exposure of PC9 cells to anti-EGF does not activate STAT3. On the contrary, it has some inhibitory effect that is reproducible and more significant with 2 and 24 hour incubation.

The anti-EGF single agent activates Akt but this effect is reversed when gefitinib or erlotinib is also present. Under the conditions of the "serum starved" experiments, the effect of the anti-EGF on EGFR and ERK1/2 phosphorylation is at least as significant as the effect of gefitinib or erlotinib on these signaling molecules. Combination treatment with gefitinib and anti-EGF shows additional (apparently synergistic) effect for pEGFR and pERK1/2 inhibition and blocks the activation of the four proteins under study: EGFR, ERK, Akt, and STAT3.

Un-expectedly, the combination treatment reproducibly reverses the activation of STAT-3 by gefitinib or erlotinib in both "serum-starved" and "non-standard" conditions. The reversion is complete in the case of Gefitinib when incubation periods are extended to 2 or 24 hour, with the phosphorylation of STAT3 dropping to the levels of non-induced, serum-starved cells. In the case of 24 hour incubation a moderate down-regulation of total STAT3 protein by anti-EGF was also observed.

All these above findings suggest that first-line combination treatment could be beneficial in EGFR mutated NSCLC patients since it has the potential to delay the appearance of resistance to TKIs. The anti-EGF antibody substantially blocks Erk and partially inhibits EGFR phosphorylation in the PC9-derived, T790M cell line resistant to TKI. The anti-EGF antibody is as effective as the second generation drug AZD9291 as a mono-therapy.

Example 3: Assessment of Anti EGF (Single-Agent and Combined with TKIs) on Inhibition of EGF/EGFR Pathways with WB as Endpoint In a further experiment in was conducted to compare in the PC9 NSCLC cell line, the effects of anti-EGF antibodies with AZD9291 (third generation TKI) on the inhibition of the pathways activated by EGF-EGFR binding. The Experiment was designed to assess whether, in the same cell line, the combination of anti EGF and TKI is superior to single-agent treatment. It was also designed to compare, in a PC9 cell line resistant to Gefitinib carrying the T790M mutation (PC9-GR4), the effects of anti-EGF antibodies and AZD9291 on the inhibition of the pathways activated by EGF-EGFR binding and to assess whether, in the same cell line, the combination of anti EGF and AZD9291 is superior to single-agent treatments. Finally, the experiment was an attempt to determine, in the PC9 NSCLC cell line, the effects of the anti-EGF on the molecular mechanisms implicated in resistance to TKIs Materials and Methods for Testing Activation by Western Blotting (WB) Methodology Cell Lines As described above, the PC9 cell line carries a 15 bp deletion in exon 19 of EGFR, making this cell line sensitive to TKI's. It represents a model for the EGFR Mutated segment of the NSCLC patient population receiving TKI treatment. As a part of this effort, PC9-derived cell lines resistant to TKIs were developed. The parental PC9 are NSCLC-derived cells that harbor a 15 bp deletion and are extremely sensitive to first, second and third generation TKIs, such as gefitinib and AZD9291 (IC50 in the nM range). PC9 cells were treated with increasing concentrations of erlotinib and gefitinib over a period of 2 months and obtained 6 different lines (PC9-ER and GR1 to GR5) that were resistant to both gefitinib and erlotinib (IC50 around 5-10 Similarly to patients, none of the 6 lines lost the sensitizing mutation (15 bp deletion) but the resistant mutation T790M is present in two of them. These two cell lines (PC9-GR1 and GR4) are sensitive to the new generation EGFR TKI developed by Astra Zeneca (AZD9291) that can also bind to the T790M EGFR mutated protein.

Materials

All tissue culture materials were obtained from Biological Industries (Kibbutz Beit Haemek, Israel) or Invitrogen (Paisley, Scotland, UK). The PC9 cell line was kindly provided by F. Hoffman-La Roche Ltd (Basel, Switzerland), under the authorization of Dr. Mayumi Ono, the investigator who established the cell line. Cells were cultured in RPMI medium supplemented with 10% fetal bovine serum (FBS), 50 µg/mL penicillin-streptomycin and 2 mM L-Glutamine and maintained in a humidified atmosphere with 5% $CO_2$ at 37° C. Bioven provided the anti-EGF antibodies.

Two kinds of antibodies were used in this study:
- Ab1: Anti-EGF antibodies derived from an immunization study in monkeys that received 4 immunizations of the rEGF-rP64k CIMAVax-EGF conjugate formulated with Montanide adjuvant, as described above. These are the so-called "Ab1" or "Bioven anti-EGF antibodies". Serum was treated on Mellon gel to remove contaminants such as complement. This purification step was conducted at Scotia, Aberdeen, UK. The pre-treatment Elisa titer was: 1/60000. Gefitinib was purchased from Selleck Chemicals (Houston, TX). EGF and antibodies for Western blotting were purchased from Santa Cruz Biotechnologies (Palo Alto, CA).
- Ab2: Anti-EGF antibodies derived from immunization of rabbits with a recombinant fusion molecule containing modified CTB and EGF sequences. These are the so-called "Ab2" or "Bioven anti-EGF2 antibodies" The immunogenic recombinant fusion molecule containing modified CTB and EGF sequences is shown in Sequence 1 and further described FIG. 20A (and as further described in WO2013/076580 incorporated by reference in its entirety) having a sequence as follows:

```
Sequence 1:
MNSYPGCPSSYDGYCLNGGVCMHIESLDSYTCNCVIGYSGDRCQTRDLR

WWELRGSSGNSDSECPLSHDGYCLHDGVCMYIEALDKYACNCVVGYIGE

RCQYRDLKWWELRGGSGGTSGGGGGSGTPQNITDLCAEYHNTQITITLN

DKIFSYTESLAGKREMAIITFKNGATFQVEVPGSQHIDSQKKAIERMKD

TLRIAYLTEAKVEKLCVWNNKTPHAIAAISMANHHHHHH
```

Although not used in this experiment an additional Anti-EGF antibodies can be derived from immunization of rabbits with a recombinant fusion molecule containing modified CTB and EGF sequences as shown in Sequence 2 and further described FIG. 20B (as described in WO2013/076580 incorporated by reference in its entirety) having a sequence as follows:

```
Sequence 2:
NSDSECPLSEIDGYCLEIDGVCMYIEALDKYACNCVVGYIGERCQYRDL

KWWELRGSSGNSDSECPLSEIDGYCLHDGVCMYIEALDKYACNCVVGYI

GERCQYRDLKWWELRGGSGGTSGGGGGSGTPQNITDLCAEYHNTQITIT

LNDKIFSYTESLADKREMAIITFKNGATFQVEVPGSQHDSQKKAIERMK

DTLRIAYLTEAKVEKLCVWNNKTPPAIAAISMAN
```

The following hybridomas have been deposited with the European Collection of Cell Cultures, Culture Collections, Public Health England, Porton Down, Salisbury, Wiltshire SP4 0JG (ECACC):

| Cell Lines | ECACC Accession No. | Deposit Date |
|---|---|---|
| Sequence 2 | | Mar. 15, 2016 |
| Sequence 1 | | Mar. 17, 2016 |

These deposits were made under the provisions of the Budapest Treaty on the International Recognition of the Deposit of Microorganisms for the Purpose of Patent Procedure and the Regulations thereunder (Budapest Treaty). This assures maintenance of a viable deposit for 30 years from the date of deposit. These cell lines will be made available by ATCC under the terms of the Budapest Treaty, and subject to an agreement between Bioven and ATCC, which assures permanent and unrestricted availability of the cell lines to the public upon issuance of the pertinent U.S. patent or upon laying open to the public of any U.S. or foreign patent application, whichever comes first, and assures availability of the cell lines to one determined by the U.S. Commissioner of Patents and Trademarks to be entitled thereto according to 35 USC § 122 and the Commissioner's rules pursuant thereto (including 37 CFR § 1.14 with particular reference to 886 OG 638).

Blood was collected pre-immunization and after several immunizations. Serum was purified on Mellon gel to remove non-immunoglobulin including complement. This purification step was conducted at Scotia, Aberdeen, UK.

Treatments

In a standard experiment, T-25 flasks of the PC9 or PC9-GR4 cell line were submitted to serum deprivation (o/n), washed (×2) and treated with the anti-EGF (single agent and combined with gefitinib or AZD9291) pre-incubated at 37° C. for 10 min with serum-free medium containing 10 ng EGF/mL. The incubation time of the cells with the drugs was 2 or 24 h. Concentrations of gefitinib or AZD9291 were tested at concentrations dependent of the cell lines. In 5-day experiments, PC9 cells were not submitted to serum starvation but cultured with human serum. They were washed with PBS (×2), drugs (anti-EGF, gefitinib or the combination) were added in medium containing 10% human serum and incubated for 5 days.

Western Blotting

After treatment, the cultures were washed with PBS and lysed in protease and phosphatase inhibitors-containing lysis buffer. Equal amounts of protein were loaded onto an SDS-PAGE gel, transferred to a membrane and blotted with antibodies against EGFR, p-EGFR, ERK1/2, p-ERK1/2, Akt, p-Akt, STAT-3, pSTAT-3, Bmi1, HES1, PARP, PARP cleaved, Notch3, Notch3 truncated, AXL, pYAP and tubulin. The intensity of the bands was determined using the ImageJ program and then submitted to two-step normalization. First, the intensity of the phosphorylated band was divided by the intensity of the band corresponding to the total protein in the same sample. This value was then divided by the value obtained in the EGF-treated cells for the same protein.

Results AZD9291 and Anti-EGF (Ab1) in PC9 Cells First Experiment (2 h, 0.2 μM Gefitinib)

Figure 16A:
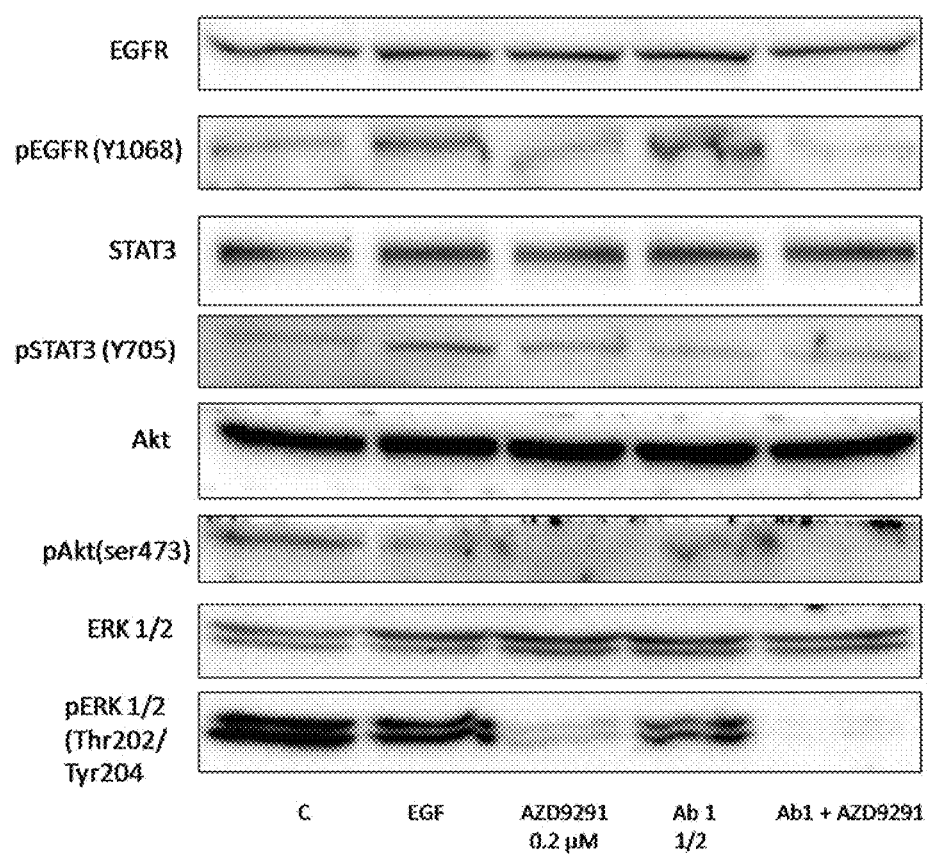
FIGS. 16A and 16B show the raw data for another experiment using AZD9291 and anti-EGF (Ab1) in PC9 cells.
Figure 16B:
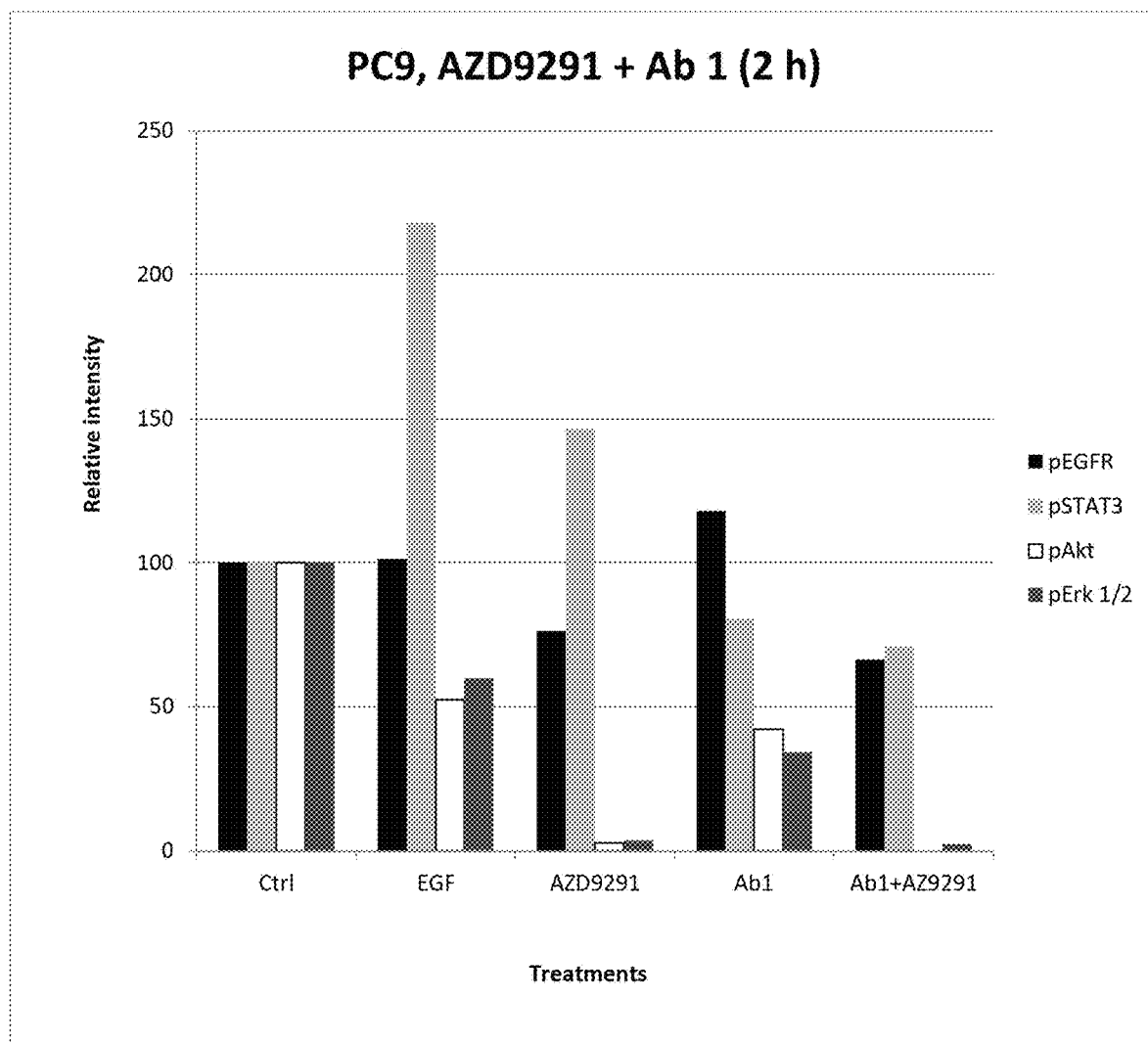

The results of the first experiment (Western blotting and quantification of the phosphorylated proteins) are depicted in FIGS. 16A and 16B. As shown in the figures there was inhibition of the phosphorylation of EGFR, STAT3, Akt and Erk by AZD9291 at 0.2 μM. As usual, the antibody single agent inhibited pSTAT3 and pErk but activated Akt. The combination was clearly superior to the two drugs alone in the case of pEGFR and pErk. Also, pAkt was completely inhibited and pSTAT3 goes below the basal level, as summarized in table 3 below.

TABLE 3

|  | pEGFR | pSTAT3 | pAkt | pErk ½ |
|---|---|---|---|---|
| Ctrl | 100 | 100 | 100 | 100 |
| EGF | 101.5 | 218.1 | 52.4 | 60 |
| AZD9291 | 76.3 | 146.6 | 2.9 | 3.7 |
| Ab1 | 118 | 80.4 | 42.2 | 34.1 |
| Ab1 + AZ9291 | 66.4 | 70.9 | 0 | 2.4 |

Second Experiment (24 h, 0.1 μM AZD9291)

Figure 17:
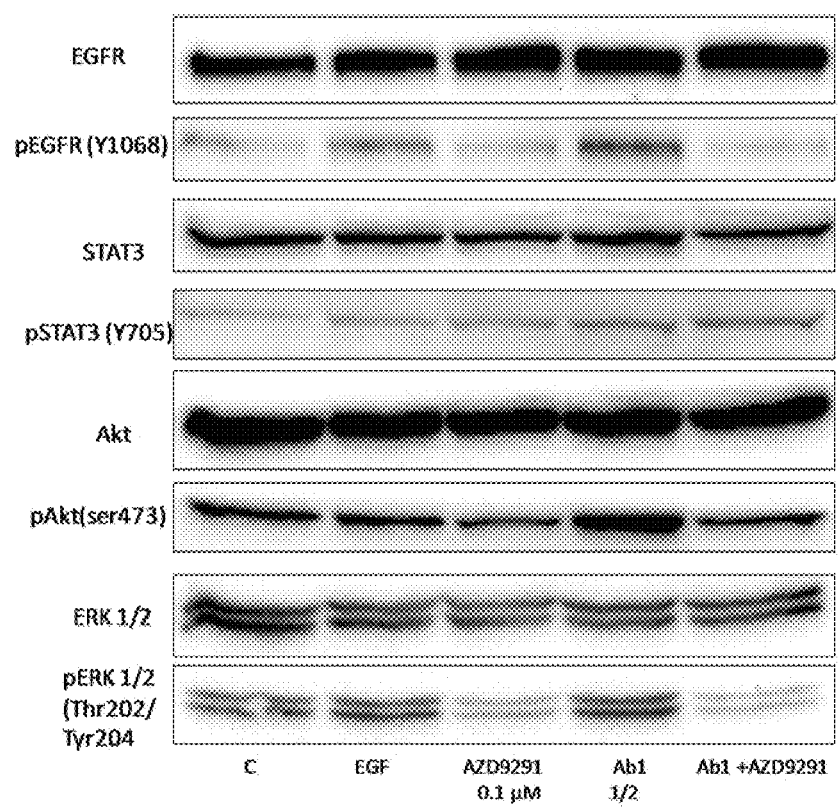
FIG. 17 shows the raw data in a further experiment where PC9 cells were incubated with 24 h with the drug AZD9291, who's concentration was reduced to 0.1 µM to prevent complete inactivation of EGFR and Erk by the drug.

In a further experiment, PC9 cells were incubated with 24 h with the drugs. Due to this longer incubation time, concentration of AZD9291 was reduced to 0.1 μM to prevent complete inactivation of EGFR and Erk by the drug. Results are shown in FIG. 17. The only effect of the anti-EGF antibody single-agent was Akt activation, raising concerns about the possible inactivation of the aliquot of antibody used. (Note: This Western blot was not quantified due to those doubts)

AZD9291 and Anti-EGF (Ab1) in PC9-GR4 (T790M Positive) First Experiment (2 h, 0.2 μM AZD9291)

Figure 18A:
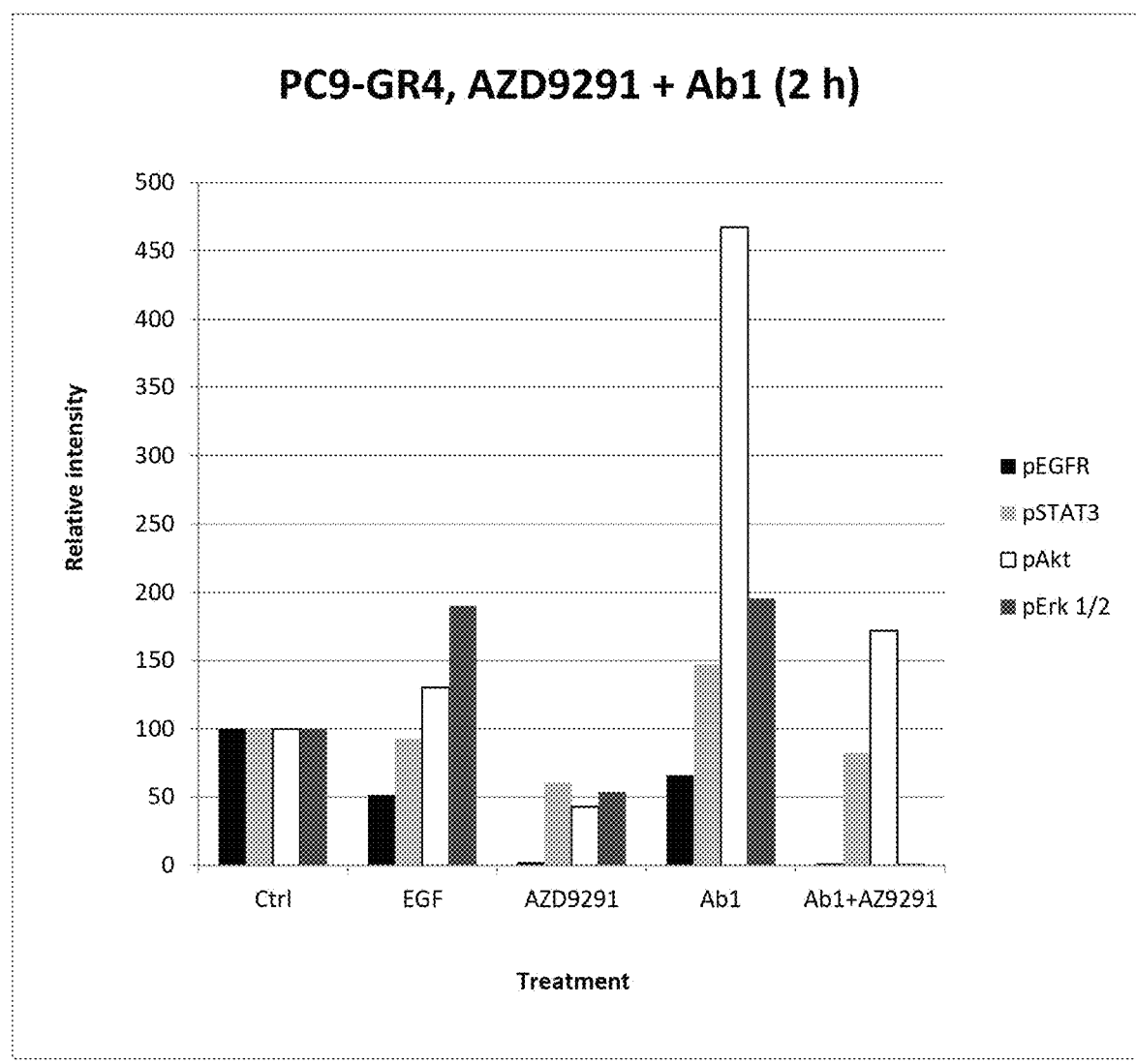
FIGS. 18A and 18B depict the raw data in another experiment with AZD9291 (0.2 AZD9291) and anti-EGF (Ab1) in PC9-GR4 (T790M positive) with a 2 hour incubation period.
Figure 18B:
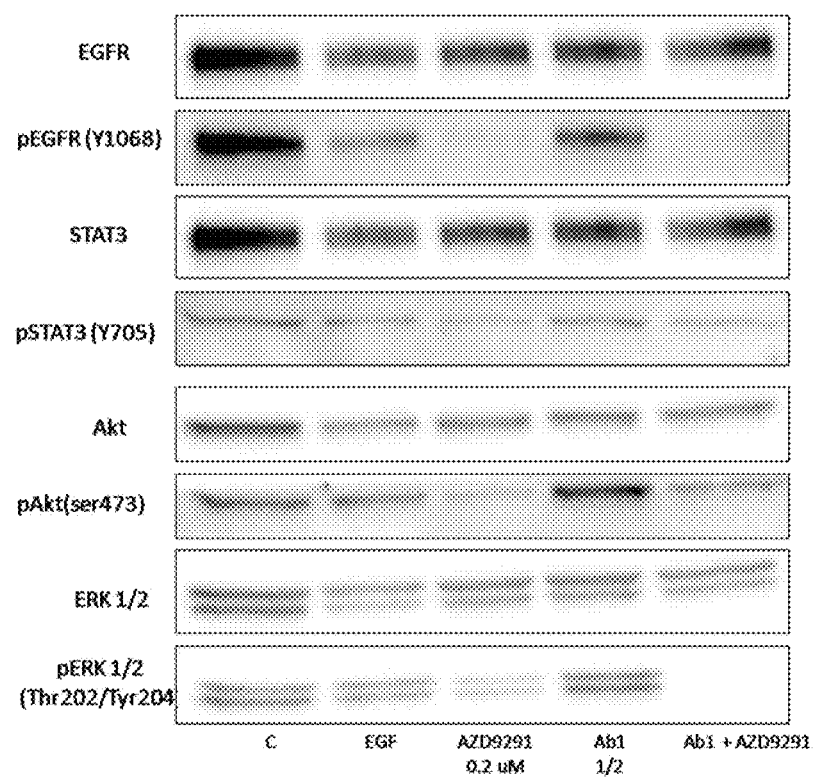

In this cell line, EGF did not have much effect on phosphorylation of Erk, STAT-3 or Akt and seemed even to have an inhibitory effect on pEGFR. At 2 h, AZD9291 (at 0.2 μM) completely blocked pEGFR and partly pAkt and pErk. There was no clear stimulatory effect on pSTAT3. The anti-EGF antibody stimulated Akt phosphorylation (same as in parental PC9). The combination of both agents was in the range of AZD9291 single agent in the case of pSTAT-3 and pAkt, and was superior in the case of pEGFR and particularly pErk. As shown in FIGS. 18A and 18B and summarized in table 4.

TABLE 4

|  | pEGFR | pSTAT3 | pAkt | pErk ½ |
|---|---|---|---|---|
| Ctrl | 100 | 100 | 100 | 100 |
| EGF | 51.3 | 92.7 | 130.3 | 190.5 |
| AZD9291 | 2.5 | 60 | 42.7 | 53.6 |
| Ab1 | 65.7 | 147.2 | 467 | 195.8 |
| Ab1 + AZ9291 | 1.6 | 82.2 | 172.2 | 1.5 |

Second Experiment (24 h, 0.2 μM AZD9291)

Figure 19A:
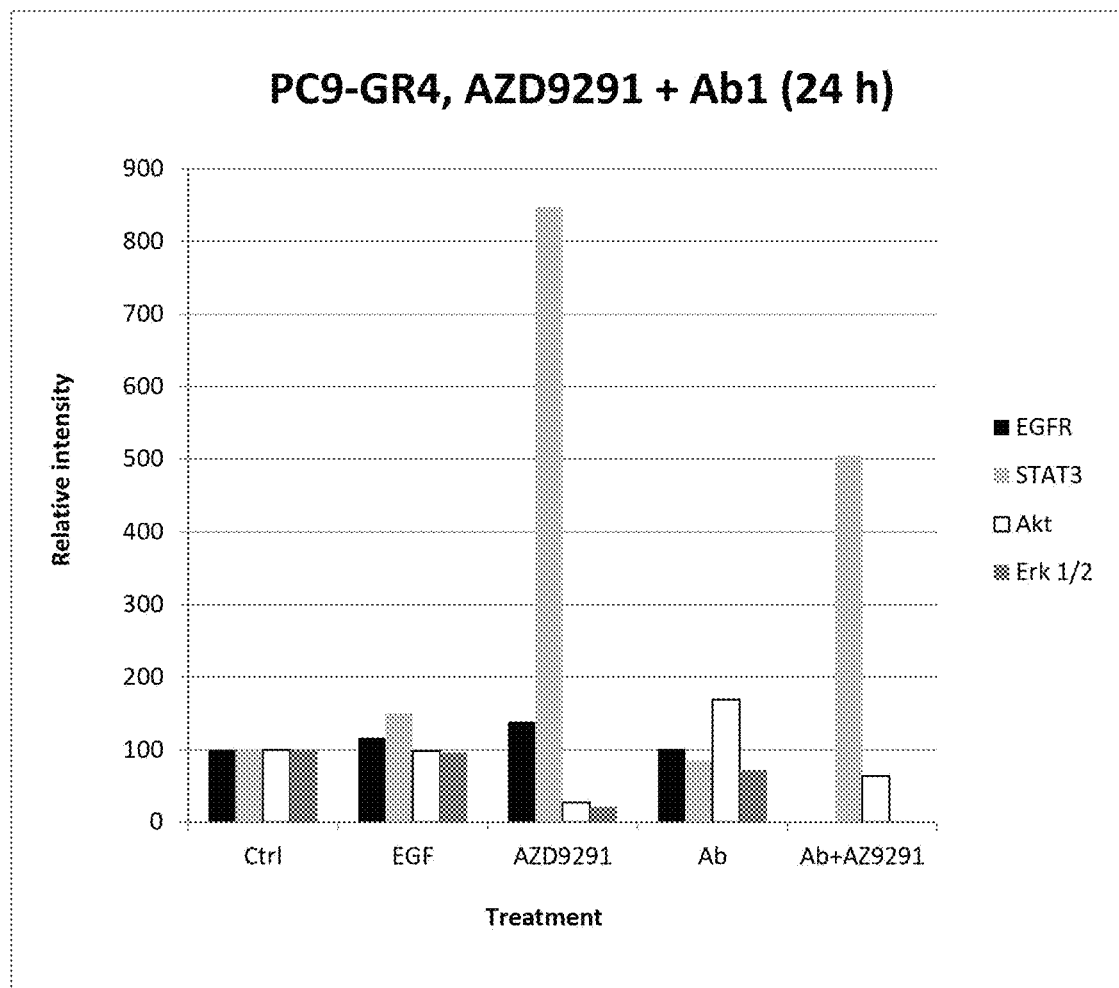
FIGS. 19A and 19B depict the raw data in another experiment with AZD9291 (0.2 µM AZD9291) and anti-EGF (Ab1) in PC9-GR4 (T790M positive) with a 24 hour incubation period.
Figure 19B:
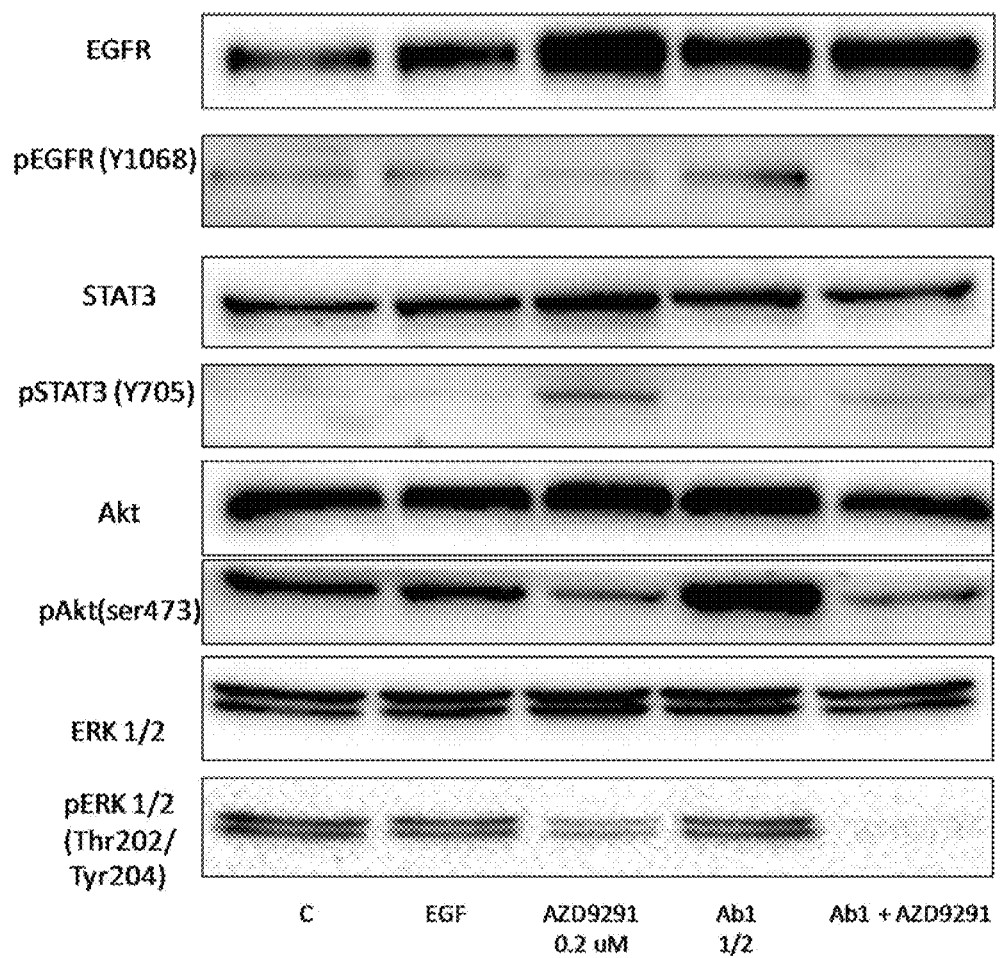
Figure 21A:
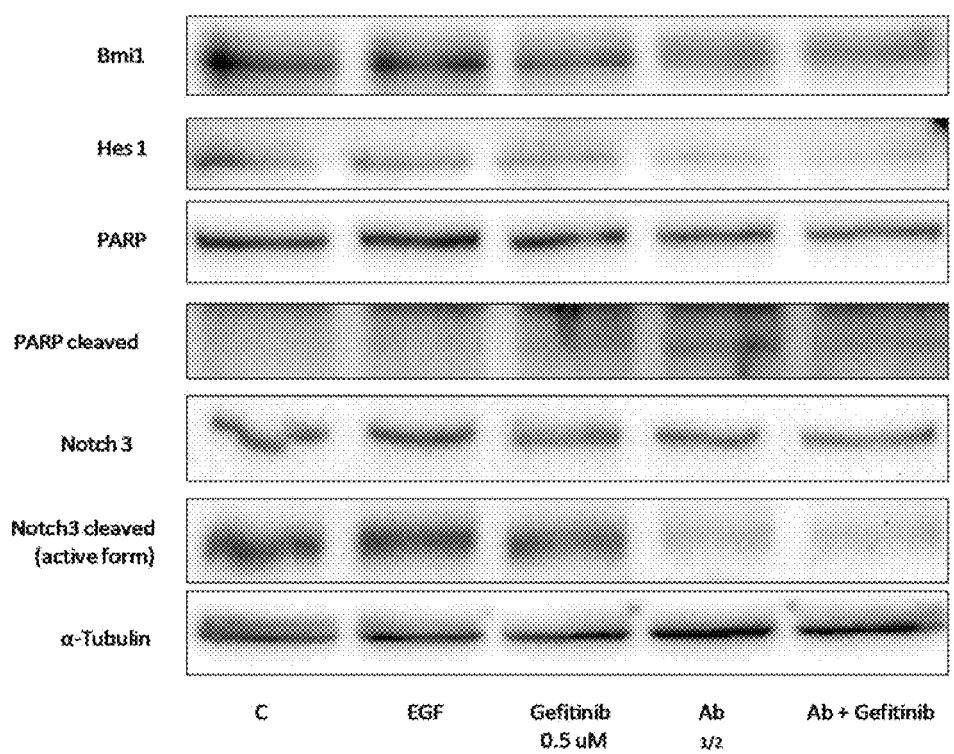
FIGS. 21A, 21B, 21C and 21D show the raw data in further experiment with gefitinib and anti-EGF (Ab1) in PC9 cells and the effect on additional makers.
Figure 21B:
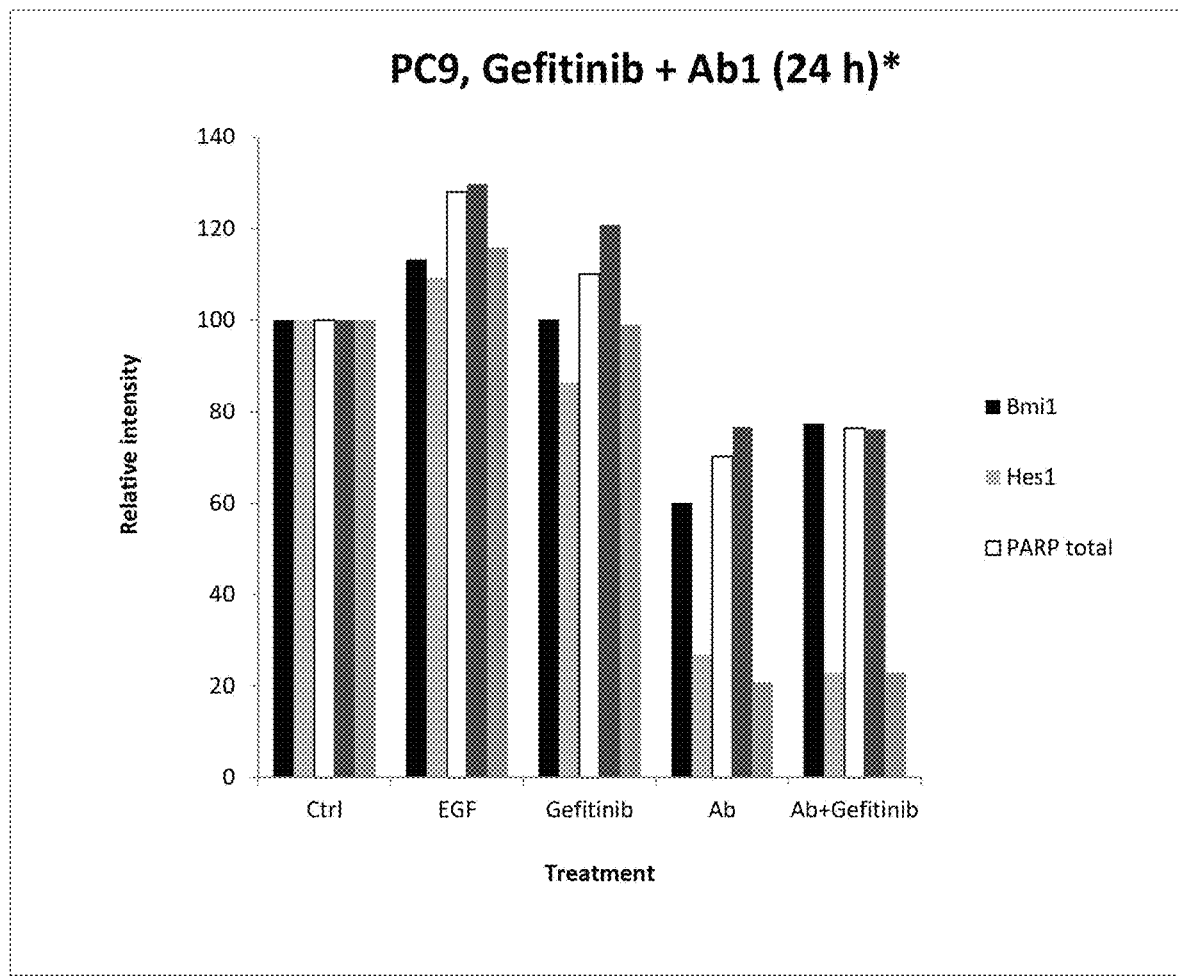
Figure 21C:
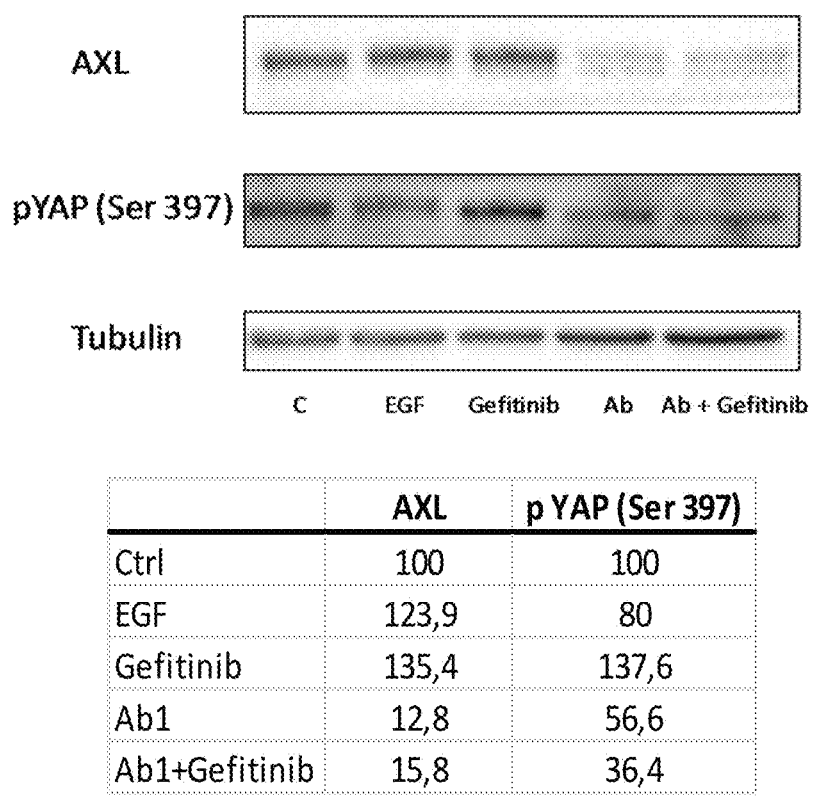
Figure 21D:
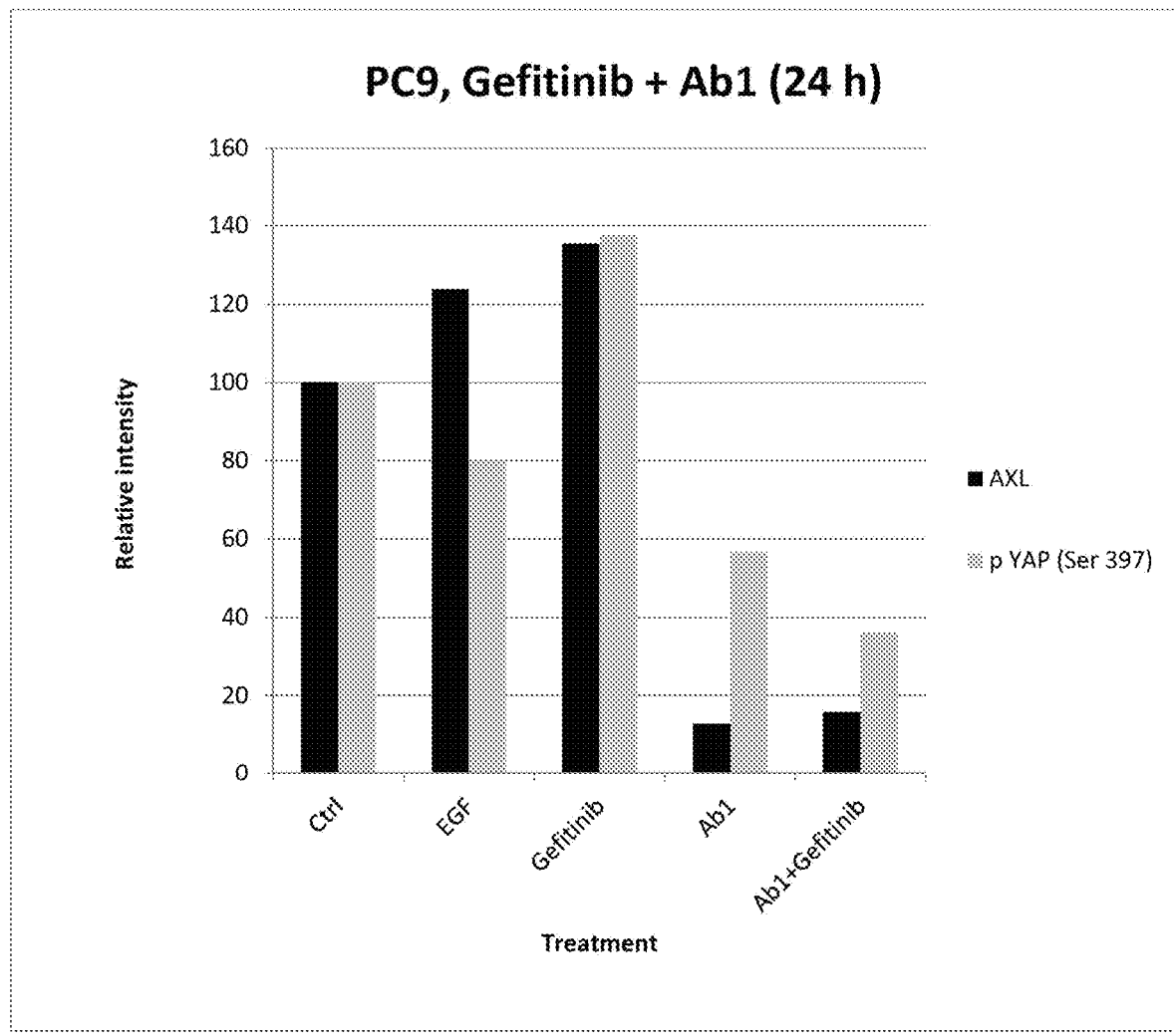
Figure 22A:
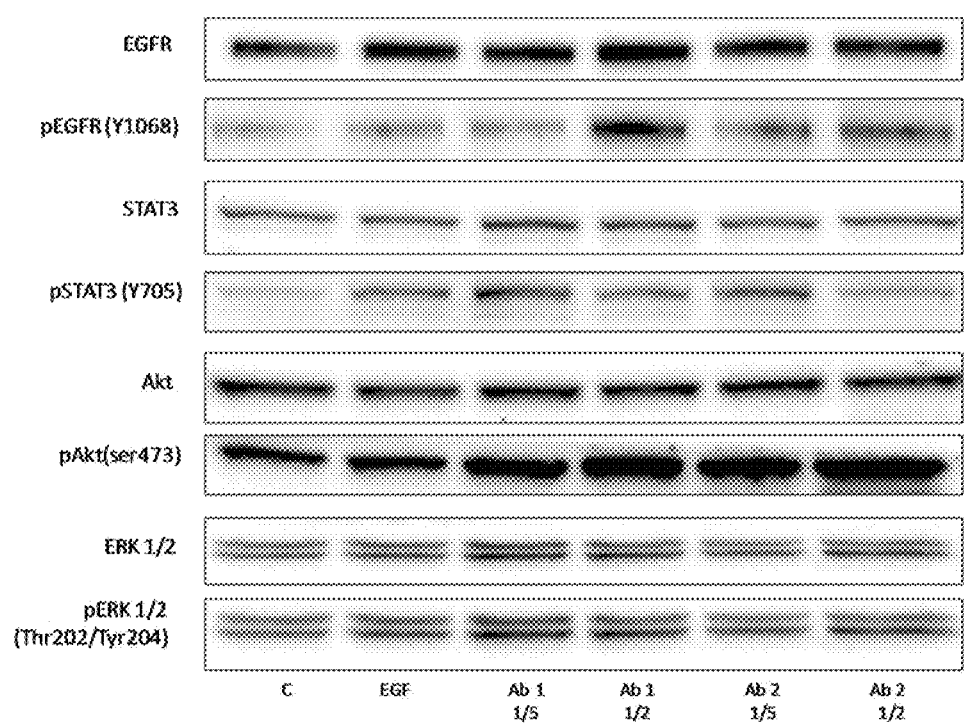
FIGS. 22A, 22B, 22C and 22D show the raw data in further experiment showing the comparison of anti-EGFs Ab1 and Ab2 in PC9 cells including additional makers.
Figure 22B:
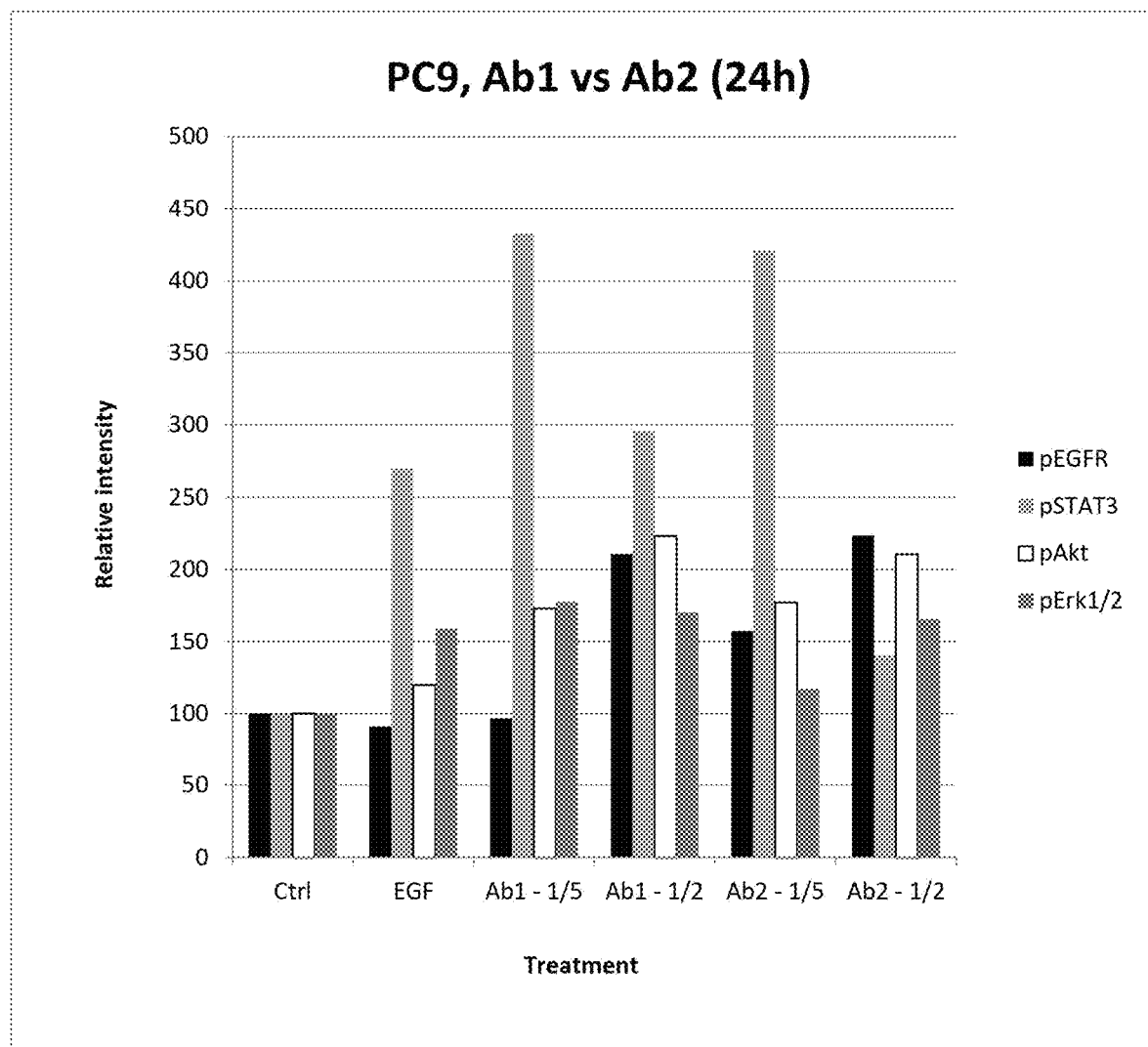
Figure 22C:
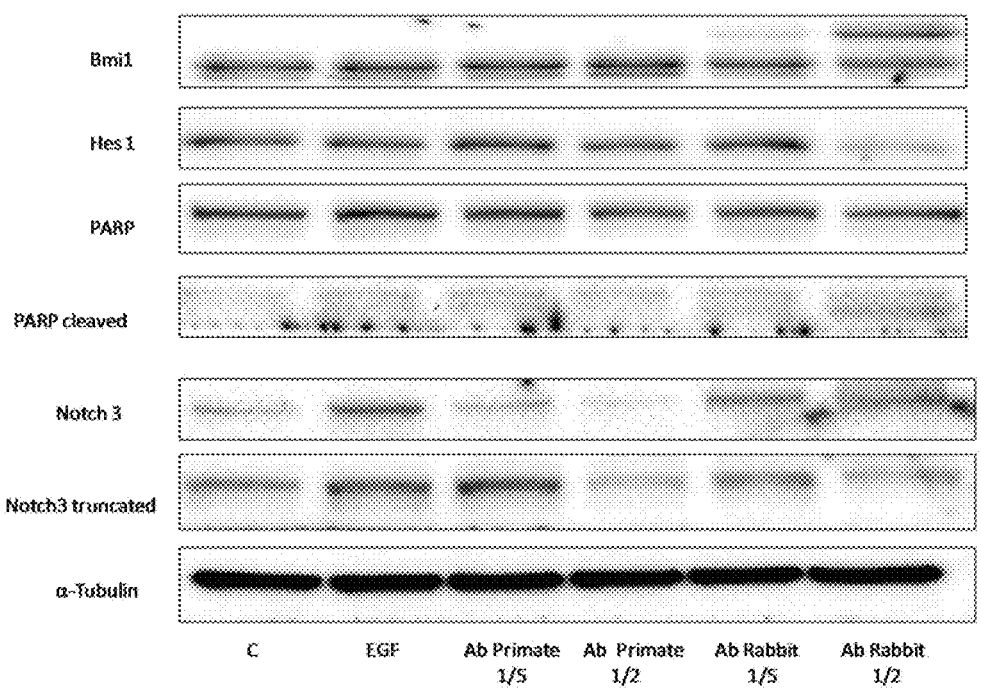
Figure 22D:
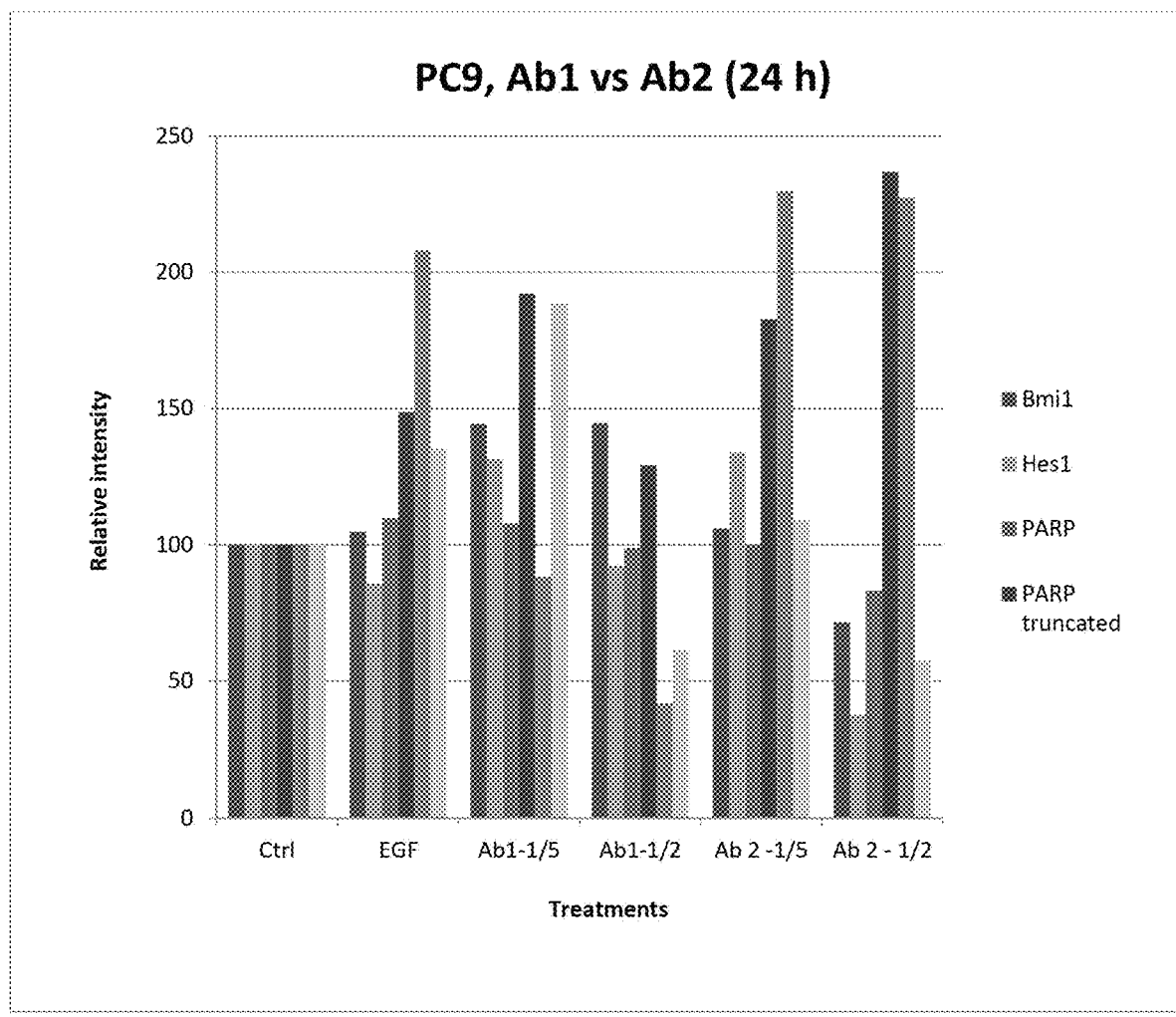

A further experiment was performed at 24 h and the same concentration of AZD9291 (that is within the range of physiological concentrations achieved in patients). The third generation TKI inhibited phosphorylation of EGFR, Akt and Erk but clearly activated STAT3 (similarly to our observations in the case of gefitinib and the sensitive PC9 cell line). The anti-EGF single agent stimulated pAkt and did not seem to have much effect on the other markers. However, the combination was clearly superior to both agents, with complete pEGFR and pErk inhibition, a reversal by AZD9291 of the antibody-induced phosphorylation of Akt and a blockade by the antibody of the STAT3 activation by AZD9291. As depicted in FIGS. 19A and 19B and summarized in table 5.

TABLE 5

|  | EGFR | STAT3 | Akt | Erk ½ |
|---|---|---|---|---|
| Ctrl | 100 | 100 | 100 | 100 |
| EGF | 116.4 | 150.6 | 98.5 | 96.5 |
| AZD9291 | 138.6 | 847.5 | 26.8 | 20.5 |
| Ab | 101 | 84.9 | 169 | 72.5 |
| Ab + AZ9291 | 0 | 503.9 | 63.8 | 1.6 |

Gefitinib and Anti-EGF (Ab1) in PC9 Cells. Additional Makers

In addition to STAT3, other markers and pathways have been related to the onset of resistance to gefitinib in EGFR-mutated tumor cells. A preliminary analysis was performed to test some of them: Notch3 cleaved (active form of Notch3), phosphor-YAP, Bmi1 and Hes1 (related to stem cells) and AXL (related to EMT transition). Also, PARP was investigated to determine if the antibodies induce apoptosis. Extracts of the PC9 cell line obtained in previous experiments were used. In a first experiment, the effects at 24 h of Ab1, gefitinib 0.5 μM and the combination on the markers cited above was evaluated. The anti-EGF antibody significantly down-regulated Hes1 and AXL and inhibited Notch cleavage and YAP phosphorylation. A not-so-significant down-regulation of Bmi1 was also observed. Gefitinib did not have any of these effects. Regarding PARP cleavage, both drugs were able to induce it after 24 h, as shown in FIGS. 21A, 21B, 21C and 21D and summarized in table 6 and 7

TABLE 6

|  | Bmi1 | Hes1 | PARP total | Notch3 | Notch3 truncated |
|---|---|---|---|---|---|
| Ctrl | 100 | 100 | 100 | 100 | 100 |
| EGF | 113.2 | 109.3 | 128 | 129.7 | 115.8 |
| Gefitinib | 100.1 | 86.5 | 110 | 120.8 | 98.9 |
| Ab | 60.1 | 26.7 | 70.2 | 76.7 | 20.8 |
| Ab + Gefitinib | 77.4 | 22.8 | 76.4 | 76.2 | 22.8 |

TABLE 7

|  | AXL | p YAP (Ser 397) |
|---|---|---|
| Ctrl | 100 | 100 |
| EGF | 123.9 | 80 |
| Gefitinib | 135.4 | 137.6 |
| Ab1 | 12.8 | 56.6 |
| Ab1 + Gefitinib | 15.8 | 36.4 |

Comparison of Anti-EGFs Ab1 and Ab2 in PC9 Cells (Including Additional Makers)

In a first, 24 h experiment the effects of Ab1 and Ab2 single agent were compared. Both antibodies stimulated pAkt in a similar way. In this experiment, they had no effect on pErk (but EGF also failed to induce it). Regarding STAT-3, the Ab2 at ½ induced a stronger inhibition of the EGF-stimulated phosphorylation of STAT-3. Results for pEGFR need to be repeated. Also, a 24 h experiment is pending. Regarding the rest of markers, the Ab2 was clearly more potent in down-regulating Hes1, blocking Notch3 cleavage and inducing PARP cleavage. It also triggered the appearance of an unexplained—for superior band in the case of Bmi1, as shown in FIGS. 22A, 22B, 22C and 22D and summarized in Table 8 and 9.

TABLE 8

|  | pEGFR | pSTAT3 | pAkt | pErk½ |
|---|---|---|---|---|
| Ctrl | 100 | 100 | 100 | 100 |
| EGF | 91 | 269.7 | 119.8 | 159.2 |
| Ab1-⅕ | 96.7 | 432.3 | 173.2 | 177.7 |
| Ab1-½ | 210.7 | 295.7 | 223.1 | 170.5 |
| Ab2-⅕ | 157.6 | 421.2 | 177.3 | 116.9 |
| Ab2-½ | 223.5 | 140.5 | 210.6 | 165.6 |

TABLE 9

|  | Ctrl | EGF | Ab1-⅕ | Ab1-½ | Ab 2-⅕ | Ab 2-½ |
|---|---|---|---|---|---|---|
| Bmi1 | 100 | 104.8 | 144.4 | 144.7 | 106 | 71.3 |
| Hes1 | 100 | 85.9 | 131.6 | 92.4 | 134 | 37.5 |
| PARP | 100 | 109.9 | 107.9 | 98.9 | 100.2 | 83.3 |
| PARP truncated | 100 | 148.7 | 192.2 | 129.3 | 182.9 | 236.8 |
| Notch | 100 | 208 | 88.3 | 41.8 | 229.7 | 227.2 |
| Notch truncated | 100 | 135.6 | 188.6 | 61.5 | 109.2 | 57.4 |

Findings

Figure 23:
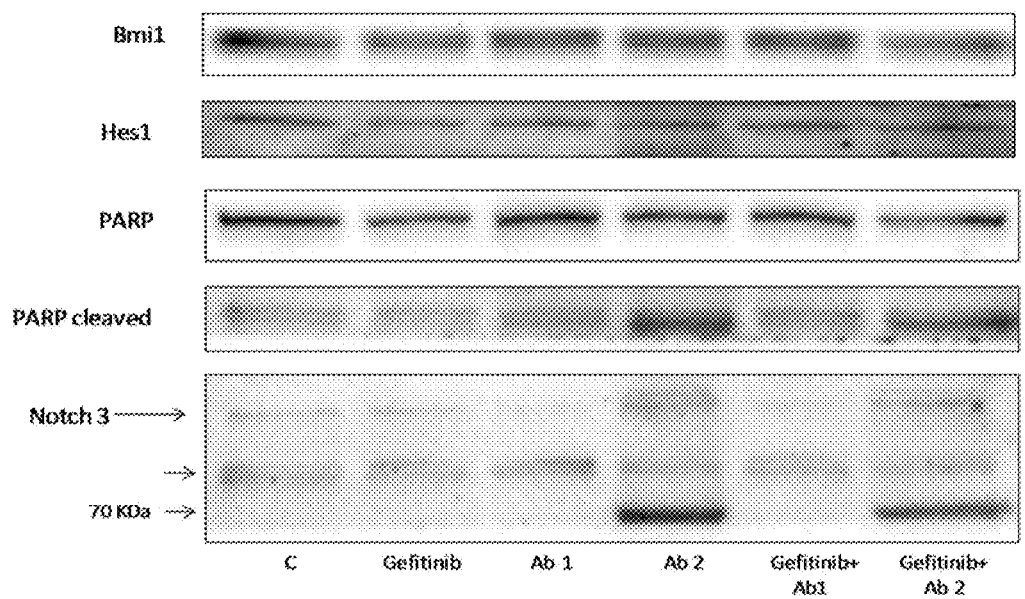
FIG. 23 shows the raw data for cells that were grown in human serum instead of inducing them with EGF displaying the appearance of hyper-phosphorylated Notch3, Akt and STAT-3 bands of lower molecular weight than the wild-type protein.
Figure 24:
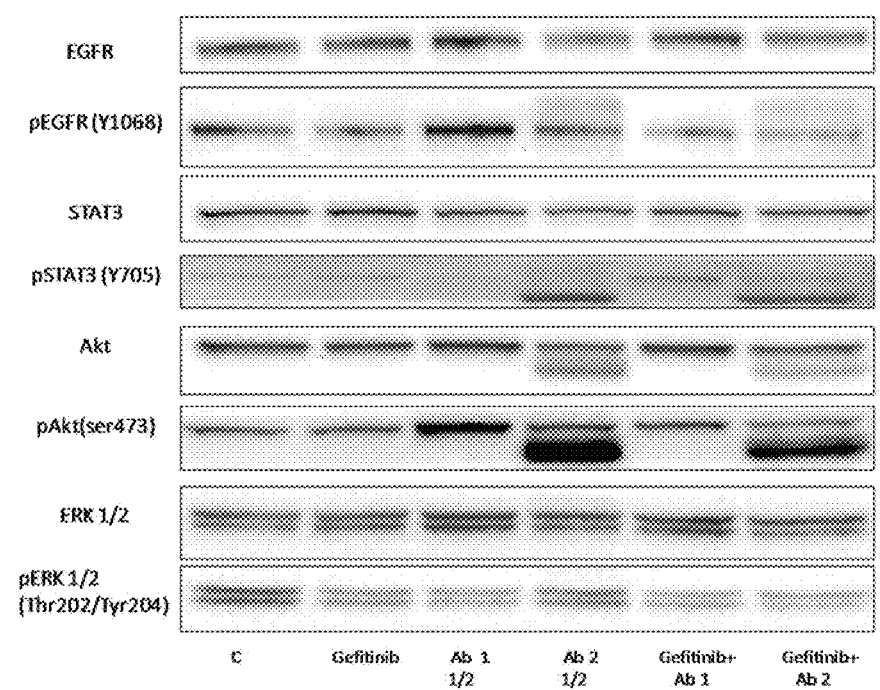
FIG. 24 shows a strong induction of PARP cleavage by Ab2, significantly stronger than that observed at 24 h.

In view of the positive results obtained in this experiment, the effects of the two antibodies single-agent and in combination with gefitinib after 5 day incubation were assessed. Cells were grown in human serum instead of inducing them with EGF (see methods). One of the most remarkable findings was the appearance of hyper-phosphorylated Notch3, Akt and STAT-3 bands of lower molecular weight than the wild-type protein as shown in FIG. 23. These bands could be originated by several reasons, being the most likely a proteolytic cleavage. The effects on Bmi1 and Hes1 observed after 24 h were not yet visible. In contrast, there was a strong induction of PARP cleavage by Ab2, significantly stronger than that observed at 24 h as depicted in FIG. 24 (Note: These Western blots were not quantified due to the appearance of the extra bands)

CONCLUSIONS

Administration of AZD9291 for 24 h to the EGFR-mutated, TKI sensitive PC9 cells and to the T790M, EGFR mutated, AZD9291-sensitive PC9-GR4 leads to activation of STAT3, considered as first step in acquisition of resistance to therapy.

The anti-EGF (Ab1) single agent activates Akt but this effect is reversed when AZD9291 is also present.

Combination treatment with AZD9291 and anti-EGF (Ab1) shows synergistic effect for pEGFR and pERK1/2 inhibition and blocks the activation of the four proteins under study (EGFR, ERK, Akt, STAT3) in the two cell lines tested (PC9, PC9-GR4). Remarkably, the combination treatment reproducibly reverses the activation of STAT3 by gefitinib or AZD9291.

In combination, the addition of anti-EGF (Ab1) has the following effects on effect of Gefitinib as immunotherapy: inhibits YAP3, not affected by TKI; Inhibits AXL, EMT marker, not affected by TKI; inhibits cleavage of Notch3, not affected by TKI; Reduces RES1, cancer stem cell marker, not affected by TKI; and increased PARP Cleavage.

Moreover addition of anti EGF to TKI reverses the activation of STAT3, one of the hallmarks of TKI, however directly linked to emergence of resistance.

The anti-EGF (Ab1) single agent also affects a multiplicity of pathways involved in resistance to TKIs. At 24 h, it blocks YAP phosphorylation, Notch cleavage and down-regulates AXL and Hes1. Both Gefitinib and the antibody induce PARP cleavage (marker of apoptosis).

This experimental data evidence adds further strength to the prior findings that that first-line combination treatment could be beneficial in EGFR mutated NSCLC patients since it has the potential to delay the appearance of resistance to TKIs.

The antibody derived from rabbit (Ab2) is superior or at least equal to the antibody derived from primate (Ab1) in terms of pSTAT3 blockade, down-regulation of stem cell markers and induction of apoptosis.

The antibody Ab2 induces cleavage of some key proteins, such as Notch3, STAT3 or Akt, a phenomenon that needs to be further addressed. From the literature we understand that Caspase 3 can cleave Akt.

Although exemplary embodiments have been presented in order to further elucidate these teachings, it should be noted that these teachings are not limited only to those exemplary embodiment.

Although the invention has been described with respect to various embodiments, it should be realized these teachings are also capable of a wide variety of further and other embodiments within the spirit and scope of the appended claims.

Although the invention has been described with respect to various embodiments showing synergistic combinations of TKIs and Anti-EGF antibodies, it will be appreciated by one skilled in the art that the combination treatment may be further combined with various chemotherapeutic regimens to augment the therapeutic effect of chemotherapy in the treatment of cancer.

The specification is most thoroughly understood in light of the teachings of the references cited within the specification. The embodiments within the specification provide an illustration of embodiments of the invention and should not be construed to limit the scope of the invention. One skilled in the art readily recognizes that many other embodiments are encompassed by the invention. Those skilled in the art will recognize, or be able to ascertain using no more than routine experimentation, many equivalents to the specific embodiments of the invention described herein. Such equivalents are intended to be encompassed by the following appended claims.

What is claimed is:

1. A method of treating a patient suffering from a non-small cell lung cancer (NSCLC) that is responsive to treatment with an Epidermal Growth Factor Receptor tyrosine kinase inhibitor (EGFR-TKI) and driven by deregulated Human Epidermal Growth Factor Receptor (HER/Human EGFR) with a combination therapy, comprising:
administering to the patient a therapeutically effective amount of the EGFR-TKI and an immunogenic polypeptide comprising Epidermal Growth Factor (EGF) at an amount effective to generate an immune response against the EGF via active immunization,
wherein the EGFR-TKI is administered according to a continuous regimen based on an average daily dose in the range of 10 mg to 150 mg and the immunogenic polypeptide is co-administered according to a therapeutically effective amount,
wherein the EGFR-TKI is selected from the group consisting of gefitinib, erlotinib, and pharmaceutically acceptable salts thereof.

2. The method of claim 1, wherein the EGFR-TKI is administered according to a continuous regimen based on an average daily dose in the range of 10 mg to 150 mg and the immunogenic polypeptide is co-administered according to a therapeutically effective amount repeated thrice, twice or once a week, once in two weeks, once in three weeks or at least once monthly, wherein the patient has a tumor expressing mutated forms of the EGFR.

3. The method of claim 1, wherein the EGFR-TKI is administered according to a continuous regimen based on an average daily dose in the range of 10 mg to 150 mg, and the immunogenic polypeptide is co-administered according to a therapeutically effective amount repeated twice or once a week or once in two weeks.

4. The method of claim 1, wherein the EGFR-TKI is administered according to a continuous regimen based on an average daily dose in the range of 10 mg to 150 mg, and the immunogenic polypeptide is co-administered according to a therapeutically effective amount repeated twice or once a week or once in two weeks.

5. The method of claim 1, wherein the patient has a tumor expressing a mutated form of the EGFR.

6. The method of claim 1, wherein the NSCLC is a metastatic form of NSCLC.

7. A method of treating a patient suffering from a non-small cell lung cancer (NSCLC) that is responsive to treatment with an Epidermal Growth Factor Receptor tyrosine kinase inhibitor (EGFR-TKI) and driven by deregulated Human Epidermal Growth Factor Receptor (HER1/Human EGFR) including mutation T790M with a combination therapy, comprising:
administering to the patient EGFR-TKI and an immunogenic polypeptide comprising Epidermal Growth Factor (EGF) at an amount effective generate an immune response against the EGF via active immunization,
wherein the immunogenic polypeptide is administered according to a therapeutically effective amount, prior to the administration of the EGFR-TKI in a continuous regimen based on an average daily dose in the range of 10 mg to 250 mg.

* * * * *

SEQUENCE LISTING

```
<160> NUMBER OF SEQ ID NOS: 2

<210> SEQ ID NO 1
<211> LENGTH: 234
<212> TYPE: PRT
<213> ORGANISM: Oryctolagus cuniculus

<400> SEQUENCE: 1

Met Asn Ser Tyr Pro Gly Cys Pro Ser Tyr Asp Gly Tyr Cys Leu
1               5                   10                  15

Asn Gly Gly Val Cys Met His Ile Glu Ser Leu Asp Ser Tyr Thr Cys
                20                  25                  30

Asn Cys Val Ile Gly Tyr Ser Gly Asp Arg Cys Gln Thr Arg Asp Leu
            35                  40                  45

Arg Trp Trp Glu Leu Arg Gly Ser Ser Gly Asn Ser Asp Ser Glu Cys
    50                  55                  60

Pro Leu Ser His Asp Gly Tyr Cys Leu His Asp Gly Val Cys Met Tyr
65                  70                  75                  80

Ile Glu Ala Leu Asp Lys Tyr Ala Cys Asn Cys Val Val Gly Tyr Ile
                85                  90                  95

Gly Glu Arg Cys Gln Tyr Arg Asp Leu Lys Trp Trp Glu Leu Arg Gly
                100                 105                 110

Gly Ser Gly Gly Thr Ser Gly Gly Gly Gly Ser Gly Thr Pro Gln
            115                 120                 125

Asn Ile Thr Asp Leu Cys Ala Glu Tyr His Asn Thr Gln Ile His Thr
    130                 135                 140

Leu Asn Asp Lys Ile Phe Ser Tyr Thr Glu Ser Leu Ala Gly Lys Arg
145                 150                 155                 160

Glu Met Ala Ile Ile Thr Phe Lys Asn Gly Ala Thr Phe Gln Val Glu
                165                 170                 175

Val Pro Gly Ser Gln His Ile Asp Ser Gln Lys Lys Ala Ile Glu Arg
            180                 185                 190

Met Lys Asp Thr Leu Arg Ile Ala Tyr Leu Thr Glu Ala Lys Val Glu
        195                 200                 205

Lys Leu Cys Val Trp Asn Asn Lys Thr Pro His Ala Ile Ala Ala Ile
    210                 215                 220

Ser Met Ala Asn His His His His His His
225                 230

<210> SEQ ID NO 2
<211> LENGTH: 227
<212> TYPE: PRT
<213> ORGANISM: Oryctolagus cuniculus

<400> SEQUENCE: 2

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
                20                  25                  30
```

```
Cys Val Val Gly Tyr Ile Gly Glu Arg Cys Gln Tyr Arg Asp Leu Lys
        35                  40                  45

Trp Trp Glu Leu Arg Gly Ser Ser Gly Asn Ser Asp Ser Glu Cys Pro
    50                  55                  60

Leu Ser His Asp Gly Tyr Cys Leu His Asp Gly Val Cys Met Tyr Ile
65                  70                  75                  80

Glu Ala Leu Asp Lys Tyr Ala Cys Asn Cys Val Val Gly Tyr Ile Gly
                85                  90                  95

Glu Arg Cys Gln Tyr Arg Asp Leu Lys Trp Trp Glu Leu Arg Gly Gly
                100                 105                 110

Ser Gly Gly Thr Ser Gly Gly Gly Gly Ser Gly Thr Pro Gln Asn
            115                 120                 125

Ile Thr Asp Leu Cys Ala Glu Tyr His Asn Thr Gln Ile His Thr Leu
        130                 135                 140

Asn Asp Lys Ile Phe Ser Tyr Thr Glu Ser Leu Ala Asp Lys Arg Glu
145                 150                 155                 160

Met Ala Ile Ile Thr Phe Lys Asn Gly Ala Thr Phe Gln Val Glu Val
                165                 170                 175

Pro Gly Ser Gln His Ile Asp Ser Gln Lys Lys Ala Ile Glu Arg Met
            180                 185                 190

Lys Asp Thr Leu Arg Ile Ala Tyr Leu Thr Glu Ala Lys Val Glu Lys
        195                 200                 205

Leu Cys Val Trp Asn Asn Lys Thr Pro Pro Ala Ile Ala Ala Ile Ser
    210                 215                 220

Met Ala Asn
225
```